US012774466B2

(12) United States Patent
Boileau et al.

(10) Patent No.: US 12,774,466 B2
(45) Date of Patent: Oct. 27, 2026

(54) COMPOUNDS FOR USE IN THE TREATMENT OF EPILEPSY

(71) Applicants: INSERM (INSTITUT NATIONAL DE LA SANTÉ ET DE LA RECHERCHE MEDICALE), Paris (FR); UNIVERSITÉ D'AIX-MARSEILLE, Marseilles (FR); UNIVERSITÉ DE BORDEAUX, Bordeaux (FR); REGENXBIO INC., Rockville, MD (US); CENTRE NATIONAL DE LA RECHERCHE SCIENTIFIQUE, Paris (FR)

(72) Inventors: Céline Boileau, Marseilles (FR); Valérie Crepel, Marseilles (FR); Séverine Deforges, Bruges (FR); Julie Masante, Saint Jean d'illac (FR); Christophe Mulle, Pessac (FR); Angélique Peret, Marseilles (FR); Olivier Danos, Rockville, MD (US); Andrew Mercer, Rockville, MD (US)

(73) Assignees: Inserm (Institut National De La Santé Et De La Recherche Médicale), Paris (FR); UNIVERSITÉ D'AIX MARSEILLE, Marseilles (FR); UNIVERSITÉ DE BORDEAUX, Bordeaux (FR); REGENXBIO INC., Rockville, MD (US); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 807 days.

(21) Appl. No.: 18/014,977

(22) PCT Filed: Jul. 9, 2021

(86) PCT No.: PCT/EP2021/069186
§ 371 (c)(1),
(2) Date: Jan. 6, 2023

(87) PCT Pub. No.: WO2022/008725
PCT Pub. Date: Jan. 13, 2022

(65) Prior Publication Data
US 2023/0323366 A1 Oct. 12, 2023

(30) Foreign Application Priority Data
Jul. 10, 2020 (WO) ................ PCT/EP2020/069610

(51) Int. Cl.
*C12N 15/113* (2010.01)
*A61P 25/08* (2006.01)
*C12N 7/00* (2006.01)
*C12N 15/86* (2006.01)

(52) U.S. Cl.
CPC .......... *C12N 15/1136* (2013.01); *A61P 25/08* (2018.01); *C12N 7/00* (2013.01); *C12N 15/1138* (2013.01); *C12N 15/86* (2013.01); *C12N 2310/11* (2013.01); *C12N 2310/531* (2013.01); *C12N 2750/14142* (2013.01); *C12N 2750/14143* (2013.01)

(58) Field of Classification Search
None
See application file for complete search history.

(56) References Cited

U.S. PATENT DOCUMENTS 4,975,430 A 12/1990 Jahr et al.
6,180,613 B1 1/2001 Kaplitt et al.
8,258,286 B2 9/2012 Davidson et al.
9,353,373 B2 5/2016 Rao et al.
(Continued)

FOREIGN PATENT DOCUMENTS

CA 3177789 A1 11/2022
CN 103695327 A 4/2014
(Continued)

OTHER PUBLICATIONS

Tang and Khvorova (RNAi-based drug design: considerations and future directions. Nat Rev Drug Discov. May 2024;23(5):341-364).*
(Continued)

*Primary Examiner* — Christopher M Babic
(74) *Attorney, Agent, or Firm* — Clark & Elbing LLP

(57) ABSTRACT

The present disclosure relates to gene therapy targeting GluK2 subunit that can be used to inhibit epileptiform discharges. Short interfering RNA sequences against the human Grik2 gene sequence are described which are efficient in decreasing the expression of GluK2-containing KARs in neurons engineered to express the equivalent shRNA or miRNA. Using a tissue culture model of TLE, the examples remarkably demonstrate that viral expression of shRNA or miRNA inhibits the frequency of epileptiform discharges. Therefore, RNA therapeutics aimed at decreasing the expression of GluK2-containing KARs in neurons can remarkably prevent spontaneous epileptiform discharges in TLE. In particular, the present disclosure relates to a recombinant antisense oligonucleotide that targets a Grik2 mRNA. The present disclosure also relates to a method for treating epilepsy in a subject in need thereof, wherein the method comprises: administering an effective amount of a vector comprising an oligonucleotide encoding an inhibitory RNA that binds (e.g., hybridizes) specifically to Grik2 mRNA and inhibits expression of Grik2 in the subject.

18 Claims, 7 Drawing Sheets

Specification includes a Sequence Listing.

(56) References Cited

U.S. PATENT DOCUMENTS

| | | | |
|---|---|---|---|
| 10,016,424 B2 | 7/2018 | Crepel et al. | |
| 10,174,321 B2 | 1/2019 | Konstantinova et al. | |
| 2002/0019495 A1 | 2/2002 | Murugan et al. | |
| 2002/0191495 A1 | 12/2002 | Verschuren | |
| 2005/0214823 A1* | 9/2005 | Blume ................. | C12Q 1/6876 435/6.1 |
| 2005/0255487 A1 | 11/2005 | Khvorova et al. | |
| 2006/0233711 A1 | 10/2006 | Zhuo | |
| 2008/0113351 A1 | 5/2008 | Naito et al. | |
| 2008/0280848 A1 | 11/2008 | Patzel et al. | |
| 2013/0302407 A1 | 11/2013 | Rao et al. | |
| 2016/0228439 A1* | 8/2016 | Crepel ................. | A61K 31/513 |
| 2018/0064748 A1 | 3/2018 | Hornstein et al. | |
| 2018/0193414 A1 | 7/2018 | Greenberg et al. | |
| 2019/0194753 A1 | 6/2019 | Scherer | |
| 2021/0047641 A1 | 2/2021 | Stanek et al. | |
| 2021/0363525 A1 | 11/2021 | Sætrom et al. | |
| 2022/0251567 A1 | 8/2022 | Crepel et al. | |
| 2023/0039652 A1 | 2/2023 | Crepel et al. | |
| 2023/0227829 A1 | 7/2023 | Crepel et al. | |
| 2023/0323366 A1 | 10/2023 | Boileau et al. | |
| 2024/0018524 A1 | 1/2024 | Crepel et al. | |
| 2024/0287526 A1 | 8/2024 | Hassler et al. | |
| 2024/0417737 A1 | 12/2024 | He et al. | |
| 2025/0090689 A1 | 3/2025 | Keravala | |

FOREIGN PATENT DOCUMENTS

| | | | |
|---|---|---|---|
| EP | 1752536 | A1 | 2/2007 |
| EP | 1504126 | B1 | 2/2014 |
| TW | 202337475 | A | 10/2023 |
| WO | WO-01/72709 | A1 | 10/2001 |
| WO | WO-02/092086 | A1 | 11/2002 |
| WO | WO-03074654 | A2 | 9/2003 |
| WO | WO-2005044981 | A2 | 5/2005 |
| WO | WO-2005/0116204 | A1 | 12/2005 |
| WO | WO-2005/124343 | A2 | 12/2005 |
| WO | WO-2007/101116 | A2 | 9/2007 |
| WO | WO-2008/134646 | A2 | 11/2008 |
| WO | WO-2014/096418 | A2 | 6/2014 |
| WO | WO-2015/036618 | A1 | 3/2015 |
| WO | WO-2016/157175 | A1 | 10/2016 |
| WO | WO-2016/170348 | A2 | 10/2016 |
| WO | WO-2018200844 | A1 | 11/2018 |
| WO | WO-2021/005223 | A1 | 1/2021 |
| WO | WO-2022/008725 | A1 | 1/2022 |
| WO | WO-2022/011262 | A1 | 1/2022 |
| WO | WO-2022/245734 | A2 | 11/2022 |
| WO | WO-2024079078 | A1 | 4/2024 |
| WO | WO-2024246162 | A1 | 12/2024 |

OTHER PUBLICATIONS

Boudreau et al. (RNAi medicine for the brain: progresses and challenges. Hum Mol Genet. Apr. 15, 2011;20(R1):R21-7).*

Inoue et al. (GRIK2 has a role in the maintenance of urothelial carcinoma stem-like cells, and its expression is associated with poorer prognosis. Oncotarget. Apr. 25, 2017;8(17):28826-28839).*

Webb et al. (Pathological gain-of-function human variants in the GRIK2 kainate receptor gene cause wide-ranging behavioral dysfunction and seizures in mouse models. Neurobiol Dis. Dec. 13, 2025;218:107226).*

Borel et al., "Design of AAV Vectors for Delivery of RNAi," Methods Mol Biol. 3-18 (2019).

Boudreau et al., "RNAi medicine for the brain: progresses and challenges," Hum Mol Genet. 20(R1):R21-7 (2011).

Bowers et al., "Genetic therapy for the nervous system," Hum Mol Genet. 20(r1):R28-41 (2011).

Castanotto et al., "Combinatorial delivery of small interfering RNAs reduces RNAi efficacy by selective incorporation into RISC," Nucleic Acids Res. 35(15): 5154-64 (2007).

Cho et al., "Chapter 8: RNAi Therapeutic Potentials and Prospects in CNS Disease," *RNA Interference*. Ibrokhim Y. Abdurakhmonov, 165-190 (2016) (26 pages).

Collingridge et al., "A nomenclature for ligand-gated ion channels," available in PMC Mar. 30, 2010, published in final edited form as: Neuropharmacology. 56(1):2-5 (2009) (11 pages).

Contractor et al., "Kainate receptors coming of age: milestones of two decades of research," Trends Neurosci. 34(3):154-63 (2011).

Falcon-Moya et al. "Kainate Receptors: Role in Epilepsy," Frontiers in Molecular Neuroscience. 11(217):1-7 (2018).

Foster et al., "Glutamate- and GABA-based CNS therapeutics," Curr Opin Pharmacol. 6(1):7-17 (2006).

Fritsch et al., "Role of GluK1 Kainate Receptors in Seizures, Epileptic Discharges, and Epileptogenesis," J Neurosci. 34(17):5765-75 (2014).

Gong et al., "A Cold-Sensing Receptor Encoded by a Glutamate Receptor Gene," Cell. 178(6):1375-86 (2019) (24 pages).

International Preliminary Report on Patentability for International Application No. PCT/EP2020/069610, issued Jan. 11, 2022 (7 pages).

International Preliminary Report on Patentability for International Application No. PCT/US2021/041089, issued Jan. 10, 2023 (13 pages).

International Preliminary Report on Patentability for PCT/EP2021/069186, dated Jan. 10, 2023 (7 pages).

International Search Report and Written Opinion for International Application No. PCT/EP2020/069610, mailed Oct. 9, 2020 (13 pages).

International Search Report and Written Opinion for International Application No. PCT/US2021/041089, mailed Dec. 9, 2021 (23 pages).

International Search Report and Written Opinion for International Application No. PCT/US22/29452, mailed Dec. 5, 2020 (27pages).

Jane et al., "Kainate receptors: Pharmacology, function and therapeutic potential," Neuropharmacology. 56(1):90-113 (2009).

Jaremko et al., "A kainate receptor-selective RNA aptamer," J Biol Chem. 295(19):6280-8 (2020).

Khodr et al., "Targeting alpha-synuclein with a microRNA-embedded silencing vector in the rat substantia nigra: positive and negative effects," available in PMC Mar. 6, 2015, published in final edited form as: Brain Res. 1550:47-60 (2014) (23 pages).

Larsen et al., "Medicinal Chemistry of Competitive Kainate Receptor Antagonists," ACS Chem Neurosci. 2(2):60-74 (2011).

Li et al., "Down-regulation of GluK2 kainate receptor expression by chronic treatment with mood-stabilizing anti-convulsants or lithium in cultured astrocytes and brain, but not in neurons," Neuropharmacology. 57(4):375-85 (2009).

Matute, "Therapeutic Potential of Kainate Receptors," CNS Neurosci Ther. 17(6):661-9 (2011).

Namba et al., "Antiepileptogenic and anticonvulsant effects of NBQX, a selective AMPA receptor antagonist, in the rat kindling model of epilepsy," Brain Res. 638(1-2):36-44 (1994).

Nilsen et al., "Characterization of the Tetanus Toxin Model of Refractory Focal Neocoritcal Epilepsy in the Rat," Epilepsia. 46(2):179-187 (2005).

Noland et al., "Multiple sensors ensure guide strand selection in human RNAi pathways," RNA. 19(5):639-48 (2013).

Peret et al. "Contribution of aberrant GluK2-containing kainate receptors to chronic seizures in temporal lobe epilepsy," Cell Rep. 8(2):347-54 (2014).

Pinheiro et al., "Kainate receptors," Cell Tissue Res. 326(2):457-82 (2006) (27 pages).

Pinheiro et al., "Selective Block of Postsynaptic Kainate Receptors Reveals Their Function at Hippocampal Mossy Fiber Synapses," Cerebral Cortex. 23(2):323-31 (2013).

Reiner et al., "Assembly Stoichiometry of the GluK2/GluK5 Kainate Receptor Complex," Cell Rep. 1(3):234-40 (2012).

Aartsma-Rus et al., "Guidelines for antisense oligonucleotide design and insight into splice-modulating mechanisms," Mol Ther. 17(3): 548-553 (Mar. 2009).

Amellem. "Establishment of a fluorescence-based RNA interference screening assay and post-transcriptional down-regulation of the kainate receptor subunit GRIK2." Master thesis. Available Dec 2014. NTNU, Trondheim.

(56) References Cited

OTHER PUBLICATIONS

Avoli et al., "Network and pharmacological mechanisms leading to epileptiform synchronization in the limbic system in vitro," Progress in Neurobiology. 68(3):167-207 (Oct. 2002) (Abstract Only).
Barberis et al., "GluR6/KA2 Kainate Receptors Mediate Slow-Deactivating Currents," J Neuroscience. 28(25):6402-6406 (Jun. 2008) (5 pages).
Barbon et al., "Genomic organization of the human GRIK2 gene and evidence for multiple splicing variants," Gene. 274(1-2):187-97 (Aug. 2001).
Bleakman et al., "Pharmacological characterization of a GluR6 kainate receptor in cultured hippocampal neurons," European J. Pharmacology. 378:331-337 (1999) (7 Pages).
Boileau et al., "Development of a novel AAV9 gene therapy for the treatment of temporal lobe epilepsy using animal model and human organotypic slices," European Society of Gene and Cell Ther. 29th Congress (Oct. 2022) (1 page).
Boileau et al., "GluK2 is a Target for Gene Therapy in Drug-Resistant Temporal Lobe Epilepsy," Ann Neurol. 94(4):745-761 (Oct. 2023) (17 pages).
Bureau et al., "Kainate Receptor-Mediated Responses in the CA1 Field of Wild-Type and GluR6-Deficient Mice," J Neuroscience. 19(2):653-663 (Jan. 1999) (11 Pages).
Communication pursuant to Article 94(3) EPC for European Patent Application No. 14766481.7, dated Apr. 2, 2019 (6 pages).
Communication pursuant to Article 94(3) EPC for European Patent Application No. 14766481.7, dated Jul. 16, 2020 (5 pages).
Communication pursuant to Article 94(3) EPC for European Patent Application No. 14766481.7, dated Jul. 5, 2023 (4 pages).
Communication pursuant to Article 94(3) EPC for European Patent Application No. 14766481.7, dated May 24, 2022 (6 pages).
Crepel et al., "Physiopathology of kainate receptors in epilepsy," Current Opinion in Pharmacology. 20:83-88 (Feb. 2015) (Abstract Only).
Dolman et al., "Synthesis and Pharmacological Characterization of N3-Substituted Willardiine Derivatives: Role of the Substituent at the 5-Position of the Uracil Ring in the Development of Highly Potent and Selective GLUK5 Kainate Receptor Antagonists," J. Med. Chem. 50:1558-1570 (Mar. 2007) (13 Pages).
Egebjerg et al., "Cloning of a cDNA For a Glutamate Receptor Subunit Activated By Kainate but Not Ampa," Nat. 351(6369):745-748 (Jun. 1991) (Abstract Only).
English Translation for Chinese Application No. 103695327, published Apr. 2, 2014, Machine Translation (20 pages).
European Search Report for European U.S. Appl. No. 13/306,265, dated Jan. 22, 2014 (6 pages).
Fakhr et al., "Precise and efficient siRNA design: a key point in competent gene silencing," Cancer Gene Ther. 23(4): 73-82 (Apr. 2016).
Fang & Bartel et al., "The Menu of Features that Define Primary MicroRNAs and Enable De Novo Design of MicroRNA Genes." Molecular Cell 60(1);131-145, Oct. 1, 2015.
Fiévre et al., "Molecular determinants for the strictly compartmentalized expression of kainate receptors in CA3 pyramidal cells," Nature. 7:12738 (Sep. 2016) (12 Pages).
GenBank Accession No. HQ456318, "Retrovial Tet-shRNA expression vector TtRMPVIR, complete sequence," <Retroviral Tet-shRNA expression vector TtRMPVIR, complete sequence—Nucleotide—NCBI>, dated Nov. 11, 2010, retrieved on Jun. 23, 2025.
Germain et al., "RNA interference (RNAi)-based therapeutics for treatment of rare neurologic diseases," Mol Aspects Med. 91:101148 (Jun. 2023) (9 pages).
Herb et al., "The KA-2 subunit of excitatory amino acid receptors shows widespread expression in brain and forms ion channels with distantly related subunits," Neuron Apr. 8(4):775-785 (Apr. 1992) (Abstract Only).
*Homo sapiens* glutamate ionotropic receptor kainate type subunit 2 (GRIK2), transcript variant 2, mRNA, GenBank, accession No. NM_175768, accessed Aug. 22, 2024, (7 pages).
Iida et al., "A comparative analysis of kainate receptor GluK2 and GluK5 knockout mice in a pure genetic background," Behav Brain Res. 405:113194 (May 2021) (13 pages).
International Preliminary Report on Patentability for International Application No. PCT/EP2014/069709, issued Mar. 22, 2016 (6 pages).
International Preliminary Report on Patentability for International Application No. PCT/US2022/029452, issued Nov. 21, 2023 (13 pages).
International Search Report and Written Opinion for International Application No. PCT/EP2014/069709, mailed Oct. 29, 2014 (10 pages).
International Search Report and Written Opinion for International Application No. PCT/EP2021/069186, mailed Dec. 2, 2021 (11 pages).
International Search Report and Written Opinion for International Application No. PCT/EP2023/077967, mailed Feb. 2, 2024 (15 pages).
"Kainate receptor," Wikipedia (retrieved on Nov. 13, 2017) (1 page).
Kim D. and Rossi J., "RNAi mechanisms and applications," available in PMC Aug. 14, 2009, published in final edited form as: Biotechniques 44(5):613-616 (Apr. 2008) (7 Pages).
Office Action for Canadian Patent Application No. 3,177,613, dated Feb. 2, 2024 (3 pages).
Office Action for Canadian Patent Application No. 3177789, dated Jan. 31, 2024 (4 pages).
Pearson et al., "Biodistribution and safety of a novel AAV9 gene therapy for treatment of temporal lobe epilepsy shown in non-human primates," European Society of Gene and Cell Ther. 29th Congress (Oct. 2022) (1 page).
Schidlitzki et al., "A combination of NMDA and AMPA receptor antagonists retards granule cell dispersion and epileptogenesis in a model of aquired epilepsy," Scientific Reports. 7:12191 (Sep. 2017) (18 Pages).
Song et al., "Selection of rAAV vectors that cross the human blood-brain barrier and target the central nervous system using a transwell model." Molecular Therapy Methods & Clinical Development, vol. 27, 73-88. (Dec 2022).
Zhou et al., "(2S,4R)-4-Methylglutamic Acid (SYM 2081): A Selective, High-Affinity Ligand for Kainate Receptors," J Pharmacology and Experimental Ther. 280:422-427 (1997) (6 Pages).
Bofill-De Ros & Gu, "Guidelines for the optimal design of miRNA-based shRNAs," available in PMC on Jul. 1, 2017, published in final editable form as Methods. 103:157-166 (23 Pages) (2016).
Wilmott et al., "A User's Guide to the Inverted Terminal Repeats of Adeno-Associated Virus," Human Gene Ther Methods. 30(6):206-213 (Dec. 2019).
Sciabola et al., "PFRED: A computational platform for siRNA and antisense oligonucleotides design." PLoS One 16.1 (Jan. 2021).
Klein et al., "AAV8, 9, Rh10, Rh43 Vector Gene Transfer in the Rat Brain: Effects of Serotype, Promoter and Purification Method." Molecular Therapy. 16:1, 89-96. (Jan. 2008).
Farina et al., "Separation of Domain Contacts is Required for Heterotetrameric Assembly of Functional NMDA Receptors," The Journal of Neuroscience. 31(10):3565-3579 (2011) (15 pages).

* cited by examiner

COMPOUNDS FOR USE IN THE TREATMENT OF EPILEPSY

FIELD OF THE DISCLOSURE

The disclosure is in the field of epilepsy, more particularly the disclosure relates to methods and compositions for treating epilepsy.

BACKGROUND OF THE DISCLOSURE

Temporal Lobe Epilepsy (TLE) is the most common form of partial epilepsy in adults (30-40% of all forms of epilepsies). It is well established that the hippocampus plays a key role in the pathophysiology of TLE. In human patients and animal models of TLE, an important rewiring of neuronal circuits occurs. One of the best examples of network reorganization ("reactive plasticity") is the sprouting of recurrent mossy fibers (rMF) that establish novel aberrant glutamatergic synapses onto dentate granule cells (DGCs) in the hippocampus (Tauck and Nadler, 1985; Represa et al., 1989a, 1989b; Sutula et al., 1989; Gabriel et al., 2004) leading to a recurrent excitatory circuit. As a key element with regards to this disclosure, these recurrent synapses operate through ectopic kainate receptors (KARs) (Epsztein et al., 2005; Artinian et al., 2011, 2015). In a collaborative work, Valérie Crépel (INMED, Marseille) and Christophe Mulle (IINS, Bordeaux) have explored the pathophysiological implications of ectopic synaptic KARs in chronic seizures in a mouse model of TLE. KARs tetrameric glutamate receptors assembled from the GluK1-GluK5 subunits. In heterologous expression systems, GluK1, GluK2, and GluK3 may form homomeric receptors, while GluK4 and GluK5 form heteromeric receptors in conjunction with GluK1-3 subunits. Native KARs are widely distributed in the brain with high densities of receptors found in the hippocampus (Carta et al, 2016, EJN), a key structure featuring in TLE. The inventors have demonstrated that epileptic activities including interictal spikes and ictal discharges were markedly reduced in mice lacking the GluK2 KAR subunit. Moreover, epileptiform activities were also strongly reduced following the use of pharmacological antagonists of GluK2/GluK5-containing KARs, which block ectopic synaptic KARs (Peret et al., 2014). These data have established that KARs ectopically expressed at rMFs in DGCs play a major role in chronic seizures in TLE. Therefore, aberrant ectopic KARs expressed in DGCs and composed of GluK2/GluK5 represent a promising target for the treatment of intractable TLE.

While hypothetical RNA interference (RNAi) strategies have been proposed for many disease targets, RNAi molecules capable of ameliorating disease are rare. For example, for over a decade, the huntingtin (Htt) gene seemed a likely candidate to knockdown in order to augment the outcome of Huntington's Disease. At least two thousand short interfering RNA (SIRNA) sequences were proposed before identifying a strategy for targeting both mutant and non-mutant Htt genes with no apparent detrimental effect (see e.g., WO2005105995; WO2008134646 and U.S. Pat. No. 10,174,321, each of which is hereby incorporated by reference in its entirety). A further analogy relates to Parkinson's Disease (PD) which is linked to a hereditary single-point mutation in the α-synuclein (α-syn) gene as well as genetic duplication or triplication of α-syn (Hardy et al., 2010). Some studies targeting α-syn expression revealed RNAi as a potential therapeutic approach to PD, however, conflicting results were reported (Boudreau et al., 2011; Sapru, et al., 2006). Prediction of susceptible off-target domains to inform RNA design, variable in vivo gene silencing efficiencies, and avoiding off-target effects especially where complex gene expression patterns exist, such as in CNS (central nervous system) regions, are just a few of the challenges in choosing an RNA therapeutic.

Therefore, there exists an unmet need for the treatment of epileptic disorders, such as, e.g., TLE (e.g., drug-resistant TLE).

SUMMARY OF THE DISCLOSURE

The disclosure relates to gene therapy targeting an mRNA sequence encoding a GluK2 receptor subunit that can be used to inhibit epileptiform discharges. A siRNA sequence (e.g., SEQ ID NO: 14, 15, 18, or 19) that targets and binds (e.g., hybridizes) to a corresponding region of the human Grik2 mRNA (e.g., SEQ ID NO: 2, 3, 16, or 17) is described, which is efficient in decreasing the expression of GluK2-containing kainate receptors (KARs) in neurons engineered to express the equivalent shRNA or miRNA. Using a tissue culture model of TLE, the examples remarkably demonstrate that viral expression of shRNA or miRNA containing an antisense sequence of the disclosure inhibits the frequency of epileptiform discharges.

While not wishing to be bound to any theory, aberrant recurrent mossy fiber-dentate granule cell (rMF-DGC) synapses, which operate via ectopic GluK2-containing KARs (Epsztein et al., 2005; Artinian et al., 2011, 2015) may play a key role in chronic seizures in TLE (Peret et al., 2014). For example, interictal spikes and ictal events were reduced in transgenic mice lacking the GluK2 subunit, or in the presence of a pharmacological agent inhibiting GluK2/GluK5 receptors (Peret et al., 2014; Crépel and Mulle, 2015). While knockdown or silencing of GluK2 in transgenic animal models designed to test these theories is feasible, designing an inhibitor selective for the GluK2 subunit of the KAR in humans is challenging. The GluK subunits are structurally conserved and their nucleotide coding sequences share significant homologies. The complex gene expression pattern in the brain with respect to homomeric and heteromeric ionotropic and metabotropic glutamate receptors further complicates any therapeutic strategy. In accordance with the disclosure, RNA therapeutics aimed at decreasing the expression of GluK2-containing KARs in neurons are described that can remarkably prevent spontaneous epileptiform discharges in TLE.

In a first aspect, the disclosure provides a recombinant antisense oligonucleotide including a guide sequence that targets a Grik2 mRNA, wherein the guide sequence is a polynucleotide having at least 85% (e.g., at least 90%, 91%, 92%, 93%, 94%, 95%, 96%, 97%, 98%, 99%, or more) sequence identity to the nucleic acid sequence of SEQ ID NO: 14, 15, 18, or 19, particularly wherein the antisense oligonucleotide does not have the nucleic acid sequence of SEQ ID NOS: 1, 2, or 3. In some embodiments, the polynucleotide has at least 90% (e.g., at least 90%, 91%, 92%, 93%, 94%, 95%, 96%, 97%, 98%, 99%, or more) sequence identity to a nucleic acid sequence of SEQ ID NOS: 14, 15, 18, or 19, particularly wherein the antisense oligonucleotide does not have the nucleic acid sequence of SEQ ID NOS: 1, 2, or 3. In another embodiment, the polynucleotide has at least 95% (e.g., at least 95%, 96%, 97%, 98%, 99%, or more) sequence identity to a nucleic acid sequence of SEQ ID NOS: 14, 15, 18, or 19, particularly wherein the antisense oligonucleotide does not have the nucleic acid sequence of SEQ ID NOS: 1, 2, or 3. In another embodiment, the polynucleotide has a nucleic acid sequence of SEQ ID NOS: 14, 15, 18, or 19, particularly wherein the antisense oligonucleotide does not have the nucleic acid sequence of SEQ ID NOS: 1, 2, or 3.

In some embodiments, the antisense oligonucleotide further includes a passenger sequence, wherein the passenger sequence is a polynucleotide having at least 85% (e.g., at least 90%, 91%, 92%, 93%, 94%, 95%, 96%, 97%, 98%, 99%, or more) sequence identity to a nucleic acid sequence of SEQ ID NOs: 2, 3, 16, or 17. In some embodiments, the polynucleotide has at least 90% (e.g., at least 90%, 91%, 92%, 93%, 94%, 95%, 96%, 97%, 98%, 99%, or more) sequence identity to a nucleic acid sequence of SEQ ID NOs: 2, 3, 16, or 17. In some embodiments, the polynucleotide has at least 95% (e.g., at least 95%, 96%, 97%, 98%, 99%, or more) sequence identity to a nucleic acid sequence of SEQ ID NOS: 2, 3, 16, or 17. In some embodiments, the polynucleotide has a nucleic acid sequence of SEQ ID NOS: 2, 3, 16, or 17.

In some embodiments, the guide sequence is fully or partially complementary to the nucleic acid sequence of SEQ ID NOs: 2, 3, 16, or 17.

In some embodiments, the antisense oligonucleotide is capable of reducing the amount of GluK2 containing kainate receptors in neurons.

In another aspect, the disclosure provides an expression vector including a polynucleotide having at least 85% (e.g., at least 90%, 91%, 92%, 93%, 94%, 95%, 96%, 97%, 98%, 99%, or more) sequence identity to the nucleic acid sequence of SEQ ID NOS: 2, 3, 16, or 17, wherein the polynucleotide does not have the nucleic acid sequence of SEQ ID NOs: 1, 2, or 3.

In some embodiments, the expression vector includes an antisense oligonucleotide of the foregoing aspect and embodiments.

In some embodiments, the expression vector is a mammalian, bacterial, or viral vector. In some embodiments, the viral vector is an adeno-associated viral (AAV) vector, lentiviral vector, or retroviral vector. In some embodiments, the viral vector is an AAV vector. In some embodiments, the AAV vector is an AAV9 or AAVrh10 vector. In some embodiments, wherein the AAV vector includes (i) an expression cassette containing a transgene (e.g., a polynucleotide encoding an antisense oligonucleotide of the disclosure) operably linked to one or more regulatory elements and flanked by ITRs, and (ii) an AAV capsid. In some embodiments, the one or more regulatory elements include a promoter sequence, enhancer sequence, transcription termination sequence, and/or polyadenylation signal.

In another aspect, the disclosure provides an expression cassette including a polynucleotide containing: (a) a stem-loop sequence including from 5' to 3': (i) a 5' stem-loop arm comprising a guide sequence having a nucleic acid sequence of SEQ ID NOS: 14, 15, 18, or 19 or a variant thereof having at least 85% (e.g., at least 90%, 91%, 92%, 93%, 94%, 95%, 96%, 97%, 98%, 99%, or more) sequence identity to the nucleic acid sequence of SEQ ID NOS: 14, 15, 18, or 19, particularly wherein the variant does not have the nucleic acid sequence of SEQ ID NOS: 1, 2, or 3; (ii) a loop sequence, such as, e.g., a microRNA (miR) loop sequence (e.g., a miR-30 loop sequence, such as, e.g., a human, non-human primate, rat, or mouse miR-30 loop sequence); and (iii) a 3' stem-loop arm including a passenger sequence having a nucleic acid sequence of SEQ ID NOs: 2, 3, 16, or 17 or a variant there of having at least 85% (e.g., at least 90%, 91%, 92%, 93%, 94%, 95%, 96%, 97%, 98%, 99%, or more) sequence identity to the nucleic acid sequence of SEQ ID NOS: 2, 3, 16, or 17; (b) a first flanking region located 5' to the guide sequence; and (c) a second flanking region located 3' to the passenger sequence.

In some embodiments, the stem-loop sequence includes a polynucleotide having at least 85% (e.g., at least 90%, 91%, 92%, 93%, 94%, 95%, 96%, 97%, 98%, 99%, or more) sequence identity to the nucleic acid sequence of SEQ ID NO: 20.

In some embodiments, the expression cassette includes a polynucleotide having at least 85% (e.g., at least 90%, 91%, 92%, 93%, 94%, 95%, 96%, 97%, 98%, 99%, or more) sequence identity to the nucleic acid sequence of SEQ ID NO: 21.

In another aspect, the disclosure provides an expression cassette including a polynucleotide containing: (a) a stem-loop sequence including from 5' to 3': (i) a 5' stem-loop arm comprising a passenger sequence having a nucleic acid sequence of SEQ ID NOs: 2, 3, 16, or 17 or a variant thereof having at least 85% (e.g., at least 90%, 91%, 92%, 93%, 94%, 95%, 96%, 97%, 98%, 99%, or more) sequence identity to the nucleic acid sequence of SEQ ID NOs: 2, 3, 16, or 17; (ii) a loop sequence, such as, e.g., a miR loop sequence (e.g., a miR-30 loop sequence, such as, e.g., a human, non-human primate, rat, or mouse miR-30 loop sequence); and; and (iii) a 3' stem-loop arm comprising guide sequence having a nucleic acid sequence of SEQ ID NOs: 14, 15, 18, or 19 or a variant there of having at least 85% (e.g., at least 90%, 91%, 92%, 93%, 94%, 95%, 96%, 97%, 98%, 99%, or more) sequence identity to the nucleic acid sequence of SEQ ID NOs: 14, 15, 18, or 19, particularly wherein the variant does not have the nucleic acid sequence of SEQ ID NOS: 1, 2 or 3; (b) a first flanking region located 5' to the guide sequence; and (c) a second flanking region located 3' to the passenger sequence.

In some embodiments, the stem-loop sequence includes a polynucleotide having at least 85% (e.g., at least 90%, 91%, 92%, 93%, 94%, 95%, 96%, 97%, 98%, 99%, or more) sequence identity to the nucleic acid sequence of SEQ ID NO: 22.

In some embodiments, the expression cassette includes a polynucleotide having at least 85% (e.g., at least 90%, 91%, 92%, 93%, 94%, 95%, 96%, 97%, 98%, 99%, or more) sequence identity to the nucleic acid sequence of SEQ ID NO: 23.

In some embodiments, the first flanking region and the second flanking regions are miR-30 flanking regions. In some embodiments, the first flanking region comprises a polynucleotide having at least 85% (e.g., at least 90%, 91%, 92%, 93%, 94%, 95%, 96%, 97%, 98%, 99%, or more) sequence identity to the nucleic acid sequence of SEQ ID NO: 24. In some embodiments, the second flanking region comprises a polynucleotide having at least 85% (e.g., at least 90%, 91%, 92%, 93%, 94%, 95%, 96%, 97%, 98%, 99%, or more) sequence identity to the nucleic acid sequence of SEQ ID NO: 26.

In some embodiments, the miR-30 loop sequence comprises a polynucleotide having at least 70% (e.g., at least 75%, 80%, 85%, 90%, 91%, 92%, 93%, 94%, 95%, 96%, 97%, 98%, 99%, or more) sequence identity to the nucleic acid sequence of SEQ ID NO: 25.

In some embodiments, the passenger sequence is fully or partially complementary to the guide sequence.

In some embodiment, the expression cassette includes a promoter. In some embodiments, the promoter is a Pol II, Pol III, or a neuron-specific promoter. In some embodiments, the promoter is a human synapsin (hSyn) promoter (e.g., SEQ ID NO: 27 or SEQ ID NO: 28), calcium/ calmodulin-dependent protein kinase II (CaMKII) promoter (e.g., any one of SEQ ID NOs: 30-34), U6 promoter (e.g., SEQ ID NO: 29), or CAG promoter (e.g., SEQ ID NO: 35).

In another aspect, the present disclosure provides a pharmaceutical composition including the antisense oligonucleotide of the foregoing aspects and embodiments, the expression vector of the foregoing aspects and embodiments, or the expression cassette of the foregoing aspects and embodiments, wherein the pharmaceutical composition further includes a pharmaceutically acceptable carrier, excipient, or diluent. In some embodiments, the pharmaceutical composition is for use in treating a disorder in a subject in need thereof.

In some embodiments, the disorder is an epilepsy. In some embodiments, the epilepsy is temporal lobe epilepsy, a chronic epilepsy, and/or a drug-resistant (i.e., refractory) epilepsy. In some embodiments, the subject is a human.

In another aspect, the disclosure provides a method for treating a disorder in a subject in need thereof, the method including administering an effective amount of at least one antisense oligonucleotide of the foregoing aspects and embodiments, the expression vector of the foregoing aspects and embodiments, or the expression cassette of the foregoing aspects and embodiments, or the pharmaceutical composition of the foregoing aspect and embodiments.

In some embodiments, the disorder is an epilepsy. In some embodiments, the epilepsy is temporal lobe epilepsy, a chronic epilepsy, and/or a drug-resistant epilepsy. In some embodiments, the subject is a human.

DETAILED DESCRIPTION

The present disclosure is based, in part, on the inventors' discovery that gene therapy targeting the GluK2 subunit can be used to inhibit epileptiform discharges. They have identified an RNAi sequence against the human Grik2 gene sequence (e.g., SEQ ID NOS: 2, 3, 16, or 17), which is efficient in decreasing the expression of GluK2-containing kainate receptors in neurons infected with the equivalent shRNA or miRNA. Using an in vitro model recapitulating epileptic network in the hippocampus as described in TLE, they demonstrate that viral expression of shRNA or miRNA inhibits the frequency of epileptiform discharges.

Inhibitory Nucleic Acid Sequences

Accordingly, an object of the present disclosure relates to isolated, synthetic or recombinant antisense oligonucleotide targeting Grik2 gene. The oligonucleotide of the disclosure may be of any suitable type.

In some embodiments, the oligonucleotide is an RNA oligonucleotide. In some embodiments, the oligonucleotide is a DNA oligonucleotide.

The term "about" refers to an amount that is ±10% of the recited value and may be ±5% of the recited value or ±2% of the recited value.

The term "nucleotide" is defined as a modified or naturally occurring deoxyribonucleotide or ribonucleotide. Nucleotides typically include purines and pyrimidines, which include thymidine, cytidine, guanosine, adenosine and uridine. The term "oligonucleotide" is defined as an oligomer of the nucleotides defined above. The term "oligonucleotide" refers to a nucleic acid sequence, 3'-5' or 5'-3' oriented, which may be single- or double-stranded. The oligonucleotide used in the context of the disclosure may in particular be DNA or RNA. The term also includes "oligonucleotide analog" which refers to an oligonucleotide having (i) a modified backbone structure, e.g., a backbone other than the standard phosphodiester linkage found in natural oligo-and polynucleotides, and (ii) optionally, modified sugar moieties, e.g., morpholino moieties rather than ribose or deoxyribose moieties. Oligonucleotide analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Particularly, analogs are those having a substantially uncharged, phosphorus containing backbone. A substantially uncharged, phosphorus containing backbone in an oligonucleotide analog is one in which a majority of the subunit linkages, e.g., between 50-100%, typically at least 60% to 100% or 75% or 80% of its linkages, are uncharged, and contain a single phosphorous atom.

The term "oligonucleotide" also refers to an oligonucleotide sequence that is inverted relative to its normal orientation for transcription and so corresponds to an RNA or DNA sequence that is complementary to a target gene mRNA molecule expressed within the host cell (e.g., it can hybridize to the target gene mRNA molecule through Watson-Crick base pairing).

An antisense strand may be constructed in a number of different ways, provided that it is capable of interfering with the expression of a target gene. For example, the antisense strand can be constructed by reverse-complementing the coding region (or a segment thereof) of the target gene relative to its normal orientation for transcription to allow the transcription of its complement, (e.g., RNAs encoded by the antisense and sense gene may be complementary). In some embodiments, the oligonucleotide need not have the same intron or exon pattern as the target gene, and noncoding segments of the target gene may be equally effective in achieving antisense suppression of target gene expression as coding segments such as antisense oligonucleotide (ASO). In some embodiments, the oligonucleotide has the same exon pattern as the target gene such as siRNA and antisense oligonucleotide (ASO).

The terms, "guide strand," or "guide sequence" refer to a component of a stem-loop RNA structure/sequence (e.g., an shRNA or microRNA) or its DNA equivalent positioned on either the 5' or the 3' stem-loop arm, also referred to as the −5p or −3p arm, of the stem-loop structure/sequence, in which the guide strand/sequence includes a Grik2 mRNA antisense sequence (e.g., SEQ ID NOs: 14, 15, 18, or 19 or a variant thereof with at least 85% (e.g., at least 90%, 95%, 96%, 97%, 98%, 99%, or more) sequence identity to the nucleic acid sequence of SEQ ID NOS: 14, 15, 18, or 19) that is capable of binding (e.g., hybridizing) to a Grik2 mRNA and inhibiting the expression of a GluK2 protein. The antisense oligonucleotide does not have the nucleic acid sequence of SEQ ID NOS: 1, 2, or 3. Without wishing to be bound by any theory, inhibition of expression of the GluK2 protein may occur as a result of diverse cellular mechanisms, such as, e.g., mRNA degradation or translational repression. The guide sequence may be complementary to or substantially complementary (e.g., having no more than 5, 4, 3, 2, or 1 mismatches) to a passenger strand/sequence of the stem-loop RNA structure or its DNA equivalent.

The terms "passenger strand" and "passenger sequence" refer to a component of a stem-loop RNA structure/sequence (e.g., an shRNA or microRNA) or its DNA equivalent positioned on either the 5' or the 3' stem-loop arm, also referred to as the −5p or −3p arm, of the stem-loop structure/sequence that includes a sequence complementary to or substantially complementary (e.g., having no more than 5, 4, 3, 2, or 1 mismatches) to Grik2 mRNA antisense sequence (e.g., SEQ ID NOs: 14, 15, 18, or 19 or a variant thereof with at least 85% (e.g., at least 90%, 95%, 96%, 97%, 98%, 99%, or more) sequence identity to the nucleic acid sequence of SEQ ID NOS: 14, 15, 18, or 19). The passenger sequence may be complementary to or substantially complementary (e.g., having no more than 5, 4, 3, 2, or 1 mismatches) to a guide strand/sequence of the stem-loop RNA structure or its DNA equivalent.

The term "target" or "targeting" refers to an oligonucleotide able to specifically bind (e.g., hybridize) to a Grik2 gene or a Grik2 mRNA encoding a Grik2 gene product. In particular, it refers to an oligonucleotide able to inhibit said gene or said mRNA by the methods known to the skilled in the art (e.g., antisense, RNA interference).

The term "corresponding region" refers to a target region of a Grik2 mRNA that is substantially complementary (e.g., having no more than 5, such as, e.g., no more than 4, 3, 2, or 1 mismatches) with the antisense oligonucleotide of the disclosure. Accordingly, a corresponding region of a Grik2 mRNA (e.g., any one of SEQ ID NOs: 2, 3, 16, or 17) refers to a region that is targeted and bound by the antisense oligonucleotide of the disclosure (e.g., oligonucleotide encoded by any one of SEQ ID NOs: 14, 15, 18, or 19).

The term "stem-loop" (also known as a hairpin or hairpin loop) refers to a secondary RNA structure containing a "stem" and a "loop region." The stem region is formed by hybridization of two regions of the same RNA strand (e.g., two stem-loop arms, such as, e.g., a 5' stem-loop arm and a 3' stem-loop arm) via complementary base pairing. The "loop" region corresponds to a short (e.g., 3-8 bp) RNA sequence that covalently links the 3' end of the 5' stem-loop arm and the 5' end of the 3' stem-loop arm. Generally, the loop region is excised within a cell by the endonuclease Dicer to form a stem structure containing only the 5' stem-loop arm and the 3' stem-loop arm. Within the context of the present disclosure, the term "stem-loop" may refer to the secondary RNA structure described above or an RNA or cDNA sequence encoding the same.

The term "stem-loop arm" refers to an RNA sequence that forms part of the stem region of a stem-loop structure by complementary base pairing with a second stem-loop arm. In the context of the present disclosure, the stem-loop arm may comprise a guide sequence or a passenger sequence disclosed herein.

According to the disclosure, the antisense oligonucleotide of the present disclosure targets an mRNA encoding Grik2 gene product and is capable of reducing the amount of Grik2 expression in cells.

That is to say, the antisense oligonucleotide comprises a sequence that is at least partially complementary, particularly perfectly complementary, to a region of the sequence of said mRNA, said complementarity being sufficient to yield specific binding (e.g., hybridization) under intra-cellular conditions. As immediately apparent to the skilled in the art, by a sequence that is "perfectly complementary to" a second sequence is meant the reverse complement counterpart of the second sequence, either under the form of a DNA molecule or under the form of an RNA molecule. A sequence is "partially complementary to" a second sequence if there are one or more mismatches. The antisense oligonucleotide of the present disclosure that targets an mRNA encoding GluK2 receptor subunit (e.g., GluK2 protein comprising any one of SEQ ID NO: 4, SEQ ID NO: 5, SEQ ID NO: 6, SEQ ID NO: 7, SEQ ID NO: 8, SEQ ID NO: 9 or SEQ ID NO: 10, or GluK2 protein comprising at least amino acids 1 to 509 of SEQ ID NO: 4) may be designed by using the sequence of said mRNA as a basis, e.g., using bioinformatic tools. GluK2 (Grik2) mRNA sequences may be found in NCBI Gene ID NO: 2898. In another example, a polynucleotide sequence encoding SEQ ID NO: 4, a polynucleotide sequence encoding contiguous amino acids 1 to 509 of SEQ ID NO: 4, or a polynucleotide sequence encoding the GluK2 amino acid sequence of any one of SEQ ID NO: 4 (UniProtKB Q13002-1), SEQ ID NO: 5 (UniProtKB Q13002-2), SEQ ID NO: 6 (UniProtKB Q13002-3), SEQ ID NO: 7 (UniProtKB Q13002-4), SEQ ID NO: 8 (UniProtKB Q13002-5), SEQ ID NO: 9 (UniProtKB Q13002-6) and SEQ ID NO: 10 (UniProtKB Q13002-7) can be used as a basis for designing nucleic acids that target an mRNA encoding GluK2 receptor. Polynucleotide sequences encoding GluK2 receptor may be selected from SEQ ID NO: 11, SEQ ID NO: 12 and/or SEQ ID NO: 13.

```
>(UniProt Q13002-1; GRIK2_HUMAN Glutamate receptor ionotropic, kainate 2)
                                                                (SEQ ID NO: 4)
MKIIFPILSNPVFRRTVKLLLCLLWIGYSQGTTHVLRFGGIFEYVESGPMGAEELAFRFAVNTINRNRTLLPNTTLTY

DTQKINLYDSFEASKKACDQLSLGVAAIFGPSHSSSANAVQSICNALGVPHIQTRWKHQVSDNKDSFYVSLYPDF

SSLSRAILDLVQFFKWKTVTVVYDDSTGLIRLQELIKAPSRYNLRLKIRQLPADTKDAKPLLKEMKRGKEFHVIFDC

SHEMAAGILKQALAMGMMTEYYHYIFTTLDLFALDVEPYRYSGVNMTGFRILNTENTQVSSIIEKWSMERLQAPP

KPDSGLLDGFMTTDAALMYDAVHVVSVAVQQFPQMTVSSLQCNRHKPWRFGTRFMSLIKEAHWEGLTGRITFN

KTNGLRTDFDLDVISLKEEGLEKIGTWDPASGLNMTESQKGK

PANITDSLSNRSLIVTTILEEPYVLFKKSDKPLYGNDRFEGYCIDLLRELSTILGFTYEIRLVEDGKYGAQDDANGQ

WNGMVRELIDHKADLAVAPLAITYVREKVIDFSKPFMTLGISILYRKPNGTNPGVFSFLNPLSPDIWMYILLAYLGV

SCVLFVIARFSPYEWYNPHPCNPDSDVVENNFTLLNSFWFGVGALMQQGSELMPKALSTRIVGGIWWFFTLIIIS

SYTANLAAFLTVERMESPIDSADDLAKQTKIEYGAVEDGATMTFFKKSKISTYDKMWAFMSSRRQSVLVKSNEE

GIQRVLTSDYAFLMESTTIEFVTQRNCNLTQIGGLIDSKGYGVGTPMGSPYRDKITIAILQLQEEGKLHMMKEKW

WRGNGCPEEESKEASALGVQNIGGIFIVLAAGLVLSVFVAVGEFLYKSKKNAQLEKRSFCSAMVEELRMSLKCQ

RRLKHKPQAPVIVKTEEVINMHTFNDRRLPGKETMA
```

-continued

>(UniProt Q13002-2; GRIK2_HUMAN Isoform 2 of Glutamate receptor ionotropic, kainate 2)
(SEQ ID NO: 5)

MKIIFPILSNPVFRRTVKLLLCLLWIGYSQGTTHVLRFGGIFEYVESGPMGAEELAFRFAVNTINRNRTLLPNTTLTY

DTQKINLYDSFEASKKACDQLSLGVAAIFGPSHSSSANAVQSICNALGVPHIQTRWKHQVSDNKDSFYVSLYPDF

SSLSRAILDLVQFFKWKTVTVVYDDSTGLIRLQELIKAPSRYNLRLKIRQLPADTKDAKPLLKEMKRGKEFHVIFDC

SHEMAAGILKQALAMGMMTEYYHYIFTTLDLFALDVEPYRYSGVNMTGFRILNTENTQVSSIIEKWSMERLQAPP

KPDSGLLDGFMTTDAALMYDAVHVVSVAVQQFPQMTVSSLQCNRHKPWRFGTRFMSLIKEAHWEGLTGRITFN

KTNGLRTDFDLDVISLKEEGLEKIGTWDPASGLNMTESQKGKPANITDSLSNRSLIVTTILEEPYVLFKKSDKPLYG

NDRFEGYCIDLLRELSTILGFTYEIRLVEDGKYGAQDDANGQWNGMVRELIDHKADLAVAPLAITYVREKVIDFSK

PFMTLGISILYRKPNGTNPGVFSFLNPLSPDIWMYILLAYLGVSCVLFVIARFSPYEWYNPHPCNPDSDVVENNFT

LLNSFWFGVGALMQQGSELMPKALSTRIVGGIWWFFTLIIISSYTANLAAFLTVERMESPIDSADDLAKQTKIEYGA

VEDGATMTFFKKSKISTYDKMWAFMSSRRQSVLVKSNEEGIQRVLTSDYAFLMESTTIEFVTQRNONLTQIGGLI

DSKGYGVGTPMGSPYRDKITIAILQLQEEGKLHMMKEKWWRGNGCPEEESKEASALGVQNIGGIFIVLAAGLVLS

VFVAVGEFLYKSKKNAQLEKESSIWLVPPYHPDTV

>(UniProt Q13002-3; GRIK2_HUMAN Isoform 3 of Glutamate receptor ionotropic, kainate 2)
(SEQ ID NO: 6)

MKIIFPILSNPVFRRTVKLLLCLLWIGYSQGTTHVLRFGGIFEYVESGPMGAEELAFRFAVNTINRNRTLLPNTTLTY

DTQKINLYDSFEASKKACDQLSLGVAAIFGPSHSSSANAVQSICNALGVPHIQTRWKHQVSDNKDSFYVSLYPDF

SSLSRAILDLVQFFKWKTVTVVYDDSTGLIRLQELIKAPSRYNLRLKIRQLPADTKDAKPLLKEMKRGKEFHVIFDC

SHEMAAGILKQALAMGMMTEYYHYIFTTLDLFALDVEPYRYSGVNMTGFRILNTENTQVSSIIEKWSMERLQAPP

KPDSGLLDGFMTTDAALMYDAVHVVSVAVQQFPQMTVSSLQCNRHKPWRFGTRFMSLIKEAHWEGLTGRITFN

KTNGLRTDFDLDVISLKEEGLEKIGTWDPASGLNMTESQKGKPANITDSLSNRSLIVTTILEEPYVLFKKSDKPLYG

NDRFEGYCIDLLRELSTILGFTYEIRLVEDGKYGAQDDANGQWNGMVRELIDHKADLAVAPLAITYVREKVIDFSK

PFMTLGISILYRKPNGTNPGVFSFLNPLSPDIWMYILLAYLGVSCVLFVIARF

>(UniProt Q13002-4; GRIK2_HUMAN Isoform 4 of Glutamate receptor ionotropic, kainate 2)
(SEQ ID NO: 7)

MKIIFPILSNPVFRRTVKLLLCLLWIGYSQGTTHVLRFGGIFEYVESGPMGAEELAFRFAVNTINRNRTLLPNTTLTY

DTQKINLYDSFEASKKACDQLSLGVAAIFGPSHSSSANAVQSICNALGVPHIQTRWKHQVSDNKDSFYVSLYPDF

SSLSRAILDLVQFFKWKTVTVVYDDSTGLIRLQELIKAPSRYNLRLKIRQLPADTKDAKPLLKEMKRGKEFHVIFDC

SHEMAAGILKQALAMGMMTEYYHYIFTTLDLFALDVEPYRYSGVNMTGFRILNTENTQVSSIIEKWSMERLQAPP

KPDSGLLDGFMTTDAALMYDAVHVVSVAVQQFPQMTVSSLQCNRHKPWRFGTRFMSLIKEAHWEGLTGRITFN

KTNGLRTDFDLDVISLKEEGLEKIGTWDPASGLNMTESQKGKPANITDSLSNRSLIVTTILEEPYVLFKKSDKPLYG

NDRFEGYCIDLLRELSTILGFTYEIRLVEDGKYGAQDDANGQWNGMVRELIDHKADLAVAPLAITYVREKVIDFSK

PFMTLGISILYRKPNGSELMPKALSTRIVGGIWWFFTLIIISSYTANLAAFLTVERMESPIDSADDLAKQTKIEYGAV

EDGATMTFFKKSKISTYDKMWAFMSSRRQSVLVKSNEEGIQRVLTSDYAFLMESTTIEFVTQRNCNLTQIGGLID

SKGYGVGTPMGSPYRDKITIAILQLQEEGKLHMMKEKWWRGNGCPEEESKEASALGVQNIGGIFIVLAAGLVLSV

FVAVGEFLYKSKKNAQLEKRSFCSAMVEELRMSLKCQRRLKHKPQAPVIVKTEEVINMHTFNDRRLPGKETMA

>(UniProt Q13002-5; GRIK2_HUMAN Isoform 5 of Glutamate receptor ionotropic, kainate 2)
(SEQ ID NO: 8)

MKIIFPILSNPVFRRTVKLLLCLLWIGYSQGTTHVLRFGGIFEYVESGPMGAEELAFRFAVNTINRNRTLLPNTTLTY

DTQKINLYDSFEASKKACDQLSLGVAAIFGPSHSSSANAVQSICNALGVPHIQTRWKHQVSDNKDSFYVSLYPDF

SSLSRAILDLVQFFKWKTVTVVYDDSTGLIRLQELIKAPSRYNLRLKIRQLPADTKDAKPLLKEMKRGKEFHVIFDC

SHEMAAGILKQALAMGMMTEYYHYIFTTLDLFALDVEPYRYSGVNMTGFRILNTENTQVSSIIEKWSMERLQAPP

KPDSGLLDGFMTTDAALMYDAVHVVSVAVQQFPQMTVSSLQCNRHKPWRFGTRFMSLIKEAHWEGLTGRITFN

KTNGLRTDFDLDVISLKEEGLEKIGTWDPASGLNMTESQKGKPANITDSLSNRSLIVTTILEEPYVLFKKSDKPLYG

-continued

NDRFEGYCIDLLRELSTILGFTYEIRLVEDGKYGAQDDANGQWNGMVRELIDHKADLAVAPLAITYVREKVIDFSK

PFMTLGISILYRKPNGTNPGVFSFLNPLSPDIWMYILLAYLGVSCVLFVIARFSPYEWYNPHPCNPDSDVVENNFT

LLNSFWFGVGALMQQGSELMPKALSTRIVGGIWWFFTLIIISSYTANLAAFLTVERMESPIDSADDLAKQTKIEYGA

VEDGATMTFFKKSKISTYDKMWAFMSSRRQSVLVKSNEEGIQRVLTSDYAFLMESTTIEFVTQRNCNLTQIGGLI

DSKGYGVGTPMGSPYRDKITIAILQLQEEGKLHMMKEKWWRGNGCPEEESKEASALGVQNIGGIFIVLAAGLVLS

VFVAVGEFLYKSKKNAQLEKRAKTKLPQDYVFLPILESVSISTVLSSSPSSSSLSSCS

>(UniProt Q13002-6; GRIK2_HUMAN Isoform 6 of Glutamate receptor ionotropic, kainate 2)
(SEQ ID NO: 9)

MKIIFPILSNPVFRRTVKLLLCLLWIGYSQGTTHVLRFGGIFEYVESGPMGAEELAFRFAVNTINRNRTLLPNTTLTY

DTQKINLYDSFEASKKACDQLSLGVAAIFGPSHSSSANAVQSICNALGVPHIQTRWKHQVSDNKDSFYVSLYPDF

SSLSRAILDLVQFFKWKTVTVVYDDSTGLIRLQELIKAPSRYNLRLKIRQLPADTKDAKPLLKEMKRGKEFHVIFDC

SHEMAAGILKQALAMGMMTEYYHYIFTTLDLFALDVEPYRYSGVNMTGFRILNTENTQVSSIIEKWSMERLQAPP

KPDSGLLDGFMTTDAALMYDAVHVVSVAVQQFPQMTVSSLQCNRHKPWRFGTRFMSLIKEAHWEGLTGRITFN

KTNGLRTDFDLDVISLKEEGLEKIGTWDPASGLNMTESQKGKPANITDSLSNRSLIVTTILEEPYVLFKKSDKPLYG

NDRFEGYCIDLLRELSTILGFTYEIRLVEDGKYGAQDDANGQWNGMVRELIDHKSKISTYDKMWAFMSSRRQSV

LVKSNEEGIQRVLTSDYAFLMESTTIEFVTQRNCNLTQIGGLIDSKGYGVGTPMGSPYRDKITIAILQLQEEGKLHM

MKEKWWRGNGCPEEESKEASALGVQNIGGIFIVLAAGLVLSVFVAVGEFLYKSKKNAQLEKESSIWLVPPYHPDT

V

>(UniProt Q13002-7; GRIK2_HUMAN Isoform 7 of Glutamate receptor ionotropic, kainate 2)
(SEQ ID NO: 10)

MKIIFPILSNPVFRRTVKLLLCLLWIGYSQGTTHVLRFGGIFEYVESGPMGAEELAFRFAVNTINRNRTLLPNTTLTY

DTQKINLYDSFEASKKACDQLSLGVAAIFGPSHSSSANAVQSICNALGVPHIQTRWKHQVSDNKDSFYVSLYPDF

SSLSRAILDLVQFFKWKTVTVVYDDSTGLIRLQELIKAPSRYNLRLKIRQLPADTKDAKPLLKEMKRGKEFHVIFDC

SHEMAAGILKQALAMGMMTEYYHYIFTTLDLFALDVEPYRYSGVNMTGFRILNTENTQVSSIIEKWSMERLQAPP

KPDSGLLDGFMTTDAALMYDAVHVVSVAVQQFPQMTVSSLQCNRHKPWRFGTRFMSLIKEAHWEGLTGRITFN

KTNGLRTDFDLDVISLKEEGLEKIGTWDPASGLNMTESQKGKPANITDSLSNRSLIVTTILEEPYVLFKKSDKPLYG

NDRFEGYCIDLLRELSTILGFTYEIRLVEDGKYGAQDDANGQWNGMVRELIDHKSVLVKSNEEGIQRVLTSDYAF

LMESTTIEFVTQRNCNLTQIGGLIDSKGYGVGTPMGSPYRDKITIAILQLQEEGKLHMMKEKWWRGNGCPEEES

KEASALGVQNIGGIFIVLAAGLVLSVFVAVGEFLYKSKKNAQLEKRAKTKLPQDYVFLPILESVSISTVLSSSPSSSS

LSSCS

>(RefSeq NM_021956.4:294-3020 Homo sapiens glutamate ionotropic receptor kainate type subunit 2 (GRIK2), transcript variant 1, mRNA)
(SEQ ID NO: 11)

ATGAAGATTATTTTCCCGATTCTAAGTAATCCAGTCTTCAGGCGCACCGTTAAACTCCTGCTCTGTTTACTGT

GGATTGGATATTCTCAAGGAACCACACATGTATTAAGATTTGGTGGTATTTTTGAATATGTGGAATCTGGCCC

AATGGGAGCTGAGGAACTTGCATTCAGATTTGCTGTGAACACAATTAACAGAAACAGAACATTGCTACCCAA

TACTACCCTTACCTATGATACCCAGAAGATAAACCTTTATGATAGTTTTGAAGCATCCAAGAAAGCCTGTGAT

CAGCTGTCTCTTGGGGTGGCTGCCATCTTCGGGCCTTCACACAGCTCATCAGCAAACGCAGTGCAGTCCAT

CTGCAATGCTCTGGGAGTTCCCCACATACAGACCCGCTGGAAGCACCAGGTGTCAGACAACAAAGATTCCT

TCTATGTCAGTCTCTACCCAGACTTCTCTTCACTCAGCCGTGCCATTTTAGACCTGGTGCAGTTTTTCAAGTG

GAAAACCGTCACGGTTGTGTATGATGACAGCACTGGTCTCATTCGTTTGCAAGAGCTCATCAAAGCTCCATC

AAGGTATAATCTTCGACTCAAAATTCGTCAGTTACCTGCTGATACAAAGGATGCAAAACCCTTACTAAAAGAA

ATGAAAAGAGGCAAGGAGTTTCATGTAATCTTTGATTGTAGCCATGAAATGGCAGCAGGCATTTTAAAACAG

GCATTAGCTATGGGAATGATGACAGAATACTATCATTATATCTTTACCACTCTGGACCTCTTTGCTCTTGATG

-continued

TTGAGCCCTACCGATACAGTGGTGTTAACATGACAGGGTTCAGAATATTAAATACAGAAAATACCCAAGTCT

CCTCCATCATTGAAAAGTGGTCGATGGAACGATTGCAGGCACCTCCGAAACCCGATTCAGGTTTGCTGGAT

GGATTTATGACGACTGATGCTGCTCTAATGTATGATGCTGTGCATGTGGTGTCTGTGGCCGTTCAACAGTTT

CCCCAGATGACAGTCAGTTCCTTGCAGTGTAATCGACATAAACCCTGGCGCTTCGGGACCCGCTTTATGAG

TCTAATTAAAGAGGCACATTGGGAAGGCCTCACAGGCAGAATAACTTTCAACAAAACCAATGGCTTGAGAAC

AGATTTTGATTTGGATGTGATCAGTCTGAAGGAAGAAGGTCTAGAAAAGATTGGAACGTGGGATCCAGCCA

GTGGCCTGAATATGACAGAAAGTCAAAAGGGAAAGCCAGCGAACATCACAGATTCCTTATCCAATCGTTCTT

TGATTGTTACCACCATTTTGGAAGAGCCTTATGTCCTTTTTAAGAAGTCTGACAAACCTCTCTATGGTAATGA

TCGATTTGAAGGCTATTGCATTGATCTCCTCAGAGAGTTATCTACAATCCTTGGCTTTACATATGAAATTAGA

CTTGTGGAAGATGGGAAATATGGAGCCCAGGATGATGCCAATGGACAATGGAATGGAATGGTTCGTGAACT

AATTGATCATAAAGCTGACCTTGCAGTTGCTCCACTGGCTATTACCTATGTTCGAGAGAAGGTCATCGACTT

TTCCAAGCCCTTTATGACACTTGGAATAAGTATTTTGTACCGCAAGCCCAATGGTACAAACCCAGGCGTCTT

CTCCTTCCTGAATCCTCTCTCCCCTGATATCTGGATGTATATTCTGCTGGCTTACTTGGGTGTCAGTTGTGT

GCTCTTTGTCATAGCCAGGTTTAGTCCTTATGAGTGGTATAATCCACACCCTTGCAACCCTGACTCAGACGT

GGTGGAAAACAATTTTACCTTGCTAAATAGTTTCTGGTTTGGAGTTGGAGCTCTCATGCAGCAAGGTTCTGA

GCTCATGCCCAAAGCACTGTCCACCAGGATAGTGGGAGGCATTTGGTGGTTTTTCACACTTATCATCATTTC

TTCGTATACTGCTAACTTAGCCGCCTTTCTGACAGTGGAACGCATGGAATCCCCTATTGACTCTGCTGATGA

TTTAGCTAAACAAACCAAGATAGAATATGGAGCAGTAGAGGATGGTGCAACCATGACTTTTTTCAAGAAATC

AAAAATCTCCACGTATGACAAAATGTGGGCCTTTATGAGTAGCAGAAGGCAGTCAGTGCTGGTCAAAAGTAA

TGAAGAAGGAATCCAGCGAGTCCTCACCTCTGATTATGCTTTCCTAATGGAGTCAACAACCATCGAGTTTGT

TACCCAGCGGAACTGTAACCTGACACAGATTGGCGGCCTTATAGACTCTAAAGGTTATGGCGTTGGCACTC

CCATGGGTTCTCCATATCGAGACAAAATTACCATAGCAATTCTTCAGCTGCAAGAGGAAGGCAAACTGCATA

TGATGAAGGAGAAATGGTGGAGGGGCAATGGTTGCCCAGAAGAGGAGAGCAAAGAGGCCAGTGCCCTGG

GGGTTCAGAATATTGGTGGCATCTTCATTGTTCTGGCAGCCGGCTTGGTGCTTTCAGTTTTTGTGGCAGTGG

GAGAATTTTTATACAAATCCAAAAAAAACGCTCAATTGGAAAAGAGGTCCTTCTGTAGTGCCATGGTAGAAG

AATTGAGGATGTCCCTGAAGTGCCAGCGTCGGTTAAAACATAAGCCACAGGCCCCAGTTATTGTGAAAACA

GAAGAAGTTATCAACATGCACACATTTAACGACAGAAGGTTGCCAGGTAAAGAAACCATGGCATAA

>(RefSeq NM_175768.3:294-2903 Homo sapiens glutamate ionotropic receptor kainate type subunit 2 (GRIK2), transcript variant 2, mRNA)

(SEQ ID NO: 12)

ATGAAGATTATTTTCCCGATTCTAAGTAATCCAGTCTTCAGGCGCACCGTTAAACTCCTGCTCTGTTTACTGT

GGATTGGATATTCTCAAGGAACCACACATGTATTAAGATTTGGTGGTATTTTTGAATATGTGGAATCTGGCCC

AATGGGAGCTGAGGAACTTGCATTCAGATTTGCTGTGAACACAATTAACAGAAACAGAACATTGCTACCCAA

TACTACCCTTACCTATGATACCCAGAAGATAAACCTTTATGATAGTTTTGAAGCATCCAAGAAAGCCTGTGAT

CAGCTGTCTCTTGGGGTGGCTGCCATCTTCGGGCCTTCACACAGCTCATCAGCAAACGCAGTGCAGTCCAT

CTGCAATGCTCTGGGAGTTCCCCACATACAGACCCGCTGGAAGCACCAGGTGTCAGACAACAAAGATTCCT

TCTATGTCAGTCTCTACCCAGACTTCTCTTCACTCAGCCGTGCCATTTTAGACCTGGTGCAGTTTTTCAAGTG

GAAAACCGTCACGGTTGTGTATGATGACAGCACTGGTCTCATTCGTTTGCAAGAGCTCATCAAAGCTCCATC

AAGGTATAATCTTCGACTCAAAATTCGTCAGTTACCTGCTGATACAAAGGATGCAAAACCCTTACTAAAAGAA

ATGAAAAGAGGCAAGGAGTTTCATGTAATCTTTGATTGTAGCCATGAAATGGCAGCAGGCATTTTAAAACAG

GCATTAGCTATGGGAATGATGACAGAATACTATCATTATATCTTTACCACTCTGGACCTCTTTGCTCTTGATG

TTGAGCCCTACCGATACAGTGGTGTTAACATGACAGGGTTCAGAATATTAAATACAGAAAATACCCAAGTCT

-continued

CCTCCATCATTGAAAAGTGGTCGATGGAACGATTGCAGGCACCTCCGAAACCCGATTCAGGTTTGCTGGAT

GGATTTATGACGACTGATGCTGCTCTAATGTATGATGCTGTGCATGTGGTGTCTGTGGCCGTTCAACAGTTT

CCCCAGATGACAGTCAGTTCCTTGCAGTGTAATCGACATAAACCCTGGCGCTTCGGGACCCGCTTTATGAG

TCTAATTAAAGAGGCACATTGGGAAGGCCTCACAGGCAGAATAACTTTCAACAAAACCAATGGCTTGAGAAC

AGATTTTGATTTGGATGTGATCAGTCTGAAGGAAGAAGGTCTAGAAAAGATTGGAACGTGGGATCCAGCCA

GTGGCCTGAATATGACAGAAAGTCAAAAGGGAAAGCCAGCGAACATCACAGATTCCTTATCCAATCGTTCTT

TGATTGTTACCACCATTTTGGAAGAGCCTTATGTCCTTTTTAAGAAGTCTGACAAACCTCTCTATGGTAATGA

TCGATTTGAAGGCTATTGCATTGATCTCCTCAGAGAGTTATCTACAATCCTTGGCTTTACATATGAAATTAGA

CTTGTGGAAGATGGGAAATATGGAGCCCAGGATGATGCCAATGGACAATGGAATGGAATGGTTCGTGAACT

AATTGATCATAAAGCTGACCTTGCAGTTGCTCCACTGGCTATTACCTATGTTCGAGAGAAGGTCATCGACTT

TTCCAAGCCCTTTATGACACTTGGAATAAGTATTTTGTACCGCAAGCCCAATGGTACAAACCCAGGCGTCTT

CTCCTTCCTGAATCCTCTCTCCCCTGATATCTGGATGTATATTCTGCTGGCTTACTTGGGTGTCAGTTGTGT

GCTCTTTGTCATAGCCAGGTTTAGTCCTTATGAGTGGTATAATCCACACCCTTGCAACCCTGACTCAGACGT

GGTGGAAAACAATTTTACCTTGCTAAATAGTTTCTGGTTTGGAGTTGGAGCTCTCATGCAGCAAGGTTCTGA

GCTCATGCCCAAAGCACTGTCCACCAGGATAGTGGGAGGCATTTGGTGGTTTTTCACACTTATCATCATTTC

TTCGTATACTGCTAACTTAGCCGCCTTTCTGACAGTGGAACGCATGGAATCCCCTATTGACTCTGCTGATGA

TTTAGCTAAACAAACCAAGATAGAATATGGAGCAGTAGAGGATGGTGCAACCATGACTTTTTTCAAGAAATC

AAAAATCTCCACGTATGACAAAATGTGGGCCTTTATGAGTAGCAGAAGGCAGTCAGTGCTGGTCAAAAGTAA

TGAAGAAGGAATCCAGCGAGTCCTCACCTCTGATTATGCTTTCCTAATGGAGTCAACAACCATCGAGTTTGT

TACCCAGCGGAACTGTAACCTGACACAGATTGGCGGCCTTATAGACTCTAAAGGTTATGGCGTTGGCACTC

CCATGGGTTCTCCATATCGAGACAAAATTACCATAGCAATTCTTCAGCTGCAAGAGGAAGGCAAACTGCATA

TGATGAAGGAGAAATGGTGGAGGGGCAATGGTTGCCCAGAAGAGGAGAGCAAAGAGGCCAGTGCCCTGG

GGGTTCAGAATATTGGTGGCATCTTCATTGTTCTGGCAGCCGGCTTGGTGCTTTCAGTTTTTGTGGCAGTGG

GAGAATTTTTATACAAATCCAAAAAAAACGCTCAATTGGAAAAGGAATCTTCTATTTGGTTAGTGCCACCATA

CCATCCAGACACTGTTTAG

>(RefSeq NM_001166247.1:294-2972 Homo sapiens glutamate ionotropic receptor kainate type
subunit 2 (GRIK2), transcript variant 3, mRNA)

(SEQ ID NO: 13)

ATGAAGATTATTTTCCCGATTCTAAGTAATCCAGTCTTCAGGCGCACCGTTAAACTCCTGCTCTGTTTACTGT

GGATTGGATATTCTCAAGGAACCACACATGTATTAAGATTTGGTGGTATTTTTGAATATGTGGAATCTGGCCC

AATGGGAGCTGAGGAACTTGCATTCAGATTTGCTGTGAACACAATTAACAGAAACAGAACATTGCTACCCAA

TACTACCCTTACCTATGATACCCAGAAGATAAACCTTTATGATAGTTTTGAAGCATCCAAGAAAGCCTGTGAT

CAGCTGTCTCTTGGGGTGGCTGCCATCTTCGGGCCTTCACACAGCTCATCAGCAAACGCAGTGCAGTCCAT

CTGCAATGCTCTGGGAGTTCCCCACATACAGACCCGCTGGAAGCACCAGGTGTCAGACAACAAAGATTCCT

TCTATGTCAGTCTCTACCCAGACTTCTCTTCACTCAGCCGTGCCATTTTAGACCTGGTGCAGTTTTTCAAGTG

GAAAACCGTCACGGTTGTGTATGATGACAGCACTGGTCTCATTCGTTTGCAAGAGCTCATCAAAGCTCCATC

AAGGTATAATCTTCGACTCAAAATTCGTCAGTTACCTGCTGATACAAAGGATGCAAAACCCTTACTAAAAGAA

ATGAAAAGAGGCAAGGAGTTTCATGTAATCTTTGATTGTAGCCATGAAATGGCAGCAGGCATTTTAAAACAG

GCATTAGCTATGGGAATGATGACAGAATACTATCATTATATCTTTACCACTCTGGACCTCTTTGCTCTTGATG

TTGAGCCCTACCGATACAGTGGTGTTAACATGACAGGGTTCAGAATATTAAATACAGAAAATACCCAAGTCT

CCTCCATCATTGAAAAGTGGTCGATGGAACGATTGCAGGCACCTCCGAAACCCGATTCAGGTTTGCTGGAT

-continued

```
GGATTTATGACGACTGATGCTGCTCTAATGTATGATGCTGTGCATGTGGTGTCTGTGGCCGTTCAACAGTTT

CCCCAGATGACAGTCAGTTCCTTGCAGTGTAATCGACATAAACCCTGGCGCTTCGGGACCCGCTTTATGAG

TCTAATTAAAGAGGCACATTGGGAAGGCCTCACAGGCAGAATAACTTTCAACAAAACCAATGGCTTGAGAAC

AGATTTTGATTTGGATGTGATCAGTCTGAAGGAAGAAGGTCTAGAAAAGATTGGAACGTGGGATCCAGCCA

GTGGCCTGAATATGACAGAAAGTCAAAAGGGAAAGCCAGCGAACATCACAGATTCCTTATCCAATCGTTCTT

TGATTGTTACCACCATTTTGGAAGAGCCTTATGTCCTTTTTAAGAAGTCTGACAAACCTCTCTATGGTAATGA

TCGATTTGAAGGCTATTGCATTGATCTCCTCAGAGAGTTATCTACAATCCTTGGCTTTACATATGAAATTAGA

CTTGTGGAAGATGGGAAATATGGAGCCCAGGATGATGCCAATGGACAATGGAATGGAATGGTTCGTGAACT

AATTGATCATAAAGCTGACCTTGCAGTTGCTCCACTGGCTATTACCTATGTTCGAGAGAAGGTCATCGACTT

TTCCAAGCCCTTTATGACACTTGGAATAAGTATTTTGTACCGCAAGCCCAATGGTACAAACCCAGGCGTCTT

CTCCTTCCTGAATCCTCTCTCCCCTGATATCTGGATGTATATTCTGCTGGCTTACTTGGGTGTCAGTTGTGT

GCTCTTTGTCATAGCCAGGTTTAGTCCTTATGAGTGGTATAATCCACACCCTTGCAACCCTGACTCAGACGT

GGTGGAAAACAATTTTACCTTGCTAAATAGTTTCTGGTTTGGAGTTGGAGCTCTCATGCAGCAAGGTTCTGA

GCTCATGCCCAAAGCACTGTCCACCAGGATAGTGGGAGGCATTTGGTGGTTTTTCACACTTATCATCATTTC

TTCGTATACTGCTAACTTAGCCGCCTTTCTGACAGTGGAACGCATGGAATCCCCTATTGACTCTGCTGATGA

TTTAGCTAAACAAACCAAGATAGAATATGGAGCAGTAGAGGATGGTGCAACCATGACTTTTTTCAAGAAATC

AAAAATCTCCACGTATGACAAAATGTGGGCCTTTATGAGTAGCAGAAGGCAGTCAGTGCTGGTCAAAAGTAA

TGAAGAAGGAATCCAGCGAGTCCTCACCTCTGATTATGCTTTCCTAATGGAGTCAACAACCATCGAGTTTGT

TACCCAGCGGAACTGTAACCTGACACAGATTGGCGGCCTTATAGACTCTAAAGGTTATGGCGTTGGCACTC

CCATGGGTTCTCCATATCGAGACAAAATTACCATAGCAATTCTTCAGCTGCAAGAGGAAGGCAAACTGCATA

TGATGAAGGAGAAATGGTGGAGGGGCAATGGTTGCCCAGAAGAGGAGAGCAAAGAGGCCAGTGCCCTGG

GGGTTCAGAATATTGGTGGCATCTTCATTGTTCTGGCAGCCGGCTTGGTGCTTTCAGTTTTTGTGGCAGTGG

GAGAATTTTTATACAAATCCAAAAAAAACGCTCAATTGGAAAAGAGAGCCAAGACTAAGTTACCTCAAGACTA

TGTATTCCTCCCTATTTTGGAGTCAGTTTCCATTTCTACAGTGTTGTCATCATCACCATCTTCATCATCATTAT

CATCATGTTCTTAA
```

Therefore, the present disclosure contemplates antisense oligonucleotides that, when bound to one or more corresponding regions of a Grik2 mRNA, forms a duplex structure with the Grik2 mRNA of that is between 7-25 (e.g., 7, 8, 9, 10, 11, 12, 13, 14, 15, 16, 17, 18, 19, 20, 21, 22, 23, 24, or 25) nucleotides in length. For example, the duplex structure between the antisense oligonucleotide and the Grik2 mRNA may be 7 nucleotides in length. In another example, the duplex structure between the antisense oligonucleotide and the Grik2 mRNA may be 8 nucleotides in length. In another example, the duplex structure between the antisense oligonucleotide and the Grik2 mRNA may be 9 nucleotides in length. In another example, the duplex structure between the antisense oligonucleotide and the Grik2 mRNA may be 10 nucleotides in length. In another example, the duplex structure between the antisense oligonucleotide and the Grik2 mRNA may be 11 nucleotides in length. In another example, the duplex structure between the antisense oligonucleotide and the Grik2 mRNA may be 12 nucleotides in length. In another example, the duplex structure between the antisense oligonucleotide and the Grik2 mRNA may be 13 nucleotides in length. In another example, the duplex structure between the antisense oligonucleotide and the Grik2 mRNA may be 14 nucleotides in length. In another example, the duplex structure between the antisense oligonucleotide and the Grik2 mRNA may be 15 nucleotides in length. In another example, the duplex structure between the antisense oligonucleotide and the Grik2 mRNA may be 16 nucleotides in length. In another example, the duplex structure between the antisense oligonucleotide and the Grik2 mRNA may be 17 nucleotides in length. In another example, the duplex structure between the antisense oligonucleotide and the Grik2 mRNA may be 18 nucleotides in length. In another example, the duplex structure between the antisense oligonucleotide and the Grik2 mRNA may be 19 nucleotides in length. In another example, the duplex structure between the antisense oligonucleotide and the Grik2 mRNA may be 20 nucleotides in length. In another example, the duplex structure between the antisense oligonucleotide and the Grik2 mRNA may be 21 nucleotides in length. In another example, the duplex structure between the antisense oligonucleotide and the Grik2 mRNA may be 22 nucleotides in length. In another example, the duplex structure between the antisense oligonucleotide and the Grik2 mRNA may be 23 nucleotides in length. In another example, the duplex structure between the antisense oligonucleotide and the Grik2 mRNA may be 24 nucleotides in length. In yet another example, the duplex structure between the antisense oligonucleotide and the Grik2 mRNA may be 25 nucleotides in length.

According to the disclosed methods and compositions, the duplex structure formed by an antisense oligonucleotide (e.g., any one of the antisense oligonucleotides disclosed herein, such as, e.g., any one of SEQ ID NOs: 14, 15, 18, or 19 or a variant thereof having at least 85% (at least 86%, 87%, 88%, 89%, 90%, 91%, 92%, 93%, 94%, 95%, 96%, 97%, 98%, 99%, or more, wherein the antisense oligonucleotide does not have the nucleic acid sequence of SEQ ID NOs: 1, 2, or 3) sequence identity to the nucleic acid sequence of any one of SEQ ID NOS: 14, 15, 18, or 19) and one or more corresponding regions of a Grik2 mRNA may include at least one (e.g., at least 1, 2, 3, 4, 5, 6, 7, 8, 9, 10, 11, 12, 13, 14, or 15) mismatch. For example, the duplex structure may contain 1 mismatch. In another example, the duplex structure contains 2 mismatches. In another example, the duplex structure contains 3 mismatches. In another example, the duplex structure contains 4 mismatches. In another example, the duplex structure contains 5 mismatches. In another example, the duplex structure contains 6 mismatches. In another example, the duplex structure contains 7 mismatches. In another example, the duplex structure contains 8 mismatches. In another example, the duplex structure contains 9 mismatches. In another example, the duplex structure contains 10 mismatches. In another example, the duplex structure contains 11 mismatches. In another example, the duplex structure contains 12 mismatches. In another example, the duplex structure contains 13 mismatches. In another example, the duplex structure contains 14 mismatches. In yet another example, the duplex structure contains 15 mismatches.

Particularly, the antisense oligonucleotide according to the disclosure is capable of reducing the amount of GluK2-containing kainate receptors in neurons. Methods for determining whether an oligonucleotide is capable of reducing the amount of GluK2 receptor in cells are known to those skilled in the art. This may for example be done by analyzing Grik2 RNA expression such as by RT-qPCR, in situ hybridization or GluK2 protein expression such as by immunohistochemistry, Western blot, and by comparing GluK2 protein expression or GluK2 functional activity in the presence and in the absence of the antisense oligonucleotide to be tested.

In other embodiments, the oligonucleotide is targeted to a translation initiation site (AUG codon), sequences in the coding region (e.g., one or more exons), 5'-untranslated region or 3'-untranslated region of an mRNA. The aim is to interfere with the processing and expression of the mRNA, such as, e.g., translocation of the mRNA to the site for protein translation, actual translation of protein from the mRNA, splicing or maturation of the pre-mRNA and possible independent catalytic activity which may be performed by the RNA. The overall effect of such interference with the RNA function is to cause interference with protein expression.

In some embodiments, the oligonucleotide of the present disclosure has a length from 15 to 25 nucleotides. In particular, the oligonucleotide of the present disclosure has a length of 16, 17, 18, 19, 20, 21, 22, 23, 24, or 25 nucleotides.

In some embodiments, the oligonucleotide of the present disclosure is further modified, particularly chemically modified, in order to increase the stability and/or therapeutic efficiency in vivo. The one skilled in the art can easily provide some modifications that will improve the efficacy of the oligonucleotide such as stabilizing modifications and modifications avoiding the RNase H activation in order to avoid degradation of the targeted transcript (C. Frank Bennett and Eric E. Swayze, RNA Targeting Therapeutics: Molecular Mechanisms of Antisense Oligonucleotides as a Therapeutic PlatformAnnu. Rev. Pharmacol. Toxicol. 2010.50:259-293; Juliano R L. The delivery of therapeutic oligonucleotides. Nucleic Acids Res. 2016 Aug. 19; 44 (14): 6518-48). In particular, the oligonucleotide used in the context of the disclosure may comprise modified nucleotides. Chemical modifications may occur at three different sites: (i) at phosphate groups, (ii) on the sugar moiety, and/or (iii) on the entire backbone structure of the oligonucleotide. Typically, chemical modifications include backbone modifications, heterocycle modifications, sugar modifications, and conjugation strategies.

For example the oligonucleotide may be selected from the group consisting of oligodeoxyribonucleotides, oligoribonucleotides, small regulatory RNAs (sRNAS), U7-or U1-mediated ASOs or conjugate products thereof such as peptide-conjugated or nanoparticle-complexed ASOs, chemically modified oligonucleotide by backbone modifications such as morpholinos, phosphorodiamidate morpholino oligomers (Phosphorodiamidate morpholinos, PMO), peptide nucleic acid (PNA), phosphorothioate (PS) oligonucleotides, stereochemically pure phosphorothioate (PS) oligonucleotides, phosphoramidates modified oligonucleotides, thiophosphoramidate-modified oligonucleotides, and methylphosphonate modified oligonucleotides; chemically modified oligonucleotide by heterocycle modifications such as bicycle modified oligonucleotides, Bicyclic Nucleic Acid (BNA), tricycle modified oligonucleotides, tricyclo-DNA-antisense oligonucleotides (ASOs), nucleobase modifications such as 5-methyl substitution on pyrimidine nucleobases, 5-substituted pyrimidine analogues, 2-Thio-thymine modified oligonucleotides, and purine modified oligonucleotides; chemically modified oligonucleotide by sugar modifications such as Locked Nucleic Acid (LNA) oligonucleotides, 2',4'-Methyleneoxy Bridged Nucleic Acid (BNA), ethylene-bridged nucleic acid (ENA), constrained ethyl (cEt) oligonucleotides, 2'-Modified RNA, 2'- and 4'-modified oligonucleotides such as 2'-O-Me RNA (2'-OMe), 2'-O-Methoxyethyl RNA (MOE), 2'-Fluoro RNA (FRNA), and 4'-Thio-Modified DNA and RNA; chemically modified oligonucleotide by conjugation strategies such as N-acetyl galactosamine (GalNAc) oligonucleotide conjugates such as 5'-GalNAc and 3'-GalNAc ASO conjugates, lipid oligonucleotide conjugates, cell penetrating peptides (CPP) oligonucleotide conjugates, targeted oligonucleotide conjugates, antibody-oligonucleotide conjugates, polymer-oligonucleotide conjugate such as with PEGylation and targeting ligand; and chemical modifications and conjugation strategies described for example in Bennett and Swayze, 2010 (RNA targeting therapeutics: molecular mechanisms of antisense oligonucleotides as a therapeutic platform. Annu Rev Pharmacol Toxicol. 2010; 50:259-93); Wan and Seth, 2016 (The Medicinal Chemistry of Therapeutic Oligonucleotides. J Med Chem. 2016 Nov. 10; 59 (21): 9645-9667); Juliano, 2016 (The delivery of therapeutic oligonucleotides. Nucleic Acids Res. 2016 Aug. 19; 44 (14): 6518-48); Lundin et al., 2015 (Oligonucleotide Therapies: The Past and the Present. Hum Gene Ther. 2015 August;26 (8): 475-85); and Prakash, 2011 (An overview of sugar-modified oligonucleotides for antisense therapeutics. Chem Biodivers. 2011 September;8 (9): 1616-41). Indeed, for use in vivo, the oligonucleotide may be stabilized. A "stabilized" oligonucleotide refers to an oligonucleotide that is relatively resistant to in vivo degradation (e.g., via an exo- or endonuclease). Stabilization can be a function of length or secondary structure. In particular, oligonucleotide stabilization can be accomplished via phosphate backbone modifications, phosphodiester modifications, phosphorothioate (PS) backbone modifications, combinations of phosphodiester and phosphorothioate modifications, thiophosphoramidate modifications, 2' modifications (2'-O-Me, 2'-O-(2-methoxyethyl) (MOE) modifications and 2'-fluoro modifications), methylphosphonate, methylphosphorothioate, phosphorodithioate, p-ethoxy, and combinations thereof.

For example, the oligonucleotide may be employed as phosphorothioate derivatives (replacement of a non-bridging phosphoryl oxygen atom with a sulfur atom), which have increased resistance to nuclease digestion. 2'-methoxyethyl (MOE) modification (such as the modified backbone commercialized by IONIS Pharmaceuticals) is also effective. Additionally or alternatively, the oligonucleotide of the present disclosure may comprise completely, partially or in combination, modified nucleotides which are derivatives with substitutions at the 2' position of the sugar, in particular with the following chemical modifications: O-methyl group (2'-O-Me) substitution, 2-methoxyethyl group (2'-O-MOE) substitution, fluoro group (2'-fluoro) substitution, chloro group (2'-Cl) substitution, bromo group (2'-Br) substitution, cyanide group (2'—CN) substitution, trifluoromethyl group (2'-CF3) substitution, OCF3 group (2'-OCF3) substitution, OCN group (2'-OCN) substitution, O-alkyl group (2'-O-alkyl) substitution, S-alkyl group (2'-S-alkyl) substitution, N-alkyl group (2'-N-akyl) substitution, O-alkenyl group (2'-O-alkenyl) substitution, S-alkenyl group (2'-S-alkenyl) substitution, N-alkenyl group (2'-N-alkenyl) substitution, SOCH3 group (2'-SOCH3) substitution, SO2CH3 group (2'-SO2$CH_3$) substitution, ONO2 group (2'-ONO2) substitution, NO2 group (2'-NO2) substitution, N3 group (2'-N3) substitution and/or NH2 group (2'—NH2) substitution. Additionally or alternatively, the oligonucleotide of the present disclosure may comprise completely or partially modified nucleotides wherein the ribose moiety is used to produce locked nucleic acid (LNA), in which a covalent bridge is formed between the 2' oxygen and the 4' carbon of the ribose, fixing it in the 3'-endo configuration. These molecules are extremely stable in biological medium, able to activate RNase H such as when LNA are located to extremities (gapmer) and form tight hybrids with complementary RNA and DNA.

In some embodiments, the oligonucleotide used in the context of the disclosure comprises modified nucleotides selected from the group consisting of LNA, 2'-OMe analogs, 2'-O-Met, 2'-O-(2-methoxyethyl) (MOE) oligomers, 2'-phosphorothioate analogs, 2'-fluoro analogs, 2'-CI analogs, 2'-Br analogs, 2'—CN analogs, 2'—CF3 analogs, 2'-OCF3 analogs, 2'-OCN analogs, 2'-O-alkyl analogs, 2'-S-alkyl analogs, 2'-N-alkyl analogs, 2'-O-alkenyl analogs, 2'-S-alkenyl analogs, 2'-N-alkenyl analogs, 2'-SOCH3 analogs, 2'-SO2CH3 analogs, 2'-ONO2 analogs, 2'-NO2 analogs, 2'-N3 analogs, 2'—NH2 analogs, tricyclo (tc)-DNAs, U7 short nuclear (sn) RNAs, tricyclo-DNA-oligoantisense molecules and combinations thereof (U.S. Provisional Patent Application Ser. No. 61/212,384 For: Tricyclo-DNA Antisense Oligonucleotides, Compositions and Methods for the Treatment of Disease, filed Apr. 10, 2009, the complete contents of which is hereby incorporated by reference).

In a particular embodiment, the oligonucleotide according to the disclosure is a LNA oligonucleotide. The term "LNA" (Locked Nucleic Acid) (or "LNA oligonucleotide") refers to an oligonucleotide containing one or more bicyclic, tricyclic or polycyclic nucleoside analogues also referred to as LNA nucleotides and LNA analogue nucleotides. LNA oligonucleotides, LNA nucleotides and LNA analogue nucleotides are generally described in International Publication No. WO 99/14226 and subsequent applications; International Publication Nos. WO 00/56746, WO 00/56748, WO 00/66604, WO 01/25248, WO 02/28875, WO 02/094250, WO 03/006475; U.S. Pat. Nos. 6,043,060, 6,268,490, 6,770,748, 6,639,051, and U.S. Publication Nos. 2002/0125241, 2003/0105309, 2003/0125241, 2002/0147332, 2004/0244840 and 2005/0203042, all of which are incorporated herein by reference. LNA oligonucleotides and LNA analogue oligonucleotides are commercially available from, for example, Proligo LLC, 6200 Lookout Road, Boulder, CO 80301 USA.

Other forms of oligonucleotides of the present disclosure are oligonucleotide sequences coupled to small nuclear RNA molecules such as U1 or U7 in combination with a viral transfer method based on, but not limited to, lentivirus or adeno-associated virus (Denti, M A, et al, 2008; Goyenvalle, A, et al, 2004).

Other forms of oligonucleotides of the present disclosure are peptide nucleic acids (PNA). In peptide nucleic acids, the deoxyribose backbone of oligonucleotides are replaced with a backbone more akin to a peptide than a sugar. Each subunit, or monomer, has a naturally occurring or non-naturally occurring base attached to this backbone. One such backbone is constructed of repeating units of N-(2-aminoethyl)glycine linked through amide bonds. Because of the radical deviation from the deoxyribose backbone, these compounds were named peptide nucleic acids (PNAs) (Dueholm et al., New J. Chem., 1997, 21, 19-31). PNA binds both DNA and RNA to form PNA/DNA or PNA/RNA duplexes. The resulting PNA/DNA or PNA/RNA duplexes are bound with greater affinity than corresponding DNA/DNA, DNA/RNA or RNA/RNA duplexes as determined by Tm's. This high thermal stability might be attributed to the lack of charge repulsion due to the neutral backbone in PNA. The neutral backbone of the PNA also results in the Tm's of PNA/DNA (RNA) duplex being practically independent of the salt concentration. Thus, the PNA/DNA (RNA) duplex interaction offers a further advantage over DNA/DNA, DNA/RNA or RNA/RNA duplex interactions which are highly dependent on ionic strength. Homopyrimidine PNAs have been shown to bind complementary DNA or RNA in an anti-parallel orientation forming (PNA) 2/DNA (RNA) triplexes of high thermal stability (see, e.g., Egholm, et al., Science, 1991, 254, 1497; Egholm, et al., J. Am. Chem. Soc., 1992, 114, 1895; Egholm, et al., J. Am. Chem. Soc., 1992, 114, 9677). In addition to increased affinity, PNA has also been shown to bind to DNA or RNA with increased specificity. When a PNA/DNA duplex mismatch is melted relative to the DNA/DNA duplex there is seen an 8 to 20 °C drop in the Tm. This magnitude of a drop in Tm is not seen with the corresponding DNA/DNA duplex with a mismatch present. The binding of a PNA strand to a DNA or RNA strand can occur in one of two orientations. The orientation is said to be anti-parallel when the DNA or RNA strand in a 5' to 3' orientation binds to the complementary PNA strand such that the carboxyl end of the PNA is directed towards the 5' end of the DNA or RNA and amino end of the PNA is directed towards the 3' end of the DNA or RNA. In the parallel orientation the carboxyl end and amino end of the PNA are just the reverse with respect to the 5'-3' direction of the DNA or RNA. A further advantage of PNA compared to oligonucleotides is that their polyamide backbones (having appropriate nucleobases or other side chain groups attached thereto) is not recognized by either nucleases or proteases and are not cleaved. As a result, PNAs are resistant to degradation by enzymes unlike nucleic acids and peptides.

WO92/20702 describes a peptide nucleic acid (PNA) compounds which bind complementary DNA and RNA more tightly than the corresponding DNA. PNA have shown strong binding affinity and specificity to complementary DNA (Egholm, M., et al., Chem. Soc., Chem. Commun., 1993, 800; Egholm, M., et.al., Nature, 1993, 365, 566; and Nielsen, P., et.al. Nucl. Acids Res., 1993, 21, 197). Furthermore, PNA's show nuclease resistance and stability in cell-extracts (Demidov, V. V., et al., Biochem. Pharmacol., 1994, 48, 1309-1313). Modifications of PNA include extended backbones (Hyrup, B., et.al. Chem. Soc., Chem. Commun., 1993, 518), extended linkers between the backbone and the nucleobase, reversal of the amida bond (Lagriffoul, P. H., et.al., Biomed. Chem. Lett., 1994, 4, 1081), and the use of a chiral backbone based on alanine (Dueholm, K. L, et.al., BioMed. Chem. Lett., 1994, 4, 1077). Peptide Nucleic Acids are described in U.S. Pat. Nos. 5,539,082 and 5,539,083. Peptide Nucleic Acids are further described in U.S. patent application Ser. No. 08/686,113.

Typically, the oligonucleotides of the present disclosure are obtained by conventional methods well known to those skilled in the art. For example, the oligonucleotide of the disclosure can be synthesized de novo using any of a number of procedures well known in the art. For example, the b-cyanoethyl phosphoramidite method (Beaucage et al., 1981); nucleoside H-phosphonate method (Garegg et al., 1986; Froehler et al., 1986, Garegg et al., 1986, Gaffney et al., 1988). These chemistries can be performed by a variety of automated nucleic acid synthesizers available in the market. These nucleic acids may be referred to as synthetic nucleic acids. Alternatively, oligonucleotide can be produced on a large scale in plasmids (see Sambrook, et al., 1989). Oligonucleotide can be prepared from existing nucleic acid sequences using known techniques, such as those employing restriction enzymes, exonucleases or endonucleases. Oligonucleotide prepared in this manner may be referred to as isolated nucleic acids.

The one skilled in the art can easily provide some approaches and modifications for enhancing the delivery and the efficacy of oligonucleotides such as chemical modification of the oligonucleotides, lipid-and polymer-based nanoparticles or nanocarriers, ligand-oligonucleotide conjugates by linking oligonucleotides to targeting agents such as carbohydrates, peptides, antibodies, aptamers, lipids or small molecules and small molecules that improve oligonucleotide delivery such as described in Juliano R L. The delivery of therapeutic oligonucleotides. Nucleic Acids Res. 2016 Aug. 19; 44 (14): 6518-48. Lipophilic conjugates and lipid conjugates include fatty acid-oligonucleotide conjugates; sterol-oligonucleotide conjugates and vitamin-oligonucleotide conjugates.

In some embodiments, the oligonucleotide of the present disclosure is modified by substitution at the 3' or the 5' end by a moiety comprising at least three saturated or unsaturated, particularly saturated, linear or branched, particularly linear, hydrocarbon chains comprising from 2 to 30 carbon atoms, particularly from 5 to 20 carbon atoms, more particularly from 10 to 18 carbon atoms as described in WO2014195432.

In some embodiments, the oligonucleotide of the present disclosure is modified by substitution at the 3' or the 5' end by a moiety comprising at least one ketal functional group, wherein the ketal carbon of said ketal functional group bears two saturated or unsaturated, particularly saturated, linear or branched, particularly linear, hydrocarbon chains comprising from 1 to 22 carbon atoms, particularly from 6 to 20 carbon atoms, in particular to 19 carbon atoms, and even more particularly from 12 to 18 carbon atoms as described in WO2014195430.

In a particular embodiment, the oligonucleotide of the present disclosure is conjugated to a second molecule. Typically said second molecule is selected from the group consisting of aptamers, antibodies or polypeptides. For example, the oligonucleotide of the present disclosure may be conjugated to a cell penetrating peptide. Cell penetrating peptides are well known in the art and include for example the TAT peptide (Bechara C, Sagan S. Cell-penetrating peptides: 20 years later, where do we stand? FEBS Lett. 2013 Jun. 19; 587 (12): 1693-702).

In some embodiments, the oligonucleotide of the present disclosure is associated with a carrier or vehicle, e.g., liposomes or micelles, although other carriers could be used, as would be appreciated by one skilled in the art. Liposomes are vesicles made of a lipid bilayer having a structure similar to biological membranes. Such carriers are used to facilitate the cellular uptake or targeting of the oligonucleotide, or improve the oligonucleotide's pharmacokinetic or therapeutic properties. For example, the oligonucleotide of the present disclosure may also be administered encapsulated in liposomes, pharmaceutical compositions wherein the active ingredient is contained either dispersed or variously present in corpuscles consisting of aqueous concentric layers adherent to lipidic layers. The oligonucleotide, depending upon solubility, may be present both in the aqueous layer and in the lipidic layer, or in what is generally termed a liposomal suspension. The hydrophobic layer, generally but not exclusively, comprises phospholipids such as lecithin and sphingomyelin, steroids such as cholesterol, more or less ionic surfactants such as diacetylphosphate, stearylamine, or phosphatidic acid, or other materials of a hydrophobic nature. The diameters of the liposomes generally range from about 15 nm to about 5 microns. The use of liposomes as drug delivery vehicles offers several advantages. Liposomes increase intracellular stability, increase uptake efficiency and improve biological activity. Liposomes are hollow spherical vesicles composed of lipids arranged in a similar fashion as those lipids, which make up the cell membrane. They have an internal aqueous space for entrapping water-soluble compounds and range in size from 0.05 to several microns in diameter. Several studies have shown that liposomes can deliver nucleic acids to cells and that the nucleic acids remain biologically active. For example, a liposome delivery vehicle originally designed as a research tool, such as Lipofectin, can deliver intact nucleic acid molecules to cells. Specific advantages of using liposomes include the following: they are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system.

In some embodiments, the oligonucleotide of the present disclosure is complexed with a complexing agent to increase cellular uptake of oligonucleotides. An example of a complexing agent includes cationic lipids. Cationic lipids can be used to deliver oligonucleotides to cells. The term "cationic lipid" includes lipids and synthetic lipids having both polar and non-polar domains and which are capable of being positively charged at or around physiological pH and which bind to polyanions, such as nucleic acids, and facilitate the delivery of nucleic acids into cells. In general, cationic lipids include saturated and unsaturated alkyl and alicyclic ethers and esters of amines, amides, or derivatives thereof. Straight-chain and branched alkyl and alkenyl groups of cationic lipids can contain, e.g., from 1 to about 25 carbon atoms. Particularly, straight chain or branched alkyl or alkene groups have six or more carbon atoms. Alicyclic groups include cholesterol and other steroid groups. Cationic lipids can be prepared with a variety of counterions (anions) including, e.g., Cl—, Br—, I—, F—, acetate, trifluoroacetate, sulfate, nitrite, and nitrate. Examples of cationic lipids include: polyethylenimine, polyamidoamine (PAMAM) starburst dendrimers, Lipofectin (a combination of DOTMA and DOPE), Lipofectase, Lipofectamine, DOPE, Cytofectin (Gilead Sciences, Foster City, Calif.), and Eufectins (JBL, San Luis Obispo, Calif.). Cationic liposomes may comprise the following: N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3p-[N-(N',N'-dimethylaminoethane) carbamoyl]cholesterol (DC-Chol), 2,3,-dioleyloxy-N-[2 (sperminecarboxamido)ethyl]-N,N-dimethyl-1-propanaminium trifluoroacetate (DOSPA), 1,2-dimyristyloxypropyl-3-dimethy-1-hydroxyethyl ammonium bromide; and dimethyldioctadecylammonium bromide (DDAB). The cationic lipid N-(1-(2,3-dioleyloxy) propyl)-N,N, N-trimethylammonium chloride (DOTMA), for example, was found to increase 1000-fold the antisense effect of a phosphorothioate oligonucleotide (Vlassov et al., 1994, Biochimica et Biophysica Acta 1197:95-108). Oligonucleotides can also be complexed with, e.g., poly(L-lysine) or avidin and lipids may, or may not, be included in this mixture (e.g., steryl-poly(L-lysine). Cationic lipids have been used in the art to deliver oligonucleotides to cells (see, e.g., U.S. Pat. Nos. 5,855,910; 5,851,548; 5,830,430; 5,780,053; 5,767,099; Lewis et al. 1996. Proc. Natl. Acad. Sci. USA 93:3176; Hope et al. 1998. Molecular Membrane Biology 15:1). Other lipid compositions which can be used to facilitate uptake of the instant oligonucleotides can be used in connection with the claimed methods. In addition to those listed supra, other lipid compositions are also known in the art and include, e.g., those taught in U.S. Pat. Nos. 4,235,871; 4,501,728; 4,837,028; 4,737,323.

The term "ionotropic glutamate receptors" comprise members of the NMDA (N-methyl-D-aspartate), AMPA (α-amino-3-hydroxy-5-methyl-4-isoxazoleproprionic acid) and kainate receptor classes. Functional kainate receptors can be assembled into tetrameric assemblies from the homomeric or heteromeric combination of five subunits named GluK1, GluK2, GluK3, GluK4 and GluK5 subunits (Reiner et al., 2012). The targets of the disclosure are, in some instances, kainate receptor complexes composed of GluK2 and GluK5. Inhibiting the expression of Grik2 gene is sufficient to abolish GluK2/GluK5 kainate receptor function, given the observation that GluK5 by itself does not form functional homomeric channels.

The term "GluK2", also known as "GluR6", "GRIK2", "MRT6", "EAA4", or "GluK6", refers to the glutamate ionotropic receptor kainate type subunit 2, as named in the currently used IUPHAR nomenclature (Collingridge, G. L., Olsen, R. W., Peters, J., Spedding, M., 2009. A nomenclature for ligand-gated ion channels. Neuropharmacology 56, 2-5). The terms GluK2 containing kainate receptor, GluK2 receptor, and GluK2 subunit may be used interchangeably throughout and generally refer to the protein encoded by or expressed by a Grik2 gene.

In some embodiments, the oligonucleotide of the present disclosure is a GluK2 inhibitor.

In one embodiment, the GluK2 inhibitor of the disclosure is also known as a Grik2 expression inhibitor.

The term "expression" when used in the context of expression of a gene or nucleic acid refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include messenger RNAs, which are modified, by processes such as capping, polyadenylation, methylation, and editing, and proteins (e.g., GluK2) modified by, for example, methylation, acetylation, phosphorylation, ubiquitination, SUMOylation, ADP-ribosylation, myristoylation, and glycosylation.

Inhibiting the expression of GluK2 also inhibits the levels of Gluk2/GluK5 heteromeric receptors (Ruiz et al, J Neuroscience 2005). While not wishing to be bound to any theory, the disclosure is based on the principle that sufficient removal of GluK2 alone should remove all GluK2/GluK5 heteromers.

An "inhibitor of expression" refers to a natural or synthetic compound that has a biological effect to inhibit or decrease the expression of a gene, e.g., the Grik2 gene. It will be understood to those persons of skill in the relevant art that inhibiting expression of a gene, e.g., the Grik2 gene, typically results in a decrease or even abolition of the gene product (protein, e.g., GluK2 protein) in target cells or tissues, although various levels of inhibition may be achieved. Inhibiting or decreasing expression is typically referred to as knockdown In one embodiment, the GluK2 inhibitor of the disclosure is an antisense nucleic acid.

Grik2 expression inhibitors for use in the present disclosure may be based on antisense oligonucleotide constructs. Anti-sense oligonucleotides, including antisense RNA molecules and antisense DNA molecules, would act to directly block the translation of Grik2 mRNA by binding (e.g., hybridizing) thereto and thus preventing protein translation or increasing mRNA degradation, thus decreasing the level of GluK2 proteins, and thus activity, in a cell. For example, antisense oligonucleotides of at least about 15 bases and complementary to unique regions of the mRNA transcript sequence encoding GluK2 can be synthesized, e.g., by conventional phosphodiester techniques and administered by e.g., intravenous injection or infusion. Methods for using antisense techniques for specifically alleviating gene expression of genes whose sequence is known are well known in the art (e.g., see U.S. Pat. Nos. 6,566,135; 6,566, 131; 6,365,354; 6,410,323; 6,107,091; 6,046,321; and 5,981,732, each of which is incorporated by reference herein in its entirety).

In one embodiment, the GluK2 inhibitor of the disclosure is a siRNA.

Small inhibitory RNAs, also referred to as short interfering RNAs (siRNAs) can also function as GluK2 expression inhibitors for use in the present disclosure. Grik2 gene expression can be reduced by contacting the subject or cell with a small double stranded RNA (dsRNA), or a vector or construct causing the production of a small double stranded RNA, such that Grik2 expression is specifically inhibited (i.e., RNA interference or RNAi) by degradation of mRNAs in a sequence specific manner. Methods for selecting an appropriate dsRNA or dsRNA-encoding vector are known in the art for genes whose sequence is known (e.g., see Tuschl, T. et al. (1999); Elbashir, S. M. et al. (2001); Hannon, G J. (2002); McManus, MT. et al. (2002); Brummelkamp, T R. et al. (2002); U.S. Pat. Nos. 6,573,099 and 6,506,559; and International Patent Publication Nos. WO 01/36646, WO 99/32619, and WO 01/68836, each of which is incorporated by reference herein in its entirety).

In one embodiment, the GluK2 inhibitor of the disclosure is a shRNA.

Short hairpin RNAs (shRNA) can also function as Grik2 expression inhibitors for use in the present disclosure. A short hairpin RNA (shRNA) is a sequence of RNA that makes a tight hairpin turn that can be used to silence gene expression via RNA interference. shRNA is generally expressed using a vector introduced into cells, wherein the vector utilizes the U6 promoter (e.g., SEQ ID NO: 29) or another Pol III promoter to ensure that the shRNA is always expressed. In some embodiments, the vector (e.g., a lentiviral vector) may be passed on to daughter cells following cell division, allowing the gene silencing nucleic acids to be inherited. The shRNA hairpin structure is cleaved by the cellular machinery into an siRNA, which is then bound to the RNA-induced silencing complex (RISC). This complex binds to and cleaves mRNAs that are fully or partially complementary to the siRNA sequence to which it is bound.

In one embodiment, the GluK2 inhibitor of the disclosure is a miRNA.

MicroRNAs (miRNAs) can also function as Grik2 expression inhibitors for use in the present disclosure. MicroRNA refers to antisense RNA molecules that are generally 21 to 22 nucleotides in length, even though lengths of 19 and up to 25 nucleotides have been reported, and suppress translation of targeted mRNAs. MicroRNA biogenesis generally involves transcription of a non-protein-coding gene or a non-coding region (e.g., intron or UTR) of a protein-coding gene into a primary transcript (i.e., pri-miRNA), which is then processed by the Microprocessor complex in the nucleus to form another precursor microRNA molecule ("precursor miRNA" or "pre-miRNA"). Pre-miRNA is subsequently translocated out of the nucleus to be further processed into mature miRNA. The pre-miRNA have two regions of complementarity that enable them to form a stem-loop- or fold-back-like structure, which is cleaved in animals by a ribonuclease Ill-like nuclease enzyme called Dicer. The processed miRNA is typically a part of the stem. The processed miRNA (also referred to as "mature miRNA") becomes part of a complex to downregulate, e.g., repress translation, of a particular target gene. Within the context of the present disclosure, pri-miRNA refers to a microRNA precursor containing, in the 5' to 3' direction: a 5' flanking sequence, a stem-loop sequence containing a guide sequence, a loop sequence (e.g., a miRNA loop sequence, such as, e.g., a miR-30 loop sequence), and a passenger sequence, and a 3' flanking sequence. Additionally, a pri-miRNA may refer to a microRNA precursor containing, in the 5' to 3' direction: a 5' flanking sequence, a stem-loop sequence containing a passenger sequence, a loop sequence (e.g., a miRNA loop sequence, such as, e.g., a miR-30 loop sequence), and a guide sequence, and a 3' flanking sequence. In particular examples, the pri-miRNA may be an RNA equivalent of the DNA sequence of SEQ ID NO: 21 or SEQ ID NO: 23. According to the present disclosure, pre-miRNA refers to a microRNA precursor having a stem-loop sequence containing a guide sequence, a loop sequence (e.g., a miRNA loop sequence, such as, e.g., a miR-30 loop sequence), and a passenger sequence. In particular examples, the pre-miRNA may be an RNA equivalent of the DNA sequence of SEQ ID NO: 20 or SEQ ID NO: 22.

In one embodiment, the GluK2 inhibitor of the disclosure is a miRNA-adapted shRNA (shmiRNA). shmiRNA agents refer to chimeric molecules that incorporate antisense sequences within the −5p or the −3p arm of a microRNA scaffold (e.g., a miR-30 scaffold) containing microRNA flanking and loop sequences. Compared to an shRNA, shmiRNA generally has a longer stem-loop structure based on microRNA-derived sequences, with the −5p and the −3p arm exhibiting full or partial complementarity (e.g., mismatches, G: U wobbles). Owing to their longer sequences and processing requirements, shmiRNAs are generally expressed from a Pol II promoter. These constructs have also been shown to exhibit reduced toxicity as compared to shRNA-based agents.

Multiple miRNAs may be employed to knockdown Grik2 (and subsequently its gene product, GluK2). The miRNAs may be complementary to different target transcripts or different binding sites of a target transcript. Polycistronic transcripts may also be utilized to enhance the efficiency of target gene knockdown. In some embodiments, multiple genes encoding the same miRNAs or different miRNAs may be regulated together in a single transcript, or as separate transcripts in a single vector cassette. In one embodiment, the vector is a viral vector, including but not limited to recombinant adeno-associated viral (rAAV) vectors, lentiviral vectors, retroviral vectors and retrotransposon-based vector systems.

The antisense RNA that is complementary to the sense target sequence is encoded by a nucleic acid sequence for the production of any of the foregoing inhibitors (e.g., antisense, siRNAs, shRNAs, miRNAs, or shmiRNA). The polynucleotide encoding double stranded RNA of interest is incorporated into a gene cassette, e.g., an expression cassette in which transcription of the DNA is controlled by a promoter.

In some embodiments, the antisense nucleic acid of the disclosure targets and binds (e.g., hybridizes) to a nucleic acid sequence comprising or consisting of the sequence AAARCAGGCATTAGCTATG (SEQ ID NO: 1), wherein "R" represents an adenine or a guanine.

In some embodiments, the antisense nucleic acid of the disclosure targets and binds (e.g., hybridizes) to a nucleic acid sequence comprising or consisting of a sequence SEQ ID NO: 2 or SEQ ID NO: 16, which can correspond to a passenger sequence of a nucleic acid construct of the disclosure. This oligonucleotide is able to bind to and hybridize (e.g., by way of complementary base pairing) with an antisense sequence (e.g., SEQ ID NO: 14 or SEQ ID NO: 18) targeting the Grik2 gene or Grik2 mRNA of multiple species, including human and rat.

In some embodiments, the antisense nucleic acid of the disclosure targets and binds to a nucleic acid sequence comprising or consisting of the sequence SEQ ID NO: 3 or SEQ ID NO: 17, which can correspond to a passenger sequence of a nucleic acid construct of the disclosure. This oligonucleotide is able to hybridize with an antisense sequence (e.g., SEQ ID NO: 15 or SEQ ID NO: 19) targeting the Grik2 gene or Grik2 mRNA of the mouse.

The foregoing gene sequences are represented as DNA (e.g., cDNA) sequences that can be incorporated into a vector of the disclosure; however, these sequences may also be represented as corresponding RNA sequences (e.g., a gene coding RNA) that are synthesized from the vector within the cell (e.g., any one of SEQ ID NOS: 16-19). One skilled in the art would understand that the cDNA sequence is equivalent to the RNA (e.g., a gene coding RNA) sequence, except for the substitution of uridines with thymidines, and can be used for the same purpose herein, i.e., the generation of an antisense oligonucleotide for inhibiting the expression of Grik2 mRNA. In the case of DNA vectors (e.g., AAV), the polynucleotide containing the antisense nucleic acid is a DNA sequence. In the case of RNA vectors, the expression cassette incorporates the RNA equivalent of the antisense DNA sequences described herein.

In other embodiments, each of SEQ ID NOS: 1-3 correspond to a cDNA sequence of a corresponding region of a Grik2 mRNA (e.g., SEQ ID NO: 11) targeted by the antisense oligonucleotides of the disclosure. In further embodiments, each of SEQ ID NOS: 1-3, 16, or 17 correspond to a passenger sequence of a 5' arm or a 3' arm of a stem-loop RNA or its DNA equivalent sequence containing a guide sequence (e.g., any one of SEQ ID NOS: 14, 15, 18, or 19) that is fully or partially complementary to the passenger sequence and a loop sequence operably linking the 5' or 3' end of the 3' or 5' end of the guide sequence or the passenger sequence, wherein the stem-loop RNA or its DNA equivalent sequence is incorporated into a nucleic acid expression vector (e.g., an AAV or lentiviral vector) for heterologous expression in one or more target cells (e.g., neurons or glial cells).

In some embodiments, the antisense nucleic acid of the disclosure comprises or consists of the sequence SEQ ID NO: 14 or SEQ ID NO: 18. This oligonucleotide is able to target the Grik2 gene or Grik2 mRNA of multiple species, including human and rat. In some embodiments, SEQ ID NO: 14 or SEQ ID NO: 18 is a guide sequence that is fully or partially complementary to a passenger sequence (e.g., SEQ ID NO: 2 or SEQ ID NO: 16). In some embodiments, the antisense sequence of SEQ ID NO: 14 is transcribed within the cell into an RNA sequence of SEQ ID NO: 18.

In some embodiments, the antisense nucleic acid of the disclosure comprises or consists of the sequence SEQ ID NO:15 or SEQ ID NO: 19. This oligonucleotide is able to target a murine Grik2 gene or Grik2 mRNA. In some embodiments, SEQ ID NO: 15 or SEQ ID NO: 19 is a guide sequence that is fully or partially complementary to a passenger sequence (e.g., SEQ ID NO: 3 or SEQ ID NO: 17). In some embodiments, the antisense sequence of SEQ ID NO: 15 is transcribed within the cell into an RNA sequence of SEQ ID NO: 19.

In some embodiments, the antisense nucleic acid of the disclosure comprises or consists of a nucleic acid sequence having at least 70% identity to the antisense nucleic acid of the disclosure.

According to the disclosure a first nucleic acid sequence having at least 70% sequence identity with a second nucleic acid sequence means that the first sequence has 70%; 71%; 72%; 73%; 74%; 75%; 76%; 77%; 78%; 79%; 80%; 81%; 82%; 83%; 84%; 85%; 86%; 87%; 88%; 89%; 90%; 91%; 92%; 93%; 94%; 95%; 96%; 97%; 98%; or 99% identity to the second nucleic acid sequence. Nucleic acid sequence identity is particularly determined using a suitable sequence alignment algorithm and default parameters, such as BLASTn (Karlin and Altschul, Proc. Natl Acad. Sci. USA 87 (6): 2264-2268 (1990)).

Nucleic Acid Vectors

In a particular embodiment, oligonucleotides (e.g., antisense nucleic acid) of the disclosure may be delivered in vivo alone or in association with a vector. In its broadest sense, a "vector" is any vehicle capable of facilitating the transfer of the oligonucleotide of the disclosure to the cells. In some examples, the vector disclosed herein may directly transport the mature antisense nucleic acid sequences to cells with reduced degradation relative to the extent of degradation that would result in the absence of the vector. In other cases, the vector disclosed herein delivers a transgene (e.g., a heterologous polynucleotide containing the antisense nucleic acid sequence) that is subsequently transcribed (e.g., in the case of an AAV) or reverse transcribed (e.g., in the case of a retroviral vector) within the cell. In general, the vectors useful in the disclosure include, but are not limited to, naked plasmids, non-viral delivery systems (cationic transfection agents, liposomes, lipid nanoparticles, and the like), phagemids, viruses, other vehicles derived from viral or bacterial sources that have been manipulated by the insertion or incorporation of the oligonucleotide sequences. Viral vectors include, but are not limited to nucleic acid sequences from the following viruses: RNA viruses such as a retrovirus (as for example Moloney murine leukemia virus and lentiviral derived vectors), Harvey murine sarcoma virus, murine mammary tumor virus, and Rous sarcoma virus; adenovirus, adeno-associated virus (AAV); SV40-type viruses; polyoma viruses; Epstein-Barr viruses; papilloma viruses; herpes virus; vaccinia virus; polio virus. One can readily employ other vectors not named but known to the art.

In some embodiment, the present disclosure relates a vector for delivery of a heterologous nucleic acid, wherein the nucleic acid encodes an inhibitory RNA that specifically binds (e.g., hybridizes) to Grik2 mRNA and inhibits expression of Grik2 in a cell.

Accordingly, an object of the disclosure relates to a vector comprising an antisense sequence of a corresponding region of the GluK2 receptor, or variants thereof.

In another embodiment, the vector of the disclosure may comprise any variant of the antisense sequence of a corresponding region of the GluK2 receptor.

In another embodiment, the vector of the disclosure may comprise any variant of the antisense sequence of any variant of the corresponding region of the GluK2 receptor.

Accordingly, an object of the disclosure relates to a vector comprising an antisense sequence that targets a corresponding region of the GluK2 receptor, or variants thereof.

Accordingly, an object of the disclosure relates to a vector comprising a shRNA sequence that targets a corresponding region of the GluK2 receptor, or variants thereof.

Accordingly, an object of the disclosure relates to a vector comprising a miRNA sequence that targets a corresponding region of the GluK2 receptor, or variants thereof.

Accordingly, an object of the disclosure relates to a vector comprising a shmiRNA sequence that targets a corresponding region of the GluK2 receptor, or variants thereof.

Accordingly, an object of the disclosure relates to a vector comprising the sequence SEQ ID NO: 1 that encodes a corresponding region of the GluK2 receptor, or variants thereof.

Accordingly, an object of the disclosure relates to a vector comprising the sequence SEQ ID NO: 2 or SEQ ID NO: 16 that encodes a corresponding region of the GluK2 receptor, or variants thereof.

Accordingly, an object of the disclosure relates to a vector comprising the sequence SEQ ID NO: 3 or SEQ ID NO 17 that encodes a corresponding region of the GluK2 receptor, or variants thereof.

In some embodiments, the sequences of SEQ ID NOS: 1-3, 16, or 17 are oriented in the sense direction with respect to a corresponding region of a Grik2 mRNA sequence (any one of the Grik2 mRNA sequences disclosed herein).

Accordingly, an object of the disclosure relates to a vector comprising the sequence SEQ ID NO: 14 or SEQ ID NO: 18 or a variant thereof having at least 85% (e.g., at least 90%, 91%, 92%, 93%, 94%, 95%, 96%, 97%, 98%, 99%, or more)

sequence identity to the nucleic acid sequence of SEQ ID NO: 14 or SEQ ID NO: 18 that binds (e.g., hybridizes) to a corresponding region of the mRNA sequence encoding a GluK2 receptor, or variants thereof. Particularly, the variant does not have the nucleic acid sequence of SEQ ID NOs: 1, 2 or 3. In some embodiments, the oligonucleotide of SEQ ID NO: 14 is transcribed from the vector (e.g., an AAV) into an RNA sequence of SEQ ID NO: 18. In some embodiments, the vector (e.g., a retroviral vector, such as, e.g., a lentiviral vector) comprises the RNA sequence of SEQ ID NO: 18.

Accordingly, an object of the disclosure relates to a vector comprising the sequence SEQ ID NO: 15 or SEQ ID NO: 19 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 15 or SEQ ID NO: 19 that binds (e.g., hybridizes) to a corresponding region of the mRNA sequence encoding a GluK2 receptor, or variants thereof. Particularly, the variant does not have the nucleic acid sequence of SEQ ID NOS: 1, 2 or 3. In some embodiments, the oligonucleotide of SEQ ID NO: 15 is transcribed from the vector (e.g., an AAV) into an RNA sequence of SEQ ID NO: 19. In some embodiments, the vector (e.g., a retroviral vector, such as, e.g., a lentiviral vector) comprises the RNA sequence of SEQ ID NO: 19.

In some embodiments, SEQ ID NOS: 14, 15, 18, or 19 are oriented in the antisense direction with respect to (i.e., are a reverse complement of) a corresponding region of a Grik2 mRNA sequence (any one of the Grik2 mRNA sequences disclosed herein).

In another embodiment, the vector of the disclosure may comprise any variant of the sequence SEQ ID NO: 1 that encodes a corresponding region of the GluK2 receptor, or variants thereof.

In another embodiment, the vector of the disclosure may comprise any variant of the sequence SEQ ID NO: 2 or SEQ ID NO: 16 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 2 or SEQ ID NO: 16 that encodes a corresponding region of the GluK2 receptor, or variants thereof.

In another embodiment, the vector of the disclosure may comprise any variant of the sequence SEQ ID NO: 3 or SEQ ID NO: 17 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 3 or SEQ ID NO: 17 that encodes a corresponding region of the GluK2 receptor, or variants thereof.

In another embodiment, the vector of the disclosure may comprise any variant of the sequence SEQ ID NO: 14 or SEQ ID NO: 18 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 14 or SEQ ID NO: 18 that binds (e.g., hybridizes) to a corresponding region of the mRNA sequence encoding a GluK2 receptor, or variants thereof. Particularly, the variant does not have the nucleic acid sequence of SEQ ID NOs: 1, 2 or 3.

In another embodiment, the vector of the disclosure may comprise any variant of the sequence SEQ ID NO: 15 or SEQ ID NO: 19 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 15 or SEQ ID NO: 19 that binds (e.g., hybridizes) to a corresponding region of the mRNA sequence encoding a GluK2 receptor, or variants thereof. Particularly, the variant does not have the nucleic acid sequence of SEQ ID NOs: 1, 2 or 3.

Accordingly, an object of the disclosure relates to a vector comprising an antisense sequence of a corresponding region of the GluK2 receptor, or variants thereof and an hSyn promoter.

Accordingly, an object of the disclosure relates to a vector comprising an antisense sequence of a corresponding region of the GluK2 receptor, or variants thereof and a hSyn promoter.

Accordingly, an object of the disclosure relates to a vector comprising a miRNA sequence that targets a corresponding region of the GluK2 receptor, or variants thereof and an hSyn promoter.

Accordingly, an object of the disclosure relates to a vector comprising a shRNA sequence that targets a corresponding region of the GluK2 receptor, or variants thereof and an hSyn promoter.

Accordingly, an object of the disclosure relates to a vector comprising a shmiRNA sequence that targets a corresponding region of the GluK2 receptor, or variants thereof and an hSyn promoter.

Accordingly, an object of the disclosure relates to a vector comprising an antisense sequence of a corresponding region of the GluK2 receptor, or variants thereof and a calcium/calmodulin-dependent kinase II (CaMKII) promoter (e.g., any one of SEQ ID NOs: 31-35).

Accordingly, an object of the disclosure relates to a vector comprising a miRNA sequence that targets a corresponding region of the GluK2 receptor, or variants thereof and a CaMKII promoter.

Accordingly, an object of the disclosure relates to a vector comprising a shRNA sequence that targets a corresponding region of the GluK2 receptor, or variants thereof and a CaMKII promoter.

Accordingly, an object of the disclosure relates to a vector comprising a shmiRNA sequence that targets a corresponding region of the GluK2 receptor, or variants thereof and a CaMKII promoter.

Accordingly, an object of the disclosure relates to a vector comprising the sequence SEQ ID NO: 1 and a promoter. In some embodiments, the vector comprises the sequence set forth in SEQ ID NO: 1 and an hSyn promoter (e.g., SEQ ID NO: 27 or SEQ ID NO: 28), CaMKII promoter (e.g., SEQ ID NOs: 31-35), U6 promoter (e.g., SEQ ID NO: 29), or Pol III promoter.

The U6 promoter may be a polynucleotide having a nucleic acid sequence of SEQ ID NO: 29, or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 29, as is shown below.

```
                                              (SEQ ID NO: 29)
ATCCGACGCCGCCATCTCTAGGCCCGCGCCGGCCCCCTCGCACAGACTT

GTGGGAGAAGCTCGGCTACTCCCCTGCCCCGGTTAATTTGCATATAATA

TTTCCTAGTAACTATAGAGGCTTAATGTGCGATAAAAGACAGATAATCT

GTTCTTTTTAATACTAGCTACATTTTACATGATAGGCTTGGATTTCTAT

AAGAGATACAAATACTAAATTATTATTTTAAAAAACAGCACAAAAGGAA

ACTCACCCTAACTGTAAAGTAATTGTGTGTTTTGAGACTATAAATATCC

CTTGGAGAAAAGCCTTGTT
```

The CaMKII promoter may be a polynucleotide having a nucleic acid sequence of any one of SEQ ID NOs: 31-35, or a variant thereof having at least 85% (e.g., at least 90%, 91%, 92%, 93%, 94%, 95%, 96%, 97%, 98%, 99%, or more) sequence identity to the nucleic acid sequence of any one of SEQ ID NOs: 31-35, as is shown below.

CaMKII promoter, alpha subunit (RefSeq NM_171825, *H. sapiens*)
(SEQ ID NO: 30)
GATGCTGACGAAGGCTCGCGAGGCTGTGAGCAGCCACAGTGCCCTGCTC
AGAAGCCCCGG CaMKII promoter, beta 1 subunit (RefSeq NM_172084, *H. sapiens*)
(SEQ ID NO: 31)
GTCTCCCGCGCCCGCGCCCGTGTCGCCGCCGTGCCCGCGAGCGGGAGCC
GGAGTCGCCGC CaMKII promoter, beta 2 subunit (RefSeq NM_172084, *H. sapiens*)
(SEQ ID NO: 32)
CGTGTGCAGATGCAGGGCGCCGGTGCCCTGCGGGTGCGGGTGCAGGAGC
AGCGTGTGCAG CaMKII promoter, delta subunit (RefSeq NM_172115, *H. sapiens*)
(SEQ ID NO: 33)
CCCCACGCCACCCTTTCTGGTCATCTCCCCTCCCGCCCCGCCCCTGCGC
ACACTCCCTCG CaMKII promoter, gamma subunit (RefSeq NM_172171, *H. sapiens*)
(SEQ ID NO: 34)
TCTCCCCGGTAAAGTCTCGCGGTGCTGCCGGGCTCAGCCCCGTCTCCTC
CTCTTGCTCCC Additional CaMKII promoters may include the human alpha CaMKII promoter sequence described in Wang et al. (*Mol. Biol. Rep.* 35 (1): 37-44, 2007), the disclosure of which is incorporated in its entirety herein as it relates to the CaMKII promoter sequence.

The CAG promoter may be a polynucleotide having the nucleic acid of SEQ ID NO: 35 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 35, as is shown below.

(SEQ ID NO: 35)
GACATTGATTATTGACTAGTTATTAATAGTAATCAATTACGGGGTCATT

AGTTCATAGCCCATATATGGAGTTCCGCGTTACATAACTTACGGTAAAT

GGCCCGCCTGGCTGACCGCCCAACGACCCCCGCCCATTGACGTCAATAA

TGACGTATGTTCCCATAGTAACGCCAATAGGGACTTTCCATTGACGTCA

ATGGGTGGAGTATTTACGGTAAACTGCCCACTTGGCAGTACATCAAGTG

TATCATATGCCAAGTACGCCCCCTATTGACGTCAATGACGGTAAATGGC

CCGCCTGGCATTATGCCCAGTACATGACCTTATGGGACTTTCCTACTTG

GCAGTACATCTACGTATTAGTCATCGCTATTACCATGGTCGAGGTGAGC

CCCACGTTCTGCTTCACTCTCCCCATCTCCCCCCCCTCCCCACCCCCAA

TTTTGTATTTATTTATTTTTTAATTATTTTGTGCAGCGATGGGGGCGG

GGGGGGGGGGGGCGCGCGCCAGGCGGGGCGGGGCGGGGCGAGGGGCGG

GGCGGGGCGAGGCGGAGAGGTGCGGCGGCAGCCAATCAGAGCGGCGCGCT

CCGAAAGTTTCCTTTTATGGCGAGGCGGCGGCGGCGGCGGCCCTATAAA

-continued

AAGCGAAGCGCGCGGCGGGCGGGAGTCGCTGCGCGCTGCCTTCGCCCCG

TGCCCCGCTCCGCCGCCGCCTCGCGCCGCCCGCCCCGGCTCTGACTGAC

CGCGTTACTCCCACAGGTGAGCGGGCGGGACGGCCCTTCTCCTCCGGGCT

GTAATTAGCGCTTGGTTTAATGACGGCTTGTTTCTTTTCTGTGGCTGCG

TGAAAGCCTTGAGGGGCTCCGGGAGGGCCCTTTGTGCGGGGGGAGCGGC

TCGGGGGGTGCGTGCGTGTGTGTGTGCGTGGGGAGCGCCGCGTGCGGCT

CCGCGCTGCCCGGCGGCTGTGAGCGCTGCGGGCGCGGCGCGGGGCTTTG

TGCGCTCCGCAGTGTGCGCGAGGGGAGCGCGGCCGGGGGCGGTGCCCCG

CGGTGCGGGGGGGGCTGCGAGGGGAACAAAGGCTGCGTGCGGGGTGTGT

GCGTGGGGGGGTGAGCAGGGGGTGTGGGCGCGTCGGTCGGGCTGCAACC

CCCCCTGCACCCCCCTCCCCGAGTTGCTGAGCACGGCCCGGCTTCGGGT

GCGGGGCTCCGTACGGGGCGTGGCGCGGGGCTCGCCGTGCCGGGCGGGG

GGGGCGGCAGGTGGGGGTGCCGGGCGGGGCGGGGCCGCCTCGGGCCGGG

GAGGGCTCGGGGGAGGGGCGCGGCGGCCCCCGGAGCGCCGGCGGCTGTC

GAGGCGCGGCGAGCCGCAGCCATTGCCTTTTATGGTAATCGTGCGAGAG

GGCGCAGGGACTTCCTTTGTCCCAAATCTGTGCGGAGCCGAAATCTGGG

AGGCGCCGCCGCACCCCCTCTAGCGGGCGCGGGGCGAAGCGGTGCGGCG

CCGGCAGGAAGGAAATGGGCGGGGAGGGCCTTCGTGCGTCGCCGCGCCG

CCGTCCCCTTCTCCCTCTCCAGCCTCGGGGCTGTCCGCGGGGGGACGGC

TGCCTTCGGGGGGGACGGGGCAGGGCGGGGTTCGGCTTCTGGCGTGTGA

CCGGCGGCTCTAGAGCCTCTGCTAACCATGTTCATGCCTTCTTCTTTTT

CCTACAGCTCCTGGGCAACGTGCTGGTTATTGTGCTGTCTCATCATTTT

GGCAAAG

Accordingly, an object of the disclosure relates to a vector comprising the sequence SEQ ID NO: 2 or SEQ ID NO: 16 and a promoter. In some embodiments, the vector comprises the sequence set forth in SEQ ID NO: 2 or SEQ ID NO: 16 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 2 or SEQ ID NO: 16 and an hSyn, CaMKII promoter, U6 promoter, or Pol III promoter.

Accordingly, an object of the disclosure relates to a vector comprising the sequence SEQ ID NO: 3 or SEQ ID NO: 17 and a promoter. In some embodiments, the vector comprises the sequence set forth in SEQ ID NO: 3 or SEQ ID NO: 17 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 3 or SEQ ID NO: 17 and an hSyn promoter, CaMKII promoter, U6 promoter, or Pol III promoter.

Accordingly, an object of the disclosure relates to a vector comprising the sequence SEQ ID NO: 14 or SEQ ID NO: 18 and a promoter. In some embodiments, the vector comprises the sequence set forth in SEQ ID NO: 14 or SEQ ID NO: 18 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 14 or SEQ ID NO: 18 and an hSyn promoter, CamKII promoter, U6 promoter, or Pol III promoter.

Accordingly, an object of the disclosure relates to a vector comprising the sequence SEQ ID NO: 15 or SEQ ID NO: 19 and a promoter. In some embodiments, the vector comprises the sequence set forth in SEQ ID NO: 15 or SEQ ID NO: 19 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 15 or SEQ ID NO: 19 and an hSyn promoter, CaMKII promoter, U6 promoter, or a Pol III promoter.

Accordingly, an object of the disclosure relates to a vector comprising an antisense sequence of a corresponding region of the GluK2 receptor, or variants thereof and a CAG promoter (e.g., SEQ ID NO: 35).

Accordingly, an object of the disclosure relates to a vector comprising an antisense sequence of a corresponding region of the GluK2 receptor, or variants thereof and a CAG promoter.

Accordingly, an object of the disclosure relates to a vector comprising a miRNA sequence that targets a corresponding region of the GluK2 receptor, or variants thereof and a CAG promoter or a Pol II promoter.

Accordingly, an object of the disclosure relates to a vector comprising a shRNA sequence that targets a corresponding region of the GluK2 receptor, or variants thereof and a U6 (e.g., SEQ ID NO: 29) promoter or a Pol III promoter.

Accordingly, an object of the disclosure relates to a vector comprising a shmiRNA sequence that targets a corresponding region of the GluK2 receptor, or variants thereof and a U6 promoter or a Pol III promoter.

Accordingly, an object of the disclosure relates to a vector comprising the sequence SEQ ID NO: 1 and a CAG promoter.

Accordingly, an object of the disclosure relates to a vector comprising the sequence SEQ ID NO: 2 or SEQ ID NO: 16 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 2 or SEQ ID NO: 16 and a CAG promoter.

Accordingly, an object of the disclosure relates to a vector comprising the sequence SEQ ID NO: 3 or SEQ ID NO: 17 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 3 or SEQ ID NO: 17 and a CAG promoter.

Accordingly, an object of the disclosure relates to a vector comprising the sequence SEQ ID NO: 14 or SEQ ID NO: 18 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 14 or SEQ ID NO: 18 and a CAG promoter.

Accordingly, an object of the disclosure relates to a vector comprising the sequence SEQ ID NO: 15 or SEQ ID NO: 19 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 15 or SEQ ID NO: 19 and a CAG promoter.

Accordingly, an object of the disclosure relates to a vector comprising the sequence SEQ ID NO: 1 and a CaMKII promoter (e.g., any one of SEQ ID NOS: 30-34).

Accordingly, an object of the disclosure relates to a vector comprising the sequence SEQ ID NO: 2 or SEQ ID NO: 16 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 2 or SEQ ID NO: 16 and a CaMKII promoter.

Accordingly, an object of the disclosure relates to a vector comprising the sequence SEQ ID NO: 3 or SEQ ID NO: 17 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 3 or SEQ ID NO: 17 and a CaMKII promoter.

Accordingly, an object of the disclosure relates to a vector comprising the sequence SEQ ID NO: 14 or SEQ ID NO: 18 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 14 or SEQ ID NO: 18 and a CaMKII promoter.

Accordingly, an object of the disclosure relates to a vector comprising the sequence SEQ ID NO: 15 or SEQ ID NO: 19 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 15 or SEQ ID NO: 19 and a CaMKII promoter.

In particular examples, the expression vector or polynucleotide may include a nucleic acid sequence that encodes a stem and a loop which form a duplex stem-loop structure. For example, the expression vector or polynucleotide may include a nucleic acid sequence that encodes a loop region, in which the loop region may be derived in whole or in part from wild type microRNA sequence gene (e.g., miR-30) or be completely artificial. In a particular example, the loop region may be an miR-30 loop sequence. Furthermore, the stem-loop structure may include a guide sequence (e.g., an antisense RNA sequence, such as, e.g., any one of SEQ ID NOs: 14, 15, 18, or 19) and a passenger sequence (e.g., any one of SEQ ID NOs: 2, 3, 16, or 17) that is complementary to all or part of the guide sequence. For example, the passenger sequence may be complementary to all of the nucleotides of the guide sequence except for 10, 9, 8, 7, 6, 5, 4,3 2, or 1 nucleotide(s) of the guide sequence or the passenger sequence may be complementary to any one of SEQ ID NOS: 14, 15, 18, or 19.

Pre-miRNA or pri-miRNA scaffolds that include guide (i.e., antisense) sequences of the disclosure may be used in conjunction with the compositions and methods disclosed herein, for example, for use in construction of shmiRNA antisense agents. A pri-miRNA scaffold includes a pre-miRNA scaffold, and pri-miRNA may be 50-800 nucleotides in length (e.g., 50-800, 75-700, 100-600, 150-500, 200-400, or 250-300 nucleotides). In particular examples, the pre-miRNA may be 50-100 nucleotides (e.g., between 50-60, 60-70, 70-80, 80-90, or 90-100 nucleotides), 100-200 nucleotides (e.g., between 110-120, 120-130, 130-140, 140-150, 150-160, 160-170, 170-180, 180-190, or 190-200 nucleotides), 200-300 nucleotides (e.g., between 200-210, 210-220, 220-230, 230-240, 240-250, 250-260, 260-270, 270-280, 280-290, or 290-300 nucleotides), 300-400 nucleotides (e.g., between 300-310, 310-320, 320-330, 330-340, 340-350, 350-360, 360-370, 370-380, 380-390, or 390-400 nucleotides), 400-500 nucleotides (e.g., between 400-410, 410-420, 420-430, 430-440, 440-450, 450-460, 460-470, 470-480, 480-490, or 490-500 nucleotides), 500-600 nucleotides (e.g., between 500-510, 510-520, 520-530, 530-540, 540-550, 550-560, 560-570, 570-580, 580-590, or 590-600 nucleotides), 600-700 nucleotides (e.g., between 600-610, 610-620, 620-630, 630-640, 640-650, 650-660, 660-670, 670-680, 680-690, or 690-700 nucleotides), or 700-800 nucleotides (e.g., between 700-710, 710-720, 720-730, 730-740, 740-750, 750-760, 760-770, 770-780, 780-790, or 790-800 nucleotides). These engineered scaffolds allow processing of the pre-miRNA into a double stranded RNA comprising a guide sequence and a passenger sequence. As such, pre-miRNA includes a 5' arm including the sequence encoding a guide (i.e., antisense) RNA (e.g., any one of SEQ ID NOS: 14, 15, 18, or 19), a loop sequence usually derived from a wild-type miRNA (e.g., miR-30) and a 3' arm including a sequence encoding a passenger (i.e., sense) strand (e.g., any one of SEQ ID NOs: 2, 3, 16, 17) which is substantially complementary to the guide sequence. Pre-miRNA "stem-loop" sequences are generally longer than 50 nucleotides, e.g. 50-150 nucleotides (e.g., 50-60, 60-70, 70-80, 80-90, 90-100, 100-110, 110-120, 120-130, 130-140, or 140-150 nucleotides), 50-110 nucleotides (e.g., 50-60, 60-70, 70-80, 80-90, 90-100, 100-110 nucleotides), or 50-80 nucleotides (e.g., 50-60, 60-70, 70-80 nucleotides) in length. Pri-miRNA further includes 5' flanking and 3' flanking sequences, flanking the 5' and 3' arms, respectively. Flanking sequences are not necessarily contiguous with other sequences (the arm region or the guide sequence), are unstructured, unpaired regions, and may also be derived, in whole or in part, from one or more wild-type pri-miRNA scaffolds (e.g., pri-miRNA scaffolds derived, in whole or in part, from, e.g., miR-30). Flanking sequences are each at least 4 nucleotides in length, or up to 300 nucleotides or more in length (e.g., 4-300, 10-275, 20-250, 30-225, 40-200, 50-175, 60-150, 70-125, 80-100, or 90-95 nucleotides). Spacer sequences may be present as intervening between the aforementioned sequence structures, and in most instances provide linking polynucleotides, e.g., 1-30 nucleotides (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides), to provide flexibility without interfering with functionality to the overall pre-miRNA structure. The spacer may be derived from a naturally occurring linking group from a naturally occurring RNA, a portion of a naturally occurring linking group, a poly-A or poly-U/T, or a random sequence of nucleotides, so long as the spacer does not interfere with the processing of the double stranded RNA, nor does the spacer interfere with the binding/interaction of the guide RNA with the target mRNA sequence.

In some embodiments, the pre-miRNA may include a polynucleotide having a nucleic acid sequence encoded by any one of SEQ ID NOs: 20 or SEQ ID NO: 22 or a variant thereof having at least 85% (e.g., at least 90%, 95%, 96%, 97%, 98%, 99%, or more) sequence identity to the nucleic acid sequence of SEQ ID NOs: 20 or SEQ ID NO: 22.

In some embodiments, the pri-miRNA may include a polynucleotide having a nucleic acid sequence encoded by any one of SEQ ID NOs: 21 or SEQ ID NO: 23 or a variant thereof having at least 85% (e.g., at least 90%, 95%, 96%, 97%, 98%, 99%, or more) sequence identity to the nucleic acid sequence of SEQ ID NOs: 21 or SEQ ID NO: 23.

According to the methods and compositions disclosed herein, the expression vector or polynucleotide may encode (i) a 5' stem-loop arm including a guide (e.g., antisense) strand (e.g., any one of SEQ ID NOs: 14, 15, 18, or 19) and, optionally, a 5' spacer sequence upstream (i.e., 5') relative to the 5' stem-loop amm; a loop region/sequence, such as, e.g., a miR-30 loop sequence (e.g., SEQ ID NO: 23); and (iii) a 3' stem-loop arm including a passenger (e.g., sense) strand (e.g., any one of SEQ ID NOs: 2, 3, 16, or 17) and optionally a 3' spacer sequence downstream (i.e., 3') relative to the 3' stem-loop arm. In another example, the expression vector or polynucleotide including a nucleotide sequence may further encode (i) a 5' stem-loop arm including a passenger sequence (e.g., any one of SEQ ID NO: 2, 3, 16, or 17) and, optionally, a 5' spacer sequence upstream (i.e., 5') relative to the 5' stem-loop arm; a loop region/sequence; (ii) a loop region/sequence, such as, e.g., a miR-30 loop sequence (e.g., SEQ ID NO: 25); and (ii) a 3' stem-loop arm including a guide sequence (e.g., any one of SEQ ID NOs: 14, 15, 18, or 19) and optionally a 3' spacer sequence downstream (i.e., 3') relative to the 3' stem-loop arm. In a further example, the expression vector or polynucleotide includes a leading 5' flanking region (e.g., SEQ ID NO: 24) upstream of the guide sequence (e.g., any one of SEQ ID NOS: 14, 15, 18, or 19) and the flanking region may be of any length and may be derived in whole or in part from wild type microRNA sequence, may be heterologous or derived from a miRNA of different origin from the other flanking regions or the loop, or may be completely artificial. A 3' flanking region (e.g., SEQ ID NO: 26) may mirror the 5' flanking region in size and origin and the 3' flanking region may be downstream (i.e., 3') of the guide sequence. In yet another example, one or both of the 5' flanking sequence and the 3' flanking sequences are absent.

The expression vector or polynucleotide may include a nucleotide sequence that further encodes a first flanking region (e.g., a miR-30 flanking region), said first flanking region includes a 5' flanking sequence (e.g., SEQ ID NO: 24) and, optionally, a 5' spacer sequence. In a particular example, the first flanking region is located upstream (i.e., 5') to said passenger sequence. In another example, the expression vector or polynucleotide including a nucleotide sequence encodes a second flanking region (e.g., SEQ ID NO: 26), said second flanking region includes a 3' flanking sequence and, optionally, a 3' spacer sequence. In a particular example, the first flanking region is located 5' to the guide sequence.

According to the methods and compositions disclosed herein, the expression vector may include a polynucleotide sequence that encodes:

(a) a stem-loop sequence (e.g., SEQ ID NO: 20) including, from 5' to 3':
   (i) a 5' stem-loop arm including a guide nucleotide sequence which is at least 85% (e.g., at least 85%, 90%, 95%, 96%, 97%, 98%, 99%, or more) identical to SEQ ID NO: 14, 15, 18, or 19, particularly wherein the variant does not have the nucleic acid sequence of SEQ ID NOs: 1, 2, or 3;
   (ii) a microRNA loop region, in which the loop region includes a microRNA loop sequence (e.g. a microRNA loop sequence (e.g., miR-30 loop sequence of SEQ ID NO: 25); and
   (iii) a 3' stem-loop arm including a passenger nucleotide sequence (e.g., SEQ ID NO: 2, 3, 16, or 17) that is complementary or substantially complementary to the guide sequence, (b) a first flanking region (e.g., a miR-30 flanking region of SEQ ID NO: 24 or a variant thereof having at least 85% (e.g., at least 90%, 95%, 96%, 97%, 98%, 99%, or more) sequence identity to the nucleic acid sequence of SEQ ID NO: 24) located 5' to the guide sequence, in which the first flanking region includes a 5' flanking sequence and, optionally, a 5' spacer sequence; and (c) a second flanking region (e.g., a miR-30 flanking region of SEQ ID NO: 26 or a variant thereof having at least 85% (e.g., at least 90%, 95%, 96%, 97%, 98%, 99%, or more) sequence identity to the nucleic acid sequence of SEQ ID NO: 26) located 3' to the passenger sequence, in which the second flanking region includes a 3' flanking sequence and, optionally, a 3' spacer sequence.

In some embodiments, the expression construct includes a polynucleotide having a sequence of SEQ ID NO: 20 or a variant thereof having at least 85% (e.g., at least 90%, 95%, 96%, 97%, 98%, 99%, or more) sequence identity to the nucleic acid sequence of SEQ ID NO: 20, as is shown below.

(SEQ ID NO: 20)
TAAAACAGGCATTAGCTATGGGTAGTGAAGCCACAGATGCCCATAGCTA
ATGCCTGTTTTA

In some embodiments, the expression construct includes a polynucleotide having a sequence of SEQ ID NO: 21 or a variant thereof having at least 85% (e.g., at least 90%, 95%, 96%, 97%, 98%, 99%, or more) sequence identity to the nucleic acid sequence of SEQ ID NO: 21, as is shown below.

(SEQ ID NO: 21)
TCGACTAGGGATAACAGGGTAATTGTTTGAATGAGGCTTCAGTACTTTA
CAGAATCGTTGCCTGCACATCTTGGAAACACTTGCTGGGATTACTTCTT
CAGGTTAACCCAACAGAAGGCTCGAGAAGGTATATTGCTGTTGACAGTG
AGCGCTAAAACAGGCATTAGCTATGGGTAGTGAAGCCACAGATGCCCAT
AGCTAATGCCTGTTTTATTGCCTACTGCCTCGGAATTCAAGGGGCTACT
TTAGGAGCAATTATCTTGTTTACTAAAACTGAATACCTTGCTATCTCTT
TGATACATTTTTACAAAGCTGAATTAAAATGGTATAAATTATCAC

In another example, the expression vector or polynucleotide includes a nucleotide sequence that encodes:

(a) a stem-loop sequence (e.g., SEQ ID NO: 22) including, from 5' to 3':
   (i) a 5' stem-loop arm including a passenger nucleotide sequence (e.g., SEQ ID NO: 2, 3, 16, or 17) which is complementary or substantially complementary to the guide nucleotide sequence;
   (ii) a microRNA loop sequence (e.g. a miR-30 loop sequence of SEQ ID NO: 25); and
   (iii) a 3' stem-loop arm including a guide nucleotide sequence which is at least 85% (e.g., at least 90%, 95%, 96%, 97%, 98%, 99%, or more) identical to SEQ ID NO: 14, 15, 18, or 19, particularly wherein the variant does not have the nucleic acid sequence of SEQ ID NOS: 1, 2, or 3;
(b) a first flanking region (e.g., a miR-30 flanking region of SEQ ID NO: 24 or a variant thereof having at least 85% (e.g., at least 90%, 95%, 96%, 97%, 98%, 99%, or more) sequence identity to the nucleic acid sequence of SEQ ID NO: 24) located 5' to the guide sequence; and
(c) a second flanking region (e.g., a miR-30 flanking region of SEQ ID NO: 26 or a variant thereof having at least 85% (e.g., at least 90%, 95%, 96%, 97%, 98%, 99%, or more) sequence identity to the nucleic acid sequence of SEQ ID NO: 26) located 3' to the passenger sequence, in which the second flanking region includes a 3' flanking sequence and, optionally, a 3' spacer sequence.

In some embodiments, the expression construct includes a polynucleotide having a sequence of SEQ ID NO: 22 or a variant thereof having at least 85% (e.g., at least 90%, 95%, 96%, 97%, 98%, 99%, or more) sequence identity to the nucleic acid sequence of SEQ ID NO: 22, as is shown below.

(SEQ ID NO: 22)
CCCATAGCTAATGCCTGTTTTATAGTGAAGCCACAGATGTAAAACAGGC
ATTAGCTATGGG

In some embodiments, the expression construct includes a polynucleotide having a sequence of SEQ ID NO: 23 or a variant thereof having at least 85% (e.g., at least 90%, 95%, 96%, 97%, 98%, 99%, or more) sequence identity to the nucleic acid sequence of SEQ ID NO: 23, as is shown below.

(SEQ ID NO: 23)
TCGACTAGGGATAACAGGGTAATTGTTTGAATGAGGCTTCAGTACTTTA
CAGAATCGTTGCCTGCACATCTTGGAAACACTTGCTGGGATTACTTCTT
CAGGTTAACCCAACAGAAGGCTCGAGAAGGTATATTGCTGTTGACAGTG
AGCGCCCCATAGCTAATGCCTGTTTTATAGTGAAGCCACAGATGTAAAA
CAGGCATTAGCTATGGGTTGCCTACTGCCTCGGAATTCAAGGGGCTACT
TTAGGAGCAATTATCTTGTTTACTAAAACTGAATACCTTGCTATCTCTT
TGATACATTTTTACAAAGCTGAATTAAAATGGTATAAATTATCAC

Exemplary microRNA flanking and loop sequences suitable for use with the present disclosure are provided in Table 6, as is shown below.

TABLE 6

MicroRNA sequences for use with expression constructs of the disclosure

| MicroRNA sequence | SEQ ID NO | cDNA sequence |
|---|---|---|
| miR-30-A 5' flanking region/sequence | 24 | TCGACTAGGGATAACAGGGTAATTGTTTGAATGAGGCTTCAGTACT TTACAGAATCGTTGCCTGCACATCTTGGAAACACTTGCTGGGATTA CTTCTTCAGGTTAACCCAACAGAAGGCTC |
| miR-30-A loop region/sequence | 25 | TAGTGAAGCCACAGATG |
| miR-30-A 3' flanking region/sequence | 26 | AAGGGGCTACTTTAGGAGCAATTATOTTGTTTACTAAAACTGAATA CCTTGCTATCTCTTTGATACATTTTTACAAAGCTGAATTAAAATGGT ATAAATTATCAC |

The length of the aforementioned guide sequence and passenger sequence may be between 19-25 (e.g., 19, 20, 21, 22, 23, 24, or 25) nucleotides in length. In a particular example, the length of the guide sequence is 19 nucleotides. In another example, the length of the guide sequence is 20 nucleotides. In another example, the length of the guide sequence is 21 nucleotides. In another example, the length of the guide sequence is 22 nucleotides. In another example, the length of the guide sequence is 23 nucleotides. In another example, the length of the guide sequence is 24 nucleotides. In another example, the length of the guide sequence is 25 nucleotides. In a particular example, the length of the passenger sequence is 19 nucleotides. In another example, the length of the passenger sequence is 20 nucleotides. In another example, the length of the passenger sequence is 21 nucleotides. In another example, the length of the passenger sequence is 22 nucleotides. In another example, the length of the passenger sequence is 23 nucleotides. In another example, the length of the passenger sequence is 24 nucleotides. In another example, the length of the passenger sequence is 25 nucleotides.

Accordingly, the guide sequence (e.g., any one of SEQ ID NOs: 14, 15, 18, or 19) and passenger sequence (e.g., any one of SEQ ID NOs: 2, 3, 16, or 17) may fully or partially hybridize to form a stem-loop duplex that is between 7-25 (e.g., 7, 8, 9, 10, 11, 12, 13, 14, 15, 16, 17, 18, 19, 20, 21, 22, 23, 24, or 25) nucleotides in length. For example, the stem-loop structure between the guide sequence and the passenger sequence may be 7 nucleotides in length. In another example, the stem-loop structure between the guide sequence and the passenger sequence may be 8 nucleotides in length. In another example, the stem-loop structure between the guide sequence and the passenger sequence may be 9 nucleotides in length. In another example, the stem-loop structure between the guide sequence and the passenger sequence may be 10 nucleotides in length. In another example, the stem-loop structure between the guide sequence and the passenger sequence may be 11 nucleotides in length. In another example, the stem-loop structure between the guide sequence and the passenger sequence may be 12 nucleotides in length. In another example, the stem-loop structure between the guide sequence and the passenger sequence may be 13 nucleotides in length. In another example, the stem-loop structure between the guide sequence and the passenger sequence may be 14 nucleotides in length. In another example, the stem-loop structure between the guide sequence and the passenger sequence may be 15 nucleotides in length. In another example, the stem-loop structure between the guide sequence and the passenger sequence may be 16 nucleotides in length. In another example, the stem-loop structure between the guide sequence and the passenger sequence may be 17 nucleotides in length. In another example, the stem-loop structure between the guide sequence and the passenger sequence may be 18 nucleotides in length. In another example, the stem-loop structure between the guide sequence and the passenger sequence may be 19 nucleotides in length. In another example, the stem-loop structure between the guide sequence and the passenger sequence may be 20 nucleotides in length. In another example, the stem-loop structure between the guide sequence and the passenger sequence may be 21 nucleotides in length. In another example, the stem-loop structure between the guide sequence and the passenger sequence may be 22 nucleotides in length. In another example, the stem-loop structure between the guide sequence and the passenger sequence may be 23 nucleotides in length. In another example, the stem-loop structure between the guide sequence and the passenger sequence may be 24 nucleotides in length. In yet another example, the stem-loop structure between the guide sequence and the passenger sequence may be 25 nucleotides in length.

According to the disclosed methods and compositions, the stem-loop structure (e.g., SEQ ID NO: 20 or SEQ ID NO: 22) formed by the guide sequence (e.g., any one of SEQ ID NOs: 14, 15, 18, or 19) and passenger sequence (e.g., any one of SEQ ID NOs: 2, 3, 16, or 17) may include at least one (e.g., at least 1, 2, 3, 4, 5, 6, 7, 8, 9, 10, 11, 12, 13, 14, or 15) mismatch. For example, the stem-loop structure may contain 1 mismatch. In another example, the stem-loop structure contains 2 mismatches. In another example, the stem-loop structure contains 3 mismatches. In another example, the stem-loop structure contains 4 mismatches. In another example, the stem-loop structure contains 5 mismatches. In another example, the stem-loop structure contains 6 mismatches. In another example, the stem-loop structure contains 7 mismatches. In another example, the stem-loop structure contains 8 mismatches. In another example, the stem-loop structure contains 9 mismatches. In another example, the stem-loop structure contains 10 mismatches. In another example, the stem-loop structure contains 11 mismatches. In another example, the stem-loop structure contains 12 mismatches. In another example, the stem-loop structure contains 13 mismatches. In another example, the stem-loop structure contains 14 mismatches. In yet another example, the stem-loop structure contains 15 mismatches.

The variants include, for instance, naturally-occurring variants due to allelic variations between individuals (e.g., polymorphisms), alternative splicing forms, etc. The term variant also includes genes sequences of the disclosure from other sources or organisms. Variants are preferably substantially homologous to sequences according to the disclosure, e.g., exhibit a nucleotide sequence identity of typically at least about 75%, preferably at least about 85%, more preferably at least about 90%, more preferably at least about 95% with sequences of the disclosure. Variants of the genes of the disclosure also include nucleic acid sequences, which hybridize to a sequence as defined above (or a complementary strand thereof) under stringent hybridization conditions. Typical stringent hybridization conditions include temperatures above 30 °C, preferably above 35 °C, more preferably in excess of 42 °C, and/or salinity of less than about 500 mM, preferably less than 200 mM. Hybridization conditions may be adjusted by the skilled person by modifying the temperature, salinity and/or the concentration of other reagents such as SDS, SSC, etc.

In one embodiment, the vector use according to the disclosure is a non-viral vector or a viral vector.

In a particular embodiment, the non-viral vector may be a plasmid comprising a polynucleotide that encodes an antisense sequence that hybridizes to a corresponding region of an mRNA encoding the GluK2 receptor.

In another particular embodiment, the vector may be a viral vector.

Gene delivery viral vectors useful in the practice of the present disclosure can be constructed utilizing methodologies well known in the art of molecular biology. Typically, viral vectors carrying transgenes are assembled from polynucleotides encoding the transgene, suitable regulatory elements and elements necessary for production of viral proteins which mediate cell transduction.

The term "transgene" refers to the antisense oligonucleotide of the disclosure.

The terms "gene transfer" or "gene delivery" refer to methods or systems for reliably inserting foreign DNA into host cells. Such methods can result in transient expression of non-integrated transferred DNA, extrachromosomal replication and expression of transferred replicons (e.g., episomes), or integration of transferred genetic material into the genomic DNA of host cells.

Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO95/14785, WO96/22378, U.S. Pat. Nos. 5,882,877, 6,013,516, 4,861, 719, 5,278,056 and WO94/19478.

In a particular embodiment, the viral vector may be an adenoviral, a retroviral, a lentiviral, a herpesvirus or an adeno-associated virus (AAV) vectors.

In one embodiment, adeno-associated viral (AAV) vectors are employed.

Accordingly, an object of the disclosure relates to an adeno-associated virus (AAV) vector comprising an antisense sequence that encodes a corresponding region of the GluK2 receptor, or variants thereof.

In another embodiment, the adeno-associated virus (AAV) vector of the disclosure may comprise any variant of the antisense sequence of a corresponding region of the GluK2 receptor.

Accordingly, an object of the disclosure relates to an adeno-associated virus (AAV) vector comprising an antisense sequence of a corresponding region of the GluK2 receptor, or variants thereof.

Accordingly, an object of the disclosure relates to an adeno-associated virus (AAV) vector comprising a shRNA sequence that targets a corresponding region of the GluK2 receptor, or variants thereof.

Accordingly, an object of the disclosure relates to an adeno-associated virus (AAV) vector comprising a miRNA sequence that targets a corresponding region of the GluK2 receptor, or variants thereof.

Accordingly, an object of the disclosure relates to an adeno-associated virus (AAV) vector comprising a shmiRNA sequence that targets a corresponding region of the GluK2 receptor, or variants thereof.

Accordingly, an object of the disclosure relates to an adeno-associated virus (AAV) vector comprising the sequence SEQ ID NO: 1 that encodes a corresponding region of the GluK2 receptor, or variants thereof.

Accordingly, an object of the disclosure relates to an adeno-associated virus (AAV) vector comprising the sequence SEQ ID NO: 2 that encodes a corresponding region of the GluK2 receptor, or variants thereof.

Accordingly, an object of the disclosure relates to an adeno-associated virus (AAV) vector comprising the sequence SEQ ID NO: 3 that encodes a corresponding region of the GluK2 receptor, or variants thereof.

In another embodiment, the adeno-associated virus (AAV) vector of the disclosure may comprise any variant of the sequence SEQ ID NO: 1 which encodes a corresponding region of the GluK2 receptor, or variants thereof.

In another embodiment, the adeno-associated virus (AAV) vector of the disclosure may comprise any variant of the sequence SEQ ID NO: 2 which encodes a corresponding region of the GluK2 receptor, or variants thereof.

In another embodiment, the adeno-associated virus (AAV) vector of the disclosure may comprise any variant of the sequence SEQ ID NO: 3 which encodes a corresponding region of the GluK2 receptor, or variants thereof.

Accordingly, an object of the disclosure relates to an adeno-associated virus (AAV) vector comprising the sequence SEQ ID NO: 14 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 14 that is complementary (i.e., antisense) to a corresponding region of the mRNA sequence encoding a GluK2 receptor, or variants thereof, particularly wherein the variant does not have the nucleic acid sequence of SEQ ID NOs: 1, 2, or 3.

Accordingly, an object of the disclosure relates to an adeno-associated virus (AAV) vector comprising the sequence SEQ ID NO: 15 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 15 that is complementary (i.e., antisense) to a corresponding region of the mRNA sequence encoding a GluK2 receptor, or variants thereof, particularly wherein the variant does not have the nucleic acid sequence of SEQ ID NOs: 1, 2, or 3.

Accordingly, an object of the disclosure relates to an adeno-associated virus (AAV) vector comprising an antisense sequence of a corresponding region of the GluK2 receptor, or variants thereof and an hSyn promoter (e.g., SEQ ID NO: 27 or SEQ ID NO: 28).

Accordingly, an object of the disclosure relates to an adeno-associated virus (AAV) vector comprising an antisense sequence of a corresponding region of the GluK2 receptor, or variants thereof and an hSyn promoter.

Accordingly, an object of the disclosure relates to an adeno-associated virus (AAV) vector comprising a miRNA sequence that targets a corresponding region of the GluK2 receptor, or variants thereof and an hSyn promoter.

Accordingly, an object of the disclosure relates to an adeno-associated virus (AAV) vector comprising a shRNA sequence that targets a corresponding region of the GluK2 receptor, or variants thereof and an hSyn promoter.

Accordingly, an object of the disclosure relates to an adeno-associated virus (AAV) vector comprising a shmiRNA sequence that targets a corresponding region of the GluK2 receptor, or variants thereof and an hSyn promoter.

Accordingly, an object of the disclosure relates to an adeno-associated virus (AAV) vector comprising the sequence SEQ ID NO: 1 and an hSyn promoter.

Accordingly, an object of the disclosure relates to an adeno-associated virus (AAV) vector comprising the sequence SEQ ID NO: 2 and an hSyn promoter.

Accordingly, an object of the disclosure relates to an adeno-associated virus (AAV) vector comprising the sequence SEQ ID NO: 3 and an hSyn promoter.

Accordingly, an object of the disclosure relates to an adeno-associated virus (AAV) vector comprising the sequence SEQ ID NO: 14 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 14 and an hSyn promoter.

Accordingly, an object of the disclosure relates to an adeno-associated virus (AAV) vector comprising the sequence SEQ ID NO: 15 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 15 and an hSyn promoter.

Accordingly, an object of the disclosure relates to an AAV vector comprising an antisense sequence of a corresponding region of the GluK2 receptor, or variants thereof and a CaMKII promoter (e.g., any one of SEQ ID NOs: 30-34).

Accordingly, an object of the disclosure relates to an AAV vector comprising an antisense sequence that targets a corresponding region of the GluK2 receptor, or variants thereof and a CaMKII promoter.

Accordingly, an object of the disclosure relates to an AAV vector comprising a miRNA sequence that targets a corresponding region of the GluK2 receptor, or variants thereof and a CaMKII promoter.

Accordingly, an object of the disclosure relates to an AAV vector comprising a shRNA sequence that targets a corresponding region of the GluK2 receptor, or variants thereof and a CaMKII promoter.

Accordingly, an object of the disclosure relates to an AAV vector comprising a shmiRNA sequence that targets a corresponding region of the GluK2 receptor, or variants thereof and a CaMKII promoter.

Accordingly, an object of the disclosure relates to an AAV vector comprising the sequence SEQ ID NO: 1 and a CaMKII promoter.

Accordingly, an object of the disclosure relates to an AAV vector comprising the sequence SEQ ID NO: 2 and a CaMKII promoter.

Accordingly, an object of the disclosure relates to an AAV vector comprising the sequence SEQ ID NO: 3 and a CaMKII promoter.

Accordingly, an object of the disclosure relates to an AAV vector comprising the sequence SEQ ID NO: 14 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 14 and a CaMKII promoter.

Accordingly, an object of the disclosure relates to an AAV vector comprising the sequence SEQ ID NO: 15 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 15 and a CaMKII promoter.

Accordingly, an object of the disclosure relates to an adeno-associated virus (AAV) vector comprising an antisense sequence of a corresponding region of the GluK2 receptor, or variants thereof and a CAG promoter (e.g., SEQ ID NO: 35).

Accordingly, an object of the disclosure relates to an adeno-associated virus (AAV) vector comprising an antisense sequence that targets a corresponding region of the GluK2 receptor, or variants thereof and a CAG promoter.

Accordingly, an object of the disclosure relates to an adeno-associated virus (AAV) vector comprising a miRNA sequence that targets a corresponding region of the GluK2 receptor, or variants thereof and a CAG promoter.

Accordingly, an object of the disclosure relates to an adeno-associated virus (AAV) vector comprising a shRNA sequence that targets a corresponding region of the GluK2 receptor, or variants thereof and a CAG promoter.

Accordingly, an object of the disclosure relates to an adeno-associated virus (AAV) vector comprising a shmiRNA sequence that targets a corresponding region of the GluK2 receptor, or variants thereof and a CAG promoter.

Accordingly, an object of the disclosure relates to an adeno-associated virus (AAV) vector comprising the sequence SEQ ID NO: 1 and a CAG promoter.

Accordingly, an object of the disclosure relates to an adeno-associated virus (AAV) vector comprising the sequence SEQ ID NO: 2 and a CAG promoter.

Accordingly, an object of the disclosure relates to an adeno-associated virus (AAV) vector comprising the sequence SEQ ID NO: 3 and a CAG promoter.

Accordingly, an object of the disclosure relates to an adeno-associated virus (AAV) vector comprising the sequence SEQ ID NO: 14 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 14 and a CAG promoter.

Accordingly, an object of the disclosure relates to an adeno-associated virus (AAV) vector comprising the sequence SEQ ID NO: 15 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 15 and a CAG promoter.

In one embodiment, the AAV vector is AAV1, AAV2, AAV3, AAV4, AA5, AAV6, AAV7, AAV8, AAV9, AAV10, AAVrh. 10 or any other serotypes of AAV that can infect human, rodents, monkeys or other species.

In a more embodiment, the AAV vector is an AAV9.

By an "AAV vector" is meant a vector derived from an adeno-associated virus serotype, including without limitation, AAV-1, AAV-2, AAV-3, AAV-4, AAV-5, AAV6, AAV7, AAV8, AAV9, AAV10, AAVrh. 10, etc. AAV vectors can have one or more of the AAV wild-type genes deleted in whole or part, e.g., the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. ITRs do not need to be the wild-type polynucleotide sequences, and may be altered, e.g., by the insertion, deletion or substitution of nucleotides, so long as the sequences provide for functional rescue, replication and packaging. AAV expression vectors are constructed using known techniques to at least provide as operatively linked components in the direction of transcription, control elements including a transcriptional initiation region, the DNA of interest (i.e., the nucleic acid sequences of the disclosure) and a transcriptional termination region.

In certain embodiments the viral vectors utilized in the compositions and methods of the disclosure are recombinant adeno-associated virus (rAAV). The rAAV may be of any serotype, modification, or derivative, known in the art, or any combination thereof (e.g., a population of rAAV that comprises two or more serotypes, e.g., comprising two or more of rAAV2, rAAV8, and rAAV9) known in the art. In some embodiments, the rAAV are rAAV1, rAAV2, rAAV3, rAAV4, rAAV5, rAAV6, rAAV7, rAAV8, rAAV9, rAAV10, rAAV-11, rAAV-12, rAAV-13, rAAV-14, rAAV-15, rAAV-16, rAAV.rh8, rAAV.rh10, rAAV.rh20, rAAV.rh39, rAAV.Rh74, rAAV.RHM4-1, AAV.hu37, rAAV.Anc80, rAAV.Anc80L65, rAAV.7m8, rAAV.PHP.B, rAAV2.5, rAAV2tYF, rAAV3B, rAAV.LK03, rAAV.HSC1, rAAV.HSC2, rAAV.HSC3, rAAV.HSC4, rAAV.HSC5, rAAV.HSC6, rAAV.HSC7, rAAV.HSC8, rAAV.HSC9, rAAV.HSC10, rAAV.HSC11, rAAV.HSC12, rAAV.HSC13, rAAV.HSC14, rAAV.HSC15, or rAAV.HSC16, or other rAAV, or combinations of two or more thereof.

In some embodiments, the rAAV used in the compositions and methods of the disclosure comprise a capsid protein from an AAV capsid serotype selected from AAV1, AAV2, AAV3, AAV4, AAV5, AAV6, AAV7, AAV8, AAV9, AAV10, AAV-11, AAV-12, AAV-13, AAV-14, AAV-15, AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV21YF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16, or a derivative, modification, or pseudotype thereof. In some embodiments, the rAAV comprise a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e., up to 100% identical, to e.g., vp1, vp2 and/or vp3 sequence of an AAV capsid serotype selected from AAV1, AAV2, AAV3, AAV4, AAV5, AAV6, AAV7, AAV8, AAV9, AAV10, AAV-11, AAV-12, AAV-13, AAV-14, AAV-15, AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2YF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In certain embodiments, the AAV that is used in the methods described herein is Anc80 or Anc80L65, as described in Zinn et al., 2015:1056-1068, which is incorporated by reference in its entirety. In certain embodiments, the AAV that is used in the methods described herein comprises one of the following amino acid insertions: LGETTRP (SEQ ID NO: 14 of '956, '517, '282, or '323) or LALGETTRP (SEQ ID NO: 15 of '956, '517, '282, or '323), as described in U.S. Pat. Nos. 9,193,956; 9,458,517; and 9,587,282 and US patent application publication no. 2016/0376323, each of which is incorporated herein by reference in its entirety. In certain embodiments, the AAV that is used in the methods described herein is AAV.7m8, as described in U.S. Pat. Nos. 9,193,956; 9,458,517; and 9,587,282 and US patent application publication no. 2016/0376323, each of which is incorporated herein by reference in its entirety. In certain embodiments, the AAV that is used in the methods described herein is any AAV disclosed in U.S. Pat. No. 9,585,971, such as AAV-PHP.B. In certain embodiments, the AAV that is used in the methods described herein is any AAV disclosed in U.S. Pat. No. 9,840,719 and WO 2015/013313, such as AAV.Rh74 and RHM4-1, each of which is incorporated herein by reference in its entirety. In certain embodiments, the AAV that is used in the methods described herein is any AAV disclosed in WO 2014/172669, such as AAV rh.74, which is incorporated herein by reference in its entirety. In certain embodiments, the AAV that is used in the methods described herein is AAV2/5, as described in Georgiadis et al., 2016, Gene Therapy 23:857-862 and Georgiadis et al., 2018, Gene Therapy 25:450, each of which is incorporated by reference in its entirety. In certain embodiments, the AAV that is used in the methods described herein is any AAV disclosed in WO 2017/070491, such as AAV2tYF, which is incorporated herein by reference in its entirety. In certain embodiments, the AAV that is used in the methods described herein is AAVLK03 or AAV3B, as described in Puzzo et al., 2017, Sci. Transl. Med. 29 (9): 418, which is incorporated by reference in its entirety. In certain embodiments, the AAV that is used in the methods described herein is any AAV disclosed in U.S. Pat. Nos. 8,628,966; 8,927,514; 9,923,120 and WO 2016/049230, such as HSC1, HSC2, HSC3, HSC4, HSC5, HSC6, HSC7, HSC8, HSC9, HSC10, HSC11, HSC12, HSC13, HSC14, HSC15, or HSC16, each of which is incorporated by reference in its entirety.

In certain embodiments, the AAV that is used in the methods described herein is an AAV disclosed in any of the following patents and patent applications, each of which is incorporated herein by reference in its entirety: U.S. Pat. Nos. 7,282,199; 7,906,111; 8,524,446; 8,999,678; 8,628,966; 8,927,514; 8,734,809; U.S. Pat. Nos. 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; and International Patent Application Nos. PCT/US2015/034799; PCT/EP2015/053335. In some embodiments, the rAAV have a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e., up to 100% identical, to the vp1, vp2 and/or vp3 sequence of an AAV capsid disclosed in any of the following patents and patent applications, each of which is incorporated herein by reference in its entirety: United States Patent Nos. 7,282, 199; 7,906, 111; 8,524,446; 8,999,678; 8,628,966; 8,927,514; 8,734,809; U.S. Pat. Nos. 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; and International Patent Application Nos. PCT/US2015/034799; PCT/EP2015/053335.

In some embodiments, the rAAV has a capsid protein disclosed in Intl. Appl. Publ. No. WO 2003/052051 (see, e.g., SEQ ID NO: 2 of '051), WO 2005/033321 (see, e.g., SEQ ID NOs: 123 and 88 of '321), WO 03/042397 (see, e.g., SEQ ID NOs: 2, 81, 85, and 97 of '397), WO 2006/068888 (see, e.g., SEQ ID NOs: 1 and 3-6 of '888), WO 2006/110689, (see, e.g., SEQ ID NOs: 5-38 of '689) WO2009/104964 (see, e.g., SEQ ID NOs: 1-5, 7, 9, 20, 22, 24 and 31 of '964), WO 2010/127097 (see, e.g., SEQ ID NOs: 5-38 of '097), and WO 2015/191508 (see, e.g., SEQ ID NOs: 80-294 of '058), and U.S. Appl. Publ. No. 20150023924 (see, e.g., SEQ ID NOs: 1, 5-10 of '924), the contents of each of which is herein incorporated by reference in its entirety, such as, e.g., an rAAV vector having a capsid protein that is at least 80% or more identical, e.g., 85%, 85%, 87%, 88%, 89%, 90%, 91%, 92%, 93%, 94%, 95%, 96%, 97%, 98%, 99%, 99.5%, or more to the vp1, vp2 and/or vp3 amino acid sequence of an AAV capsid disclosed in Intl. Appl. Publ. No. WO 2003/052051 (see, e.g., SEQ ID NO: 2 of '051), WO 2005/033321 (see, e.g., SEQ ID NOs: 123 and 88 of '321), WO 03/042397 (see, e.g., SEQ ID NOs: 2, 81, 85, and 97 of '397), WO 2006/068888 (see, e.g., SEQ ID NOs: 1 and 3-6 of '888), WO 2006/110689 (see, e.g., SEQ ID NOs: 5-38 of '689) WO2009/104964 (see, e.g., SEQ ID NOs: 1-5, 7, 9, 20, 22, 24 and 31 of '964), WO 2010/127097 (see, e.g., SEQ ID NOs: 5-38 of '097), and WO 2015/191508 (see, e.g., SEQ ID NOs: 80-294 of '508), and U.S. Appl. Publ. No. 20150023924 (see, e.g., SEQ ID NOs: 1, 5-10 of '924).

Nucleic acid sequences of AAV based viral vectors and methods of making recombinant AAV and AAV capsids are taught, for example, in U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; International Patent Application Nos. PCT/US2015/034799; PCT/EP2015/053335; WO 2003/052051, WO 2005/033321, WO 03/042397, WO 2006/068888, WO 2006/110689, WO2009/104964, WO 2010/127097, and WO 2015/191508, and U.S. Appl. Publ. No. 20150023924.

In additional embodiments, the rAAV comprise a pseudotyped rAAV. In some embodiments, the pseudotyped rAAV are rAAV2/8 or rAAV2/9 pseudotyped rAAV. Methods for producing and using pseudotyped rAAV are known in the art (see, e.g., Duan et al., J. Virol., 75:7662-7671 (2001); Halbert et al., J. Virol., 74:1524-1532 (2000); Zolotukhin et al., Methods 28:158-167 (2002); and Auricchio et al., Hum. Molec. Genet. 10:3075-3081, (2001).

In additional embodiments, the rAAV comprise a capsid containing a capsid protein chimeric of two or more AAV capsid serotypes. In some embodiments, the capsid protein is a chimeric of 2 or more AAV capsid proteins from AAV serotypes selected from AAV1, AAV2, AAV3, AAV4, AAV5, AAV6, AAV7, AAV8, AAV9, AAV10, AAV-11, AAV-12, AAV-13, AAV-14, AAV-15, AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV21YF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In certain embodiments, a single-stranded AAV (ssAAV) can be used. In certain embodiments, a self-complementary vector, e.g., scAAV, can be used (see, e.g., Wu, 2007, Human Gene Therapy, 18 (2): 171-82, McCarty et al, 2001, Gene Therapy, Vol. 8, Number 16, Pages 1248-1254; and U.S. Pat. Nos. 6,596,535; 7,125,717; and 7,456,683, each of which is incorporated herein by reference in its entirety). In certain embodiments, the recombinant AAV vector used for delivering the transgene (e.g., a heterologous polynucleotide encoding an antisense oligonucleotide of the disclosure) have a tropism for cells in the CNS, including but not limited to neurons and/or glial cells. Such vectors can include non-replicating "rAAV", particularly those bearing an AAV9 or AAVrh10 capsid are preferred. In certain embodiments, the viral vectors provided herein are AAV9 or AAVrh10 based viral vectors. In certain embodiments, the AAV9 or AAVrh10 based viral vectors provided herein retain tropism for CNS cells. AAV variant capsids can be used, including but not limited to those described by Wilson in U.S. Pat. No. 7,906,111 which is incorporated by reference herein in its entirety, with AAV/hu.31 and AAV/hu.32 being particularly preferred; as well as AAV variant capsids described by Chatterjee in U.S. Pat. Nos. 8,628,966, 8,927,514 and Smith et al. (Mol Ther 22:1625-1634, 2014), each of which is incorporated by reference herein in its entirety.

In some embodiment, the present disclosure relates to a recombinant adeno-associated virus (rAAV) comprising (i) an expression cassette containing a transgene under the control of regulatory elements and flanked by ITRs, and (ii) an AAV capsid, wherein the transgene encodes an inhibitory RNA that specifically binds (e.g., hybridizes) to Grik2 mRNA and inhibits expression of Grik2 in a cell.

Provided in particular embodiments are AAV9 vectors comprising an artificial genome comprising (i) an expression cassette containing the transgene under the control of regulatory elements and flanked by ITRs; and (ii) a viral capsid that has the amino acid sequence of the AAV9 capsid protein or is at least 95%, 96%, 97%, 98%, 99% or 99.9% identical to the amino acid sequence of the AAV9 capsid protein while retaining the biological function of the AAV9 capsid. In certain embodiments, the encoded AAV9 capsid has the sequence of SEQ ID NO: 123 set forth in U.S. Pat. No. 7,906,111 which is incorporated by reference herein in its entirety, with 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid substitutions and retaining the biological function of the AAV9 capsid.

Provided in particular embodiments are AAVrh10 vectors comprising an artificial genome comprising (i) an expression cassette containing the transgene (e.g., a heterologous polynucleotide encoding an antisense oligonucleotide of the disclosure) under the control of regulatory elements and flanked by ITRs; and (ii) a viral capsid that has the amino acid sequence of the AAVrh10 capsid protein or is at least 95%, 96%, 97%, 98%, 99% or 99.9% identical to the amino acid sequence of the AAVrh10 capsid protein while retaining the biological function of the AAVrh10capsid. In certain embodiments, the encoded AAVrh10 capsid has the sequence of SEQ ID NO: 81 set forth in U.S. Pat. No. 9,790,427 which is incorporated by reference herein in its entirety, with 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid substitutions and retaining the biological function of the AAVrh10 capsid.

The control elements are selected to be functional in a mammalian cell. The resulting construct which contains the operatively linked components is flanked by (5' and 3') functional AAV ITR sequences. By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a polynucleotide sequence interposed between two flanking ITRs into a mammalian cell genome. The polynucleotide sequences of AAV ITR regions are known. An "AAV ITR" does not necessarily comprise the wild-type polynucleotide sequence, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAV6, AAV7, AAV8, AAV9, AAV10, AAVrh. 10, etc. Furthermore, 5' and 3' ITRs which flank a selected polynucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell. Additionally, AAV ITRs may be derived from any of several AAV serotypes, including without limitation, AAV-1, AAV-2, AAV-3, AAV-4, AAV 5, AAV6, AAV7, AAV8, AAV9, AAV10, AAVrh. 10, etc. Furthermore, 5' and 3' ITRs which flank a selected polynucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

Particular embodiments are vectors derived from AAV serotypes having tropism for and high transduction efficiencies in cells of the mammalian CNS, particularly neurons. A review and comparison of transduction efficiencies of different serotypes is provided in this patent application. In certain examples, AAV2, AAV5, AAV9 and rh. 10 based vectors direct long-term expression of transgenes (e.g., heterologous polynucleotides encoding an antisense oligonucleotide of the disclosure) in CNS, preferably transducing neurons.

The selected polynucleotide sequence is operably linked to control elements that direct the transcription or expression thereof in the subject in vivo. Such control elements can comprise control sequences normally associated with the selected gene.

Typically, the vector of the present disclosure comprises an expression cassette. The term "expression cassette" refers to a nucleic acid construct comprising nucleic acid elements sufficient for the expression of the nucleic acid molecule of the present disclosure. Typically, the nucleic acid molecule encodes a heterologous gene and may also include suitable regulatory elements. The heterologous gene refers to a transgene that encodes an RNA of interest.

One or more expression cassettes may be employed. Each expression cassette may comprise at least a promoter sequence operably linked to a sequence encoding the RNA of interest. Each expression cassette may consist of additional regulatory elements, spacers, introns, UTRs, polyadenylation site, and the like. In some embodiments, the expression cassette is polycistronic with respect to the transgenes encoding e.g., two or more miRNAs. In other embodiments the expression cassette comprises a promoter, a nucleic acid encoding one or more RNA molecules of interest, and a polyA. In further embodiments, the expression cassette comprises 5'-promoter sequence, a sequence encoding a first RNA of interest, a sequence encoding a second RNA of interest, and a polyadenylation sequence-3'.

In some embodiments, an expression cassette may comprise additional elements, for example, an intron, an enhancer, a polyadenylation site, a woodchuck posttranscriptional response element (WPRE), and/or other elements known to affect expression levels of the encoding sequence. Typically, an expression cassette comprises the nucleic acid molecule of the present disclosure operatively linked to a promoter sequence.

The term "operatively linked" refers to the association of two or more nucleic acid fragments on a single nucleic acid fragment so that the function of one is affected by the other.

For example, a promoter is operatively linked with a coding sequence when it is capable of affecting the expression of that coding sequence (e.g., the coding sequence is under the transcriptional control of the promoter). Encoding sequences can be operatively linked to regulatory sequences in sense or antisense orientation.

The term "promoter" sequence refers to a polynucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

In some embodiments, the promoter is a heterologous promoter. The term "heterologous promoter" refers to a promoter that is not found to be operatively linked to a given encoding sequence in nature.

Useful heterologous control sequences generally include those derived from sequences encoding mammalian or viral genes. Examples include, but are not limited to, the phosphoglycerate kinase (PGK) promoter, CAG (composite of the (CMV) cytomegalovirus enhancer the chicken beta actin promoter (CBA) and the rabbit beta globin intron), U6 promoter, neuronal promoters (Human synapsin 1 (hSyn) promoter, NeuN promoters, CamKII promoter, promoter of Dopamine-1 receptor and Dopamine-2 receptor), the SV40 early promoter, mouse mammary tumor virus LTR promoter; adenovirus major late promoter (Ad MLP); a herpes simplex virus (HSV) promoter, a CMV promoter such as the CMV immediate early promoter region (CMV-IE), Rous sarcoma virus (RSV) promoter, synthetic promoters, hybrid promoters, and the like. In addition, sequences derived from non-viral genes, such as the murine metallothionein gene, will also find use herein. Such promoter sequences are commercially available from, e.g., Stratagene (San Diego, CA). Examples of CNS specific promoters include those isolated from the genes of neuron specific enolase (NSE). Example of dentate gyrus selective promoters include the promoter of the Clql2, POMC and prox1 genes.

For purposes of the present disclosure, both heterologous promoters and other control elements, such as CNS-specific and inducible promoters, enhancers and the like, will be of particular use.

An "enhancer" is a polynucleotide sequence that can stimulate promoter activity and may be an innate element of the promoter or a heterologous element inserted to enhance the level or tissue-specificity of a promoter. In some embodiments, the promoter is derived in its entirety from a native gene. In some embodiments, the promoter is composed of different elements derived from different naturally occurring promoters. In some embodiments, the promoter comprises a synthetic polynucleotide sequence. It will be understood by those skilled in the art that different promoters will direct the expression of a gene in different tissues or cell types, or at different stages of development, or in response to different environmental conditions or to the presence or the absence of a drug or transcriptional co-factor. Ubiquitous, cell-type-specific, tissue-specific, developmental stage-specific, and conditional promoters, for example, drug-responsive promoters (e.g., tetracycline-responsive promoters) are well known to those of skill in the art.

In mammalian systems, three kinds of promoters exist and are candidates for construction of the expression vectors: Pol I promoters control transcription of large ribosomal RNAs; Pol II promoters control the transcription of mRNAs (that are translated into protein) and small nuclear RNAs (snRNAs); and Pol III promoters uniquely transcribe small non-coding RNAs. Each has advantages and constraints to consider when designing the construct for expression of the RNAs in vivo. For example, Pol III promoters are useful for synthesizing small interfering RNAs (e.g., shRNAs) from DNA templates in vivo. For greater control over tissue specific expression, Pol II promoters are preferred but can only be used for transcription of miRNAs. When a Pol II promoter is used, however, it may be preferred to omit translation initiation signals so that the RNAs function as antisense, siRNA, shRNA, miRNAs, shmiRNA and are not translated into peptides in vivo.

The AAV expression vector which harbors the DNA molecule of interest flanked by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art (see, e.g., U.S. Pat. Nos. 5,173,414 and 5,139,941; International Publications Nos. WO 92/01070 (published 23 Jan. 1992) and WO 93/03769 (published 4 Mar. 1993)). Alternatively, AAV ITRs can be excised from the viral genome or from an AAV vector containing the same and fused 5' and 3'of a selected nucleic acid construct that is present in another vector using standard ligation techniques. AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226. Additionally, chimeric genes can be produced synthetically to include AAV ITR sequences arranged 5'and 3' of one or more selected nucleic acid sequences. Preferred codons for expression of the chimeric gene sequence in mammalian CNS cells can be used, and in certain embodiments codon optimization of the transgene (e.g., a heterologous polynucleotide encoding an antisense oligonucleotide of the disclosure) is performed by well-known methods. The complete chimeric sequence is assembled from overlapping oligonucleotides prepared by standard methods. In order to produce AAV virions, an AAV expression vector is introduced into a suitable host cell using known techniques, such as by transfection. A number of transfection techniques are generally known in the art. Particularly suitable transfection methods include calcium phosphate co-precipitation, direct microinjection into cultured cells, electroporation, liposome mediated gene transfer, lipid-mediated transduction, and nucleic acid delivery using high-velocity microprojectiles.

For instance, a particular viral vector comprises, in addition to a nucleic acid sequence of the disclosure, the backbone of AAV vector plasmid with ITR derived from AAV-2, the promoter, such as the mouse PGK (phosphoglycerate kinase) gene or the cytomegalovirus/β-actin hybrid promoter (CAG) consisting of the enhancer from the CMV immediate gene, the promoter, splice donor and intron from the chicken β-actin gene, the splice acceptor from rabbit β-globin, or any neuronal promoter such as the promoter of Dopamine-1 receptor or Dopamine-2 receptor, or the synapsin promoter, with or without the wild-type or mutant form of woodchuck hepatitis virus post-transcriptional regulatory element (WPRE), and a rabbit beta-globin polyA sequence. The viral vector may comprise in addition, a nucleic acid sequence encoding an antibiotic resistance gene such as the genes of resistance ampicillin (AmpR), kanamycin, hygromycin B, geneticin, blasticidin S or puromycin.

In one embodiment, retroviral vectors are employed.

Retroviruses may be chosen as gene delivery vectors due to their ability to integrate their genes into the host genome, transferring a large amount of foreign genetic material, infecting a broad spectrum of species and cell types and for being packaged in special cell-lines. In order to construct a retroviral vector, a nucleic acid encoding a gene of interest is inserted into the viral genome in the place of certain viral sequences to produce a virus that is replication-defective. In order to produce virions, a packaging cell line is constructed containing the gag, pol, and/or env genes but without the LTR and/or packaging components. When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types.

In another embodiment, lentiviral vectors are employed.

Accordingly, an object of the disclosure relates to a lentivirus vector comprising an oligonucleotide sequence that encoding a corresponding region of the GluK2 receptor, or variants thereof.

In another embodiment, the lentivirus vector of the disclosure may comprise any variant of the antisense sequence of a corresponding region of the GluK2 receptor.

In another embodiment, the lentivirus vector of the disclosure may comprise any variant of the antisense sequence of for any variant of the GluK2 receptor.

Accordingly, an object of the disclosure relates to a lentivirus vector comprising an antisense sequence that targets a corresponding region of the GluK2 receptor, or variants thereof.

Accordingly, an object of the disclosure relates to a lentivirus vector comprising a shRNA sequence that targets a corresponding region of the GluK2 receptor, or variants thereof.

Accordingly, an object of the disclosure relates to a lentivirus vector comprising a miRNA sequence that targets a corresponding region of the GluK2 receptor, or variants thereof.

Accordingly, an object of the disclosure relates to a lentivirus vector comprising a shmiRNA sequence that targets a corresponding region of the GluK2 receptor, or variants thereof.

Accordingly, an object of the disclosure relates to a lentivirus vector comprising the sequence SEQ ID NO: 1 that encodes a corresponding region of the GluK2 receptor, or variants thereof.

Accordingly, an object of the disclosure relates to a lentivirus vector comprising the sequence SEQ ID NO: 16 that encodes a corresponding region of the GluK2 receptor, or variants thereof having at least 85% (e.g., at least 90%, 91%, 92%, 93%, 94%, 95%, 96%, 97%, 98%, 99%, or more) sequence identity to the nucleic acid sequence of SEQ ID NO: 16.

Accordingly, an object of the disclosure relates to a lentivirus vector comprising the sequence SEQ ID NO: 17 that encodes a corresponding region of the GluK2 receptor, or variants thereof having at least 85% (e.g., at least 90%, 91%, 92%, 93%, 94%, 95%, 96%, 97%, 98%, 99%, or more) sequence identity to the nucleic acid sequence of SEQ ID NO: 17.

Accordingly, an object of the disclosure relates to a lentivirus vector comprising the sequence SEQ ID NO: 18 that hybridizes to a sequence encoding a corresponding region of the GluK2 receptor, or variants thereof having at least 85% (e.g., at least 90%, 91%, 92%, 93%, 94%, 95%, 96%, 97%, 98%, 99%, or more) sequence identity to the nucleic acid sequence of SEQ ID NO: 18.

Accordingly, an object of the disclosure relates to a lentivirus vector comprising the sequence SEQ ID NO: 19 that hybridizes to a sequence encoding a corresponding region of the GluK2 receptor, or variants thereof having at least 85% (e.g., at least 90%, 91%, 92%, 93%, 94%, 95%, 96%, 97%, 98%, 99%, or more) sequence identity to the nucleic acid sequence of SEQ ID NO: 19.

In another embodiment, the lentivirus vector of the disclosure may comprise any variant of the sequence SEQ ID NO: 1 which encodes a corresponding region of the GluK2 receptor.

In another embodiment, the lentivirus vector of the disclosure may comprise any variant of the sequence SEQ ID NO: 16 which encodes for any variant of a corresponding region of the GluK2 receptor or variants thereof having at least 85% (e.g., at least 90%, 91%, 92%, 93%, 94%, 95%, 96%, 97%, 98%, 99%, or more) sequence identity to the nucleic acid sequence of SEQ ID NO: 16.

In another embodiment, the lentivirus vector of the disclosure may comprise any variant of the sequence SEQ ID NO: 17 which encodes for any variant of a corresponding region of the GluK2 receptor or variants thereof having at least 85% (e.g., at least 90%, 91%, 92%, 93%, 94%, 95%, 96%, 97%, 98%, 99%, or more) sequence identity to the nucleic acid sequence of SEQ ID NO: 17.

Accordingly, an object of the disclosure relates to a lentivirus vector comprising an antisense sequence of a corresponding region of the GluK2 receptor, or variants thereof and an hSyn promoter (e.g., SEQ ID NO: 27 or SEQ ID NO: 28).

Accordingly, an object of the disclosure relates to a lentivirus vector comprising an antisense sequence that targets a corresponding region of the GluK2 receptor, or variants thereof and an hSyn promoter.

Accordingly, an object of the disclosure relates to a lentivirus vector comprising a miRNA sequence that targets a corresponding region of the GluK2 receptor, or variants thereof and an hSyn promoter.

Accordingly, an object of the disclosure relates to a lentivirus vector comprising a shRNA sequence that targets a corresponding region of the GluK2 receptor, or variants thereof and an hSyn promoter.

Accordingly, an object of the disclosure relates to a lentivirus vector comprising a shmiRNA sequence that targets a corresponding region of the GluK2 receptor, or variants thereof and an hSyn promoter.

Accordingly, an object of the disclosure relates to a lentivirus vector comprising an antisense sequence of a corresponding region of the GluK2 receptor, or variants thereof and a CaMKII promoter (e.g., any one of SEQ ID NOs: 30-34).

Accordingly, an object of the disclosure relates to a lentivirus vector comprising an antisense sequence that targets a corresponding region of the GluK2 receptor, or variants thereof and a CaMKII promoter.

Accordingly, an object of the disclosure relates to a lentivirus vector comprising a miRNA sequence that targets a corresponding region of the GluK2 receptor, or variants thereof and a CaMKII promoter.

Accordingly, an object of the disclosure relates to a lentivirus vector comprising a shRNA sequence that targets a corresponding region of the GluK2 receptor, or variants thereof and a CaMKII promoter.

Accordingly, an object of the disclosure relates to a lentivirus vector comprising a shmiRNA sequence that targets a corresponding region of the GluK2 receptor, or variants thereof and a CaMKII promoter.

Accordingly, an object of the disclosure relates to a lentivirus vector comprising the sequence SEQ ID NO: 1 and a CaMKII promoter.

Accordingly, an object of the disclosure relates to a lentivirus vector comprising the sequence SEQ ID NO: 16 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 16 and a CaMKII promoter.

Accordingly, an object of the disclosure relates to a lentivirus vector comprising the sequence SEQ ID NO: 17 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 17 and a CaMKII promoter.

Accordingly, an object of the disclosure relates to a lentivirus vector comprising the sequence SEQ ID NO: 18 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 18 and a CaMKII promoter.

Accordingly, an object of the disclosure relates to a lentivirus vector comprising the sequence SEQ ID NO: 19 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 19 and a CaMKII promoter.

Accordingly, an object of the disclosure relates to a lentivirus vector comprising a shRNA sequence that targets a corresponding region of the GluK2 receptor, or variants thereof and a U6 promoter (e.g., SEQ ID NO: 29)

Accordingly, an object of the disclosure relates to a lentivirus vector comprising a miRNA sequence that targets a corresponding region of the GluK2 receptor, or variants thereof and a CaMKII promoter.

Accordingly, an object of the disclosure relates to a lentivirus vector comprising a shmiRNA sequence that targets a corresponding region of the GluK2 receptor, or variants thereof and a CaMKII promoter.

Accordingly, an object of the disclosure relates to a lentivirus vector comprising the sequence SEQ ID NO: 1 and a U6 promoter (e.g., SEQ ID NO: 29).

Accordingly, an object of the disclosure relates to a lentivirus vector comprising the sequence SEQ ID NO: 16 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 16 and a U6 promoter.

Accordingly, an object of the disclosure relates to a lentivirus vector comprising the sequence SEQ ID NO: 17 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 17 and a U6 promoter.

Accordingly, an object of the disclosure relates to a lentivirus vector comprising the sequence SEQ ID NO: 18 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 18 and a U6 promoter.

Accordingly, an object of the disclosure relates to a lentivirus vector comprising the sequence SEQ ID NO: 19 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 19 and a U6 promoter.

Accordingly, an object of the disclosure relates to a lentivirus vector comprising an antisense sequence of a corresponding region of the GluK2 receptor, or variants thereof and a CAG promoter (e.g., SEQ ID NO: 35).

Accordingly, an object of the disclosure relates to a lentivirus vector comprising an antisense sequence that targets a corresponding region of the GluK2 receptor, or variants thereof and a CAG promoter.

Accordingly, an object of the disclosure relates to a lentivirus vector comprising a miRNA sequence that targets a corresponding region of the GluK2 receptor, or variants thereof and a CAG promoter.

Accordingly, an object of the disclosure relates to a lentivirus vector comprising a shRNA sequence that targets a corresponding region of the GluK2 receptor, or variants thereof and a CAG promoter.

Accordingly, an object of the disclosure relates to a lentivirus vector comprising a shmiRNA sequence that targets a corresponding region of the GluK2 receptor, or variants thereof and a CAG promoter.

Accordingly, an object of the disclosure relates to a lentivirus vector comprising the sequence SEQ ID NO: 1 and a CAG promoter.

Accordingly, an object of the disclosure relates to a lentivirus vector comprising the sequence SEQ ID NO: 16 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 16 and a CAG promoter.

Accordingly, an object of the disclosure relates to a lentivirus vector comprising the sequence SEQ ID NO: 17 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 17 and a CAG promoter.

Accordingly, an object of the disclosure relates to a lentivirus vector comprising the sequence SEQ ID NO: 18 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 18 and a CAG promoter.

Accordingly, an object of the disclosure relates to a lentivirus vector comprising the sequence SEQ ID NO: 19 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 19 and a CAG promoter.

Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses (HIV1, HIV2) and the Simian Immunodeficiency Virus (SIV). Lentiviral vectors have been generated by multiply attenuating the HIV virulence genes, for example, the genes env, vif, vpr, vpu and nef are deleted making the vector biologically safe. Lentiviral vectors are known in the art, see, e.g., U.S. Pat. Nos. 6,013,516 and 5,994,136, both of which are incorporated herein by reference. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest. Recombinant lentivirus capable of infecting a non-dividing cell wherein a suitable host cell is transfected with two or more vectors carrying the packaging functions, namely gag, pol and env, as well as rev and tat at is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene into that packaging cell yields a producer cell which releases infectious viral particles carrying the foreign gene of interest. The env preferably is an amphotropic envelope protein which allows transduction of cells of human and other species. Typically, the nucleic acid molecule or the vector of the present disclosure include "control sequences", which refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

In a particular embodiment, the vector of the disclosure contains a nucleic acid sequence that encodes GluK2 receptor, including GluK2 isoforms 1 to 7 (e.g., SEQ ID NOs: 4 to 10, respectively).

Modulation of GluK2 Receptor Activity

An ionotropic glutamate receptor activity that exhibits fast gating by glutamate, acts by opening a cation channel permeable to sodium and potassium, and for which kainate is an agonist. Kainate selective receptor complexes can form when several subunits, multimers e.g., heteromers or homomers, of kainate receptors assemble to form a structure with an extracellular N-terminus and a large loop that together form the ligand binding domain. The C-terminus of such a complex is intracellular. The ionotropic glutamate receptor complex itself acts as a ligand gated ion channel, and upon binding glutamate, charged ions pass through a channel in the receptor complex. Kainate receptors are multimeric assemblies of GluK1, 2 and/or 3 (also called GluR5, R6 and R7), GluK4 (KA1) and GluK5 (KA2) subunits (Collingridge, Neuropharmacology. 2009 January; 56 (1): 2-5). GluK2 containing kainate receptors (which terms may be used interchangeably in most cases with GluK2 receptor and GluK2 subunit to generally refer to the protein encoded by or expressed by a Grik2 gene) are targets for modulation of ionotropic glutamate receptor activity and subsequently amelioration of symptoms related to epileptogenesis.

Epileptogenesis, which leads to the establishment of epilepsy, may appear latent while cellular and molecular changes that lead to neuronal network reorganization occur. Because plastic responses of the CNS seem to depend on both the developmental state and the regional susceptibility, not all subjects with brain injuries develop epilepsy. The hippocampus, including the dentate gyrus, has been identified as an epileptic brain region susceptible to damage, is associated with temporal lobe epilepsy (TLE), and, in some instances, has been attributed with refractory epilepsy (resistant to treatment) (Jarero-Basulto, J. J., et al. *Pharmaceuticals,* 2018, 11, 17; doi: 10.3390/ph11010017). An amplification of excitatory glutamatergic components may facilitate spontaneous epileptiform seizures (Kuruba, et al. Epilepsy Behav. 2009, 14 (Suppl. 1), 65-73). Chemical glutamate inhibitors (antagonists), for example NMDA receptor antagonists, have been shown to block or reduce neuronal death by Glu-mediated excitotoxicity and acute seizure generation, however, have poor efficacy in TLE (Foster, A C, and Kemp, J A. *Curr. Opin. Pharmacol.* 2006, 6, 7-17). The siRNAs disclosed herein, however, have been shown in the examples, to decrease the expression of GluK2-containing KARs in neurons and remarkably prevent spontaneous epileptiform discharges in a model of TLE.

In one embodiment, the oligonucleotide encoding a corresponding region of the Grik2 gene, or variants thereof, decreases or inhibits epileptiform discharges, or decreases the frequency of epileptiform discharges. In another embodiment, a vector comprising an oligonucleotide encoding a corresponding region of the Grik2 gene, or variants thereof.

In some embodiments, the oligonucleotide encoding a corresponding region of the Grik2 gene, or variants thereof, or a vector comprising the oligonucleotide, is capable of reducing the expression level of GluK2 in hippocampal cells, including cells of the dentate gyrus.

In other embodiments, a method is provided for reducing epileptiform discharges in a CNS cell comprising providing to the cell an effective amount of a synthetic RNA molecule encoded by a nucleic acid that targets and binds (e.g., hybridizes) to a nucleic acid sequence comprising or consisting of any one of SEQ ID NOs: 2, 3, 16, or 17.

In other embodiments, a method is provided for reducing epileptiform discharges in a CNS cell comprising providing to the cell an effective amount of a synthetic RNA molecule encoded by a nucleic acid comprising SEQ ID NO: 14 or SEQ ID NO: 18 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 14 or SEQ ID NO: 18, particularly wherein the variant does not have the nucleic acid sequence of SEQ ID NOs: 1, 2, or 3.

In other embodiments, a method is provided for reducing epileptiform discharges in a CNS cell comprising providing to the cell an effective amount of a synthetic RNA molecule encoded by a nucleic acid comprising SEQ ID NO: 15 or SEQ ID NO: 19 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 15 or SEQ ID NO: 19, particularly wherein the variant does not have the nucleic acid sequence of SEQ ID NOs: 1, 2, or 3.

Short-term neuronal synaptic plasticity generally involves increasing or decreasing synaptic sensitivity, and may encompass a process that modulates the ability of neuronal synapses to change in the short-term. Long-term neuronal plasticity generally involves increasing or decreasing numbers of synapses, and may encompass a process that modulates the ability of neuronal synapses to change in the long-term. In some embodiments, the antisense oligonucleotide that binds (e.g., hybridizes) to a corresponding region of the Grik2 mRNA or variants thereof, or a vector comprising the oligonucleotide, is capable of reducing the neuronal expression level of GluK2 leading to the reduction in the frequency of epileptiform discharges in cortical structures including (but not restricted to) the hippocampus (including the dentate gyrus).

Method for Treating Epilepsy

Accordingly, an object of the present disclosure relates to a method for treating epilepsy in a subject in need thereof, wherein the method comprises: administering an effective amount of a vector comprising an oligonucleotide encoding an inhibitory RNA that binds (e.g., hybridizes) specifically to Grik2 mRNA and inhibits expression of Grik2 in the subject. In other words, the disclosure relates to a vector comprising an oligonucleotide encoding an inhibitory RNA that binds (e.g., hybridizes) specifically to Grik2 mRNA and inhibits expression of Grik2 for use in the treatment of epilepsy.

Accordingly, an object of the present disclosure relates to a method of treating epilepsy disease in a subject in need thereof comprising administering to the subject a therapeutically effective amount of an antisense agent according to the disclosure. In other words, the disclosure provides an antisense agent for use in the treatment of an epilepsy disease. In a particular example, the antisense agent comprises or consists of SEQ ID NO: 14 or SEQ ID NO: 18 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 14 or SEQ ID NO: 18, particularly wherein the variant does not have the nucleic acid sequence of SEQ ID NOs: 1, 2, or 3. In another example, the antisense agent comprises or consists of SEQ ID NO: 15 or SEQ ID NO: 19 or a variant thereof having at least 85% (e.g., at least 90%, 91%, 92%, 93%, 94%, 95%, 96%, 97%, 98%, 99%, or more) sequence identity to the nucleic acid sequence of SEQ ID NO: 15 or SEQ ID NO: 19, particularly wherein the variant does not have the nucleic acid sequence of SEQ ID NOS: 1, 2, or 3.

Accordingly, an object of the present disclosure relates to a method of treating epilepsy disease in a subject in need thereof comprising administering to the subject a therapeutically effective amount of a vector comprising an antisense agent according to the disclosure.

In particular, the disclosure relates to a method of treating epilepsy disease in a subject in need thereof comprising administering to the subject a therapeutically effective amount of a vector comprising an antisense agent according to the disclosure and a promoter according to the disclosure.

The term "subject" denotes a mammal, such as a rodent, a feline, a canine, and a primate. Particularly, the subject according to the disclosure is a human, a mouse or a rat. More particularly, the subject according to the disclosure has or is susceptible to epilepsy. The term "subject" encompasses "patient".

The term "epilepsy" can be classified according the electroclinical syndromes following the Classification and Terminology of the International League Against Epilepsy (ILAE) [Berg et al., 2010]. These syndromes can be categorized by age at onset, distinctive constellations (surgical syndromes), and structural-metabolic causes: (A) age at onset: (i) neonatal period includes Benign familial neonatal epilepsy (BFNE), Early myoclonic encephalopathy (EME), Ohtahara syndrome. (ii) Infancy period includes Epilepsy of infancy with migrating focal seizures, West syndrome, Myoclonic epilepsy in infancy (MEI), Benign infantile epilepsy, Benign familial infantile epilepsy, Dravet syndrome, Myoclonic encephalopathy in nonprogressive disorders. (iii) Childhood period includes Febrile seizures plus (FS+), Panayiotopoulos syndrome, Epilepsy with myoclonic atonic (previously astatic) seizures, Benign epilepsy with centrotemporal spikes (BECTS), Autosomal-dominant nocturnal frontal lobe epilepsy (ADNFLE), Late onset childhood occipital epilepsy (Gastaut type), Epilepsy with myoclonic absences, Lennox-Gastaut syndrome, Epileptic encephalopathy with continuous spike-and-wave during sleep (CSWS), Landau-Kleffner syndrome (LKS), Childhood absence epilepsy (CAE). (iv) Adolescence-Adult period includes Juvenile absence epilepsy (JAE) Juvenile myoclonic epilepsy (JME), Epilepsy with generalized tonic-clonic seizures alone, Progressive myoclonus epilepsies (PME), Autosomal dominant epilepsy with auditory features (ADEAF), Other familial temporal lobe epilepsies. (v) Variable age onset includes Familial focal epilepsy with variable foci (childhood to adult), Reflex epilepsies. (B) Distinctive constellations (surgical syndromes) include Mesial Temporal Lobe Epilepsy (MTLE), Rasmussen syndrome, Gelastic seizures with hypothalamic hamartoma, Hemiconvulsion-hemiplegia-epilepsy. (C) Epilepsies attributed to and organized by structural-metabolic causes include Malformations of cortical development (hemimegalencephaly, heterotopias, etc.), Neurocutaneous syndromes (tuberous sclerosis complex,Sturge-Weber, etc.), Tumor, Infection, Trauma, Angioma, Perinatal insults, Stroke, Etc.

In another embodiment, the epilepsy may be a benign Rolandic epilepsy, a frontal lobe epilepsy, an infantile spasms, a juvenile myoclonic epilepsy, a juvenile absence epilepsy, a childhood absence epilepsy (pyknolepsy), a hot water epilepsy, a Lennox-Gastaut syndrome, a Landau-Kleffner syndrome, a Dravet syndrome, a progressive myoclonus epilepsies, a reflex epilepsy, a Rasmussen's syndrome, a temporal lobe epilepsy, a limbic epilepsy, a status epilepticus, an abdominal epilepsy, a massive bilateral myoclonus, a catamenial epilepsy, a Jacksonian seizure disorder, a Lafora disease or photosensitive epilepsy.

In a particular embodiment, the epilepsy is a temporal lobe epilepsy.

In one embodiment, the epilepsy is a chronic epilepsy.

In another embodiment, the epilepsy can be a drug-resistant (i.e., refractory) epilepsy.

The term "refractory epilepsy" denotes an epilepsy which is refractory to current pharmaceutical treatment; that is to say that current pharmaceutical treatment does not allow an effective treatment of patients' disease (see for example Dario J. Englot et al., 2013).

In a particular embodiment, the refractory epilepsy is a chronic refractory epilepsy.

The term "Temporal Lobe Epilepsy" or "TLE" denotes a chronic neurological condition characterized by chronic and recurrent seizures (epilepsy) which originate in the temporal lobe of the brain. This disease is different from acute seizures in naïve brain tissue since in TLE morpho-functional reorganization of neuronal network and sprouting of hippocampal mossy fibers appears whereas in acute seizures in naïve tissue such reorganization is not present.

The term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria (e.g., disease manifestation, etc.)).

Electroencephalography (EEG) assesses electrical brain function and is complementary to the neuroimaging techniques, e.g., functional MRI (fMRI), single-photon emission computed tomography (SPECT), and positron emission tomography (PET), that can assess anatomical brain changes. EEG provides a continuous measure of cortical function with time resolution, and detection of interictal (period between seizures) epileptiform discharges is also informative in a diagnostic setting.

For the treatment of epilepsy, and to ameliorate the symptoms of seizures and epileptiform discharges as discussed supra, a useful transgene may be deployed by a vector which encodes a functional RNA, e.g., shRNA, miRNA, or shmiRNA that inhibits the expression of Grik2.

Methods of delivery of vectors to neurons and/or astrocytes of the subject includes generally any method suitable for delivery vectors to the neurons and/or astrocytes such that at least a portion of cells of a selected synaptically connected cell population is transduced. Vectors may be delivered to any cells of the central nervous system, or both. Generally, the vector is delivered to the cells of the central nervous system, including for example cells of the spinal cord, brainstem (medulla, pons, and midbrain), cerebellum, diencephalon (thalamus, hypothalamus), telencephalon (corpus striatum, cerebral cortex, or, within the cortex, the occipital, temporal, parietal or frontal lobes), or combinations thereof, or preferably any suitable subpopulation thereof. Further preferred sites for delivery include the ruber nucleus, corpus amygdaloideum, entorhinal cortex and neurons in ventralis lateralis, or to the anterior nuclei of the thalamus.

In a particular embodiment, vectors of the disclosure are delivered by stereotactic injections or microinjections directly in the brain. In other embodiments, the vectors of the disclosure may be administered by intravenous injection, for example in the context of vectors that exhibit tropism for CNS tissues, including but not limited to AAV9 or AAVrh10.

To deliver vectors of the disclosure specifically to a particular region and to a particular population of cells of the CNS, vectors may be administered by stereotaxic microinjection. For example, subjects have the stereotactic frame base fixed in place (screwed into the skull). The brain with stereotactic frame base (MRI compatible with fiducial markings) is imaged using high resolution MRI. The MRI images are then transferred to a computer which runs stereotactic software. A series of coronal, sagittal and axial images are used to determine the target (site of AAV vector injection or lentivirus vector injection) and trajectory. The software directly translates the trajectory into 3 dimensional coordinates appropriate for the stereotactic frame. Holes are drilled above the entry site and the stereotactic apparatus positioned with the needle implanted at the given depth. The AAV vector or the lentivirus vector are then injected at the target sites. Since the AAV vector or the lentivirus vector integrate into the target cells, rather than producing viral particles, the subsequent spread of the vector is minor, and mainly a function of passive diffusion from the site of injection and of course the desired transsynaptic transport, prior to integration. The degree of diffusion may be controlled by adjusting the ratio of vector to fluid carrier.

Additional routes of administration may also comprise local application of the vector under direct visualization, e.g., superficial cortical application, or other non-stereotactic application. The vector may be delivered intrathecally, in the ventricles or by intravenous injection.

In one example, the method of the disclosure comprises intracerebral administration through stereotaxic injections. However, other known delivery methods may also be adapted in accordance with the disclosure. For example, for a more widespread distribution of the vector across the CNS, it may be injected into the cerebrospinal fluid, e.g., by lumbar puncture. To direct the vector to the peripheral nervous system, it may be injected into the spinal cord or into the peripheral ganglia, or the flesh (subcutaneously or intramuscularly) of the body part of interest. In certain situations, the vector can be administered via an intravascular approach. For example, the vector can be administered intra-arterially (carotid) in situations where the blood-brain barrier is disturbed or not disturbed. Moreover, for more global delivery, the vector can be administered during the "opening" of the blood-brain barrier achieved by infusion of hypertonic solutions including mannitol.

Vectors used herein may be formulated in any suitable vehicle for delivery. For instance, they may be placed into a pharmaceutically acceptable suspension, solution or emulsion. Suitable mediums include saline and liposomal preparations. More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Intravenous vehicles include fluid and nutrient replenishers, electrolyte replenishers (such as those based on Ringer's dextrose), and the like.

Preservatives and other additives may also be present such as, for example, antimicrobials, antioxidants, chelating agents, and inert gases and the like.

A colloidal dispersion system may also be used for targeted gene delivery. Colloidal dispersion systems include macromolecule complexes, nanocapsules, microspheres, beads, and lipid-based systems including oil-in-water emulsions, micelles, mixed micelles, and liposomes.

Accordingly, an object of the present disclosure relates to a composition comprising an antisense agent according to the disclosure.

In particular, the present disclosure relates to a composition comprising a vector comprising an antisense according to the disclosure.

In particular, the present disclosure relates to a composition comprising a vector comprising an antisense agent according to the disclosure and a promoter according to the disclosure.

In some embodiments, the present disclosure relates to a pharmaceutical composition comprising an adeno-associated viral (AAV) vector comprising:

(a) a viral capsid; and (b) an artificial genome comprising an expression cassette flanked by AAV inverted terminal repeats (ITRs), wherein the expression cassette comprises a transgene encoding an oligonucleotide that binds (e.g., hybridizes) to Grik2 mRNA, operably one or more regulatory sequences that control expression of the transgene (e.g., a heterologous polynucleotide encoding an antisense oligonucleotide of the disclosure) in CNS cells.

In some embodiments, the expression cassette has a general structure including the following elements oriented in a 5' to 3' direction:

(i) A 5' ITR sequence;

(ii) a promoter sequence (e.g., a promoter having a sequence of any one of the promoters disclosed herein);

(iii) a 5' flanking sequence (a miR-30 5' flanking sequence; e.g., SEQ ID NO: 24);

(iv) a stem-loop sequence (e.g., SEQ ID NO: 20 or SEQ ID NO: 22) that includes in the 5' to 3' direction:

a. a stem-loop 5' arm, in which the stem-loop 5' arm includes a guide sequence containing at least a nucleic acid sequence of SEQ ID NOS: 14, 15, 18, or 19, or a passenger sequence (e.g., having a sequence of SEQ ID NOs: 2, 3, 16, or 17) that is fully or partially complementary (e.g., containing no more than 5, no more than 4, no more than 3, no more than 2, or no more than 1 mismatched nucleotides) to the nucleic acid sequence of SEQ ID NOs: 14, 15, 18, or 19;

b. a loop sequence (e.g., a miR-30 loop sequence; e.g., SEQ ID NO: 25); and c. a stem-loop 3' arm, in which the stem-loop 3' arm includes a guide sequence containing at least a nucleic acid sequence of SEQ ID NOS: 14, 15, 18, or 19 or a passenger sequence (e.g., having a sequence of SEQ ID NOs: 2, 3, 16, or 17) that is fully or partially complementary (e.g., containing no more than 5, no more than 4, no more than 3, no more than 2, or no more than 1 mismatch) to the nucleic acid sequence of SEQ ID NOs: 14, 15, 18, or 19;

(v) a 3' flanking sequence (a miR-30 3' flanking sequence; e.g., SEQ ID NO: 26);

(vi) optionally, a WPRE sequence;

(vii) a polyA sequence; and (viii) a 3' ITR sequence.

In a particular example, the passenger sequence (e.g., SEQ ID: NOS: 2, 3, 16, or 17) that is fully or partially complementary to the nucleic acid sequence of the guide sequence (e.g., SEQ ID: NO: 14, 15, 18, or 19) has no more than 5 (e.g., no more than 5, 4, 3, 2, or 1) mismatched nucleotides (i.e., mismatches) relative to the nucleic acid sequence of SEQ ID NOS: 14, 15, 18, or 19. In another example, the passenger sequence (e.g., SEQ ID: NOS: 2, 3, 16, or 17) that is fully or partially complementary to the nucleic acid sequence of the guide sequence (e.g., SEQ ID: NO: 14, 15, 18, or 19) has no more than 4 (e.g., no more than 4, 3, 2, or 1) mismatched nucleotides (i.e., mismatches) relative to the nucleic acid sequence of SEQ ID NOs: 14, 15, 18, or 19. In another example, the passenger sequence (e.g., SEQ ID: NOS: 2, 3, 16, or 17) that is fully or partially complementary to the nucleic acid sequence of the guide sequence (e.g., SEQ ID: NO: 14, 15, 18, or 19) has no more than 3 (e.g., no more than 3, 2, or 1) mismatched nucleotides (i.e., mismatches) relative to the nucleic acid sequence of SEQ ID NOS: 14, 15, 18, or 19. In another example, the passenger sequence (e.g., SEQ ID: NOS: 2, 3, 16, or 17) that is fully or partially complementary to the nucleic acid sequence of the guide sequence (e.g., SEQ ID: NO: 14, 15, 18, or 19) has no more than 2 (e.g., no more than 2 or 1) mismatched nucleotides (i.e., mismatches) relative to the nucleic acid sequence of SEQ ID NOs: 14, 15, 18, or 19. In yet another example, the passenger sequence (e.g., SEQ ID: NOS: 2, 3, 16, or 17) that is fully or partially complementary to the nucleic acid sequence of the guide sequence (e.g., SEQ ID: NO: 14, 15, 18, or 19) has no more than 1 mismatched nucleotide (i.e., mismatches) relative to the nucleic acid sequence of SEQ ID NOs: 14, 15, 18, or 19.

The antisense agent as described above may be combined with pharmaceutically acceptable excipients, and optionally sustained-release matrices, such as biodegradable polymers, to form pharmaceutical compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The pharmaceutical compositions of the present disclosure for oral, sublingual, subcutaneous, intramuscular, intravenous, transdermal, local or rectal administration, the active principle, alone or in combination with another active principle, can be administered in a unit administration form, as a mixture with conventional pharmaceutical supports, to subjects, such as animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the disclosure as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The polypeptide (or nucleic acid encoding thereof) can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Prolonged absorption of the injectable compositions can be brought about by the use in the compositions of agents delaying absorption, for example, aluminum monostearate and gelatin. Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation may be vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

Further Embodiments are Listed in the Following

1. A recombinant antisense oligonucleotide that targets a Grik2 mRNA.

2. An oligonucleotide comprising or consisting of a nucleotide sequence selected from SEQ ID NO: 1, SEQ ID NO: 2, and SEQ ID NO: 3.

3. The antisense oligonucleotide according to embodiment 1, wherein the antisense oligonucleotide is capable of reducing the amount of GluK2 containing kainate receptors in neurons.

4. A vector for delivery of a heterologous nucleic acid, wherein the nucleic acid encodes an inhibitory RNA that specifically binds Grik2 mRNA and inhibits expression of Grik2 in a cell.

5. The vector according to embodiment 3, wherein the vector is a recombinant adeno-associated viral (rAAV) vector, lentiviral vector, or retroviral vector.

6. A recombinant adeno-associated virus (rAAV) comprising (i) an expression cassette containing a transgene under the control of regulatory elements and flanked by ITRs, and (ii) an AAV capsid, wherein the transgene encodes an inhibitory RNA that specifically binds Grik2 mRNA and inhibits expression of Grik2 in a cell.

7. The rAAV according to embodiment 5, wherein the transgene comprises an antisense sequence complimentary to mRNA encoding GluK2 receptor.

8. A recombinant adeno-associated virus (rAAV) comprising the nucleic acid sequence set forth in SEQ ID NO: 1.

9. The rAAV according to any one of embodiments 5 to 7, wherein the transgene is under the control of a promoter.

10. The rAAV according to any one of embodiments 5 to 9, wherein the AAV capsid is AAV9 or AAVrh10.

11. A method for treating epilepsy in a subject in need thereof, wherein the method comprises: administering an effective amount of a vector comprising an oligonucleotide encoding an inhibitory RNA that binds specifically to Grik2 mRNA and inhibits expression of Grik2 in the subject.

12. The method according to embodiment 11, wherein the oligonucleotide encodes a siRNA, shRNA, antisense RNA or miRNA.

13. The method according to embodiment 11, wherein the vector comprises a nucleotide sequence selected from SEQ ID NO: 1, SEQ ID NO: 2, and SEQ ID NO: 3.

14. The method according to any one of embodiments 11 to13, wherein the epilepsy is temporal lobe epilepsy, a chronic epilepsy, and/or a refractory epilepsy.

15. A pharmaceutical composition comprising an adeno-associated viral (AAV) vector comprising:

a) a viral capsid; and b) an artificial genome comprising an expression cassette flanked by AAV inverted terminal repeats (ITRs), wherein the expression cassette comprises a transgene encoding an oligonucleotide that binds Grik2 mRNA, operably one or more regulatory sequences that control expression of the transgene in CNS cells.

16. The composition according to embodiment 14, wherein the viral capsid is encoded by a nucleic acid sequence that encodes a capsid protein that is at least 95% identical to an AAV9 or AAVrh10 capsid amino acid sequence.

The above embodiments relate to gene therapy targeting GluK2 subunit that can be used to inhibit epileptiform discharges. An RNA sequence (e.g. aaarcaggcattagctatg, wherein "r" represents an adenine or a guanine; SEQ ID NO: 1) is described.

The disclosure will be further illustrated by the following figures and examples. However, these examples and figures should not be interpreted in any way as limiting the scope of the present disclosure.

BRIEF DESCRIPTION OF THE FIGURES

(FIG. 1A) Plasmid map of an LV-control vector (LV104) encoding a scrambled control sequence. (FIG. 1B) Plasmid map of an LV vector encoding a Grik2 antisense sequence (SEQ ID NO: 14) as an shRNA (LV173). (FIG. 1C) Plasmid map of an LV vector encoding a Grik2 antisense sequence (SEQ ID NO: 14) as a microRNA (LV178) (FIG. 1D) Bar graphs illustrating the relative GluK2 expression (mean±s.e.m.) of protein lysates harvested from rat primary hippocampal cultures following treatment with different viral vectors compared with control condition without infection (p-value versus control).

(FIG. 3A) Plasmid map of an AAV9-hu1010 vector including an expression cassette that contains from 5' to 3': a 5' inverted terminal repeat (ITR), human synapsin (hSyn) promoter (SEQ ID NO: 27 or SEQ ID NO: 28), a mir-30 5' flanking sequence (SEQ ID NO: 24), 5' stem-loop arm containing an antisense guide sequence (SEQ ID NO: 14), a mir-30 loop sequence (SEQ ID NO: 25), a 3' stem-loop arm containing a sense passenger sequence (SEQ ID NO: 2), a 3' flanking sequence (SEQ ID NO: 26), a rabbit globin polyA signal, a stuffer DNA, and a 3' ITR. (FIG. 3B) Bar graphs illustrating the effect of AAV9-hu1010 compared with control conditions (AAV9-scramble) on the frequency of epileptiform discharges in mouse organotypic hippocampal slices. Note the similar effects observed in slices treated with AAV9-hu1010 compared with GluK2−/−slices. The symbols *,  and * denote significance of $P<0.05$, $P<0.01$ and $P<0.001$.

EXAMPLES

Example 1

Material & Methods

Ethics

Figure 1A:
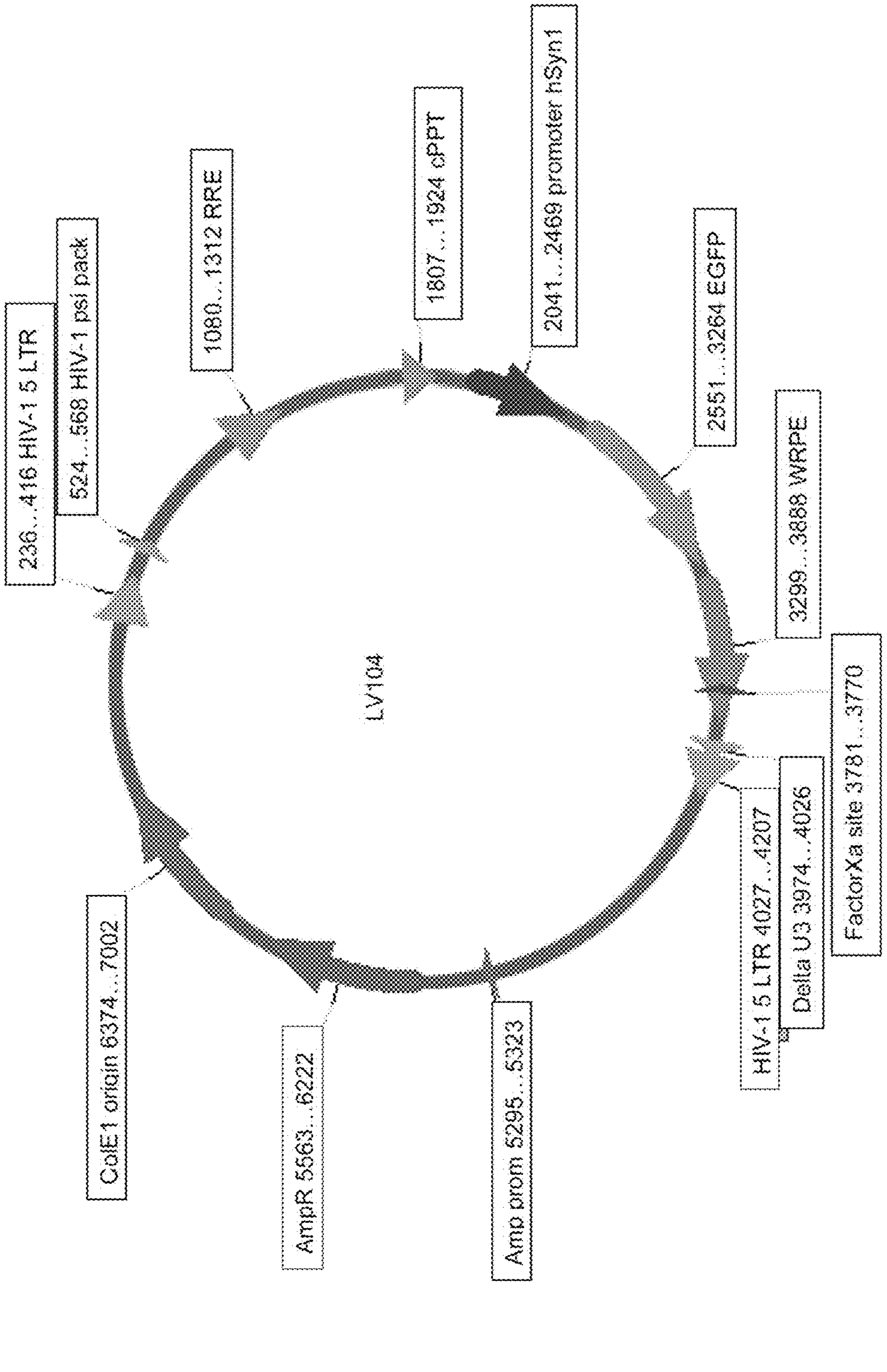
FIGS. 1A-1D illustrate knockdown of GluK2 protein in rat hippocampal neurons with lentivirally-encoded antisense sequences against human Grik2 mRNA.
Figure 1B:
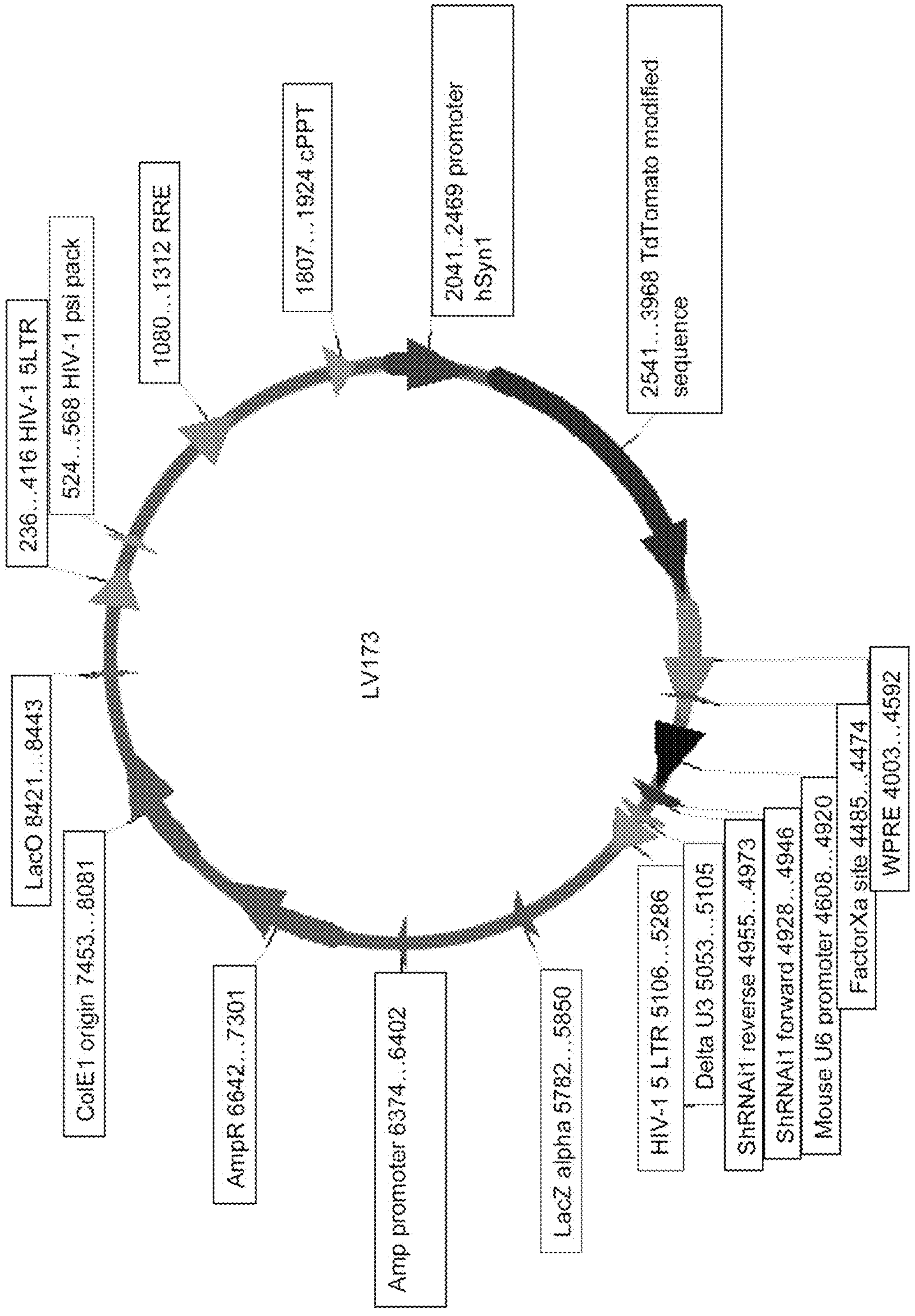
Figure 1C:
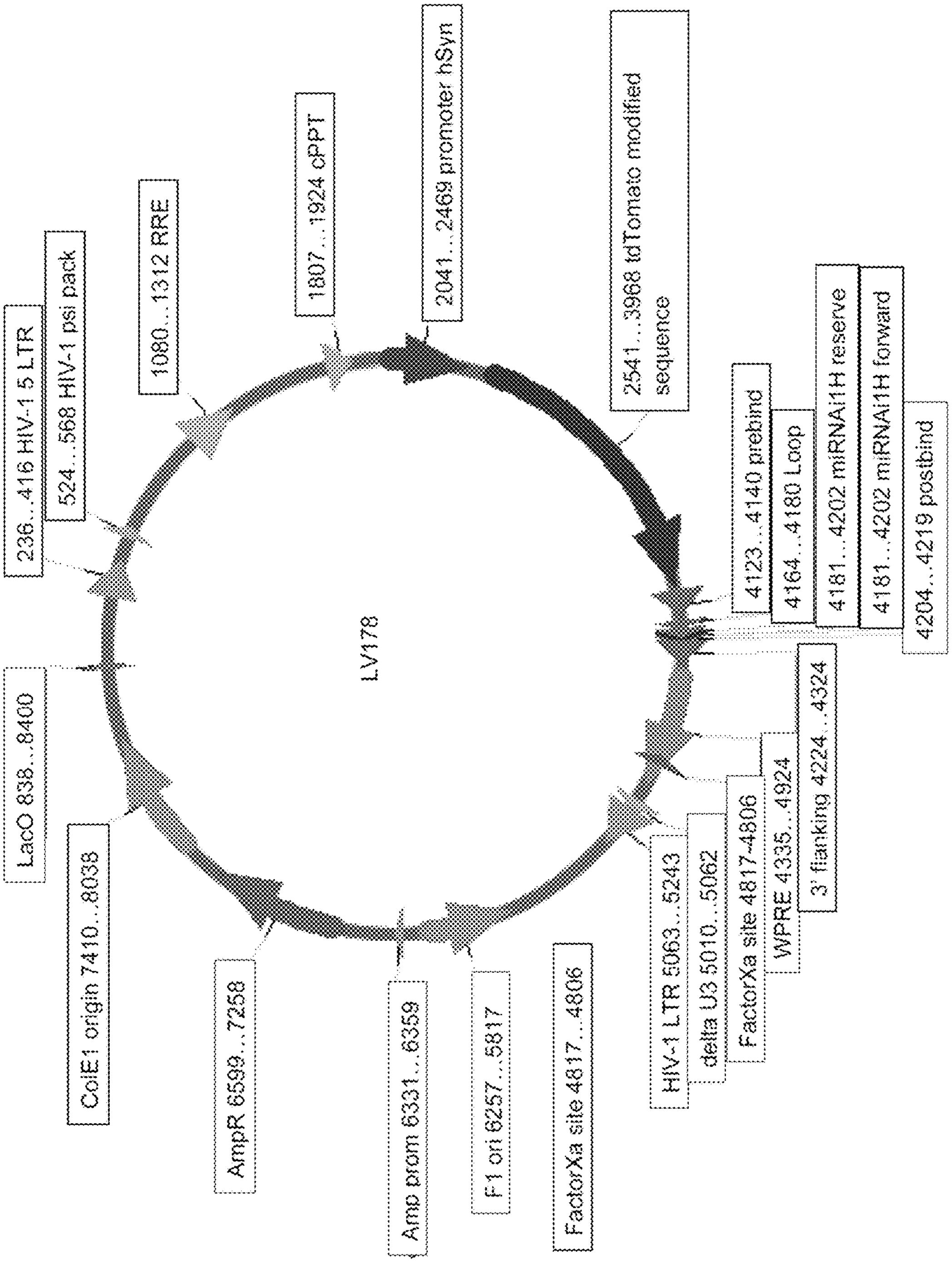
Figure 1D:
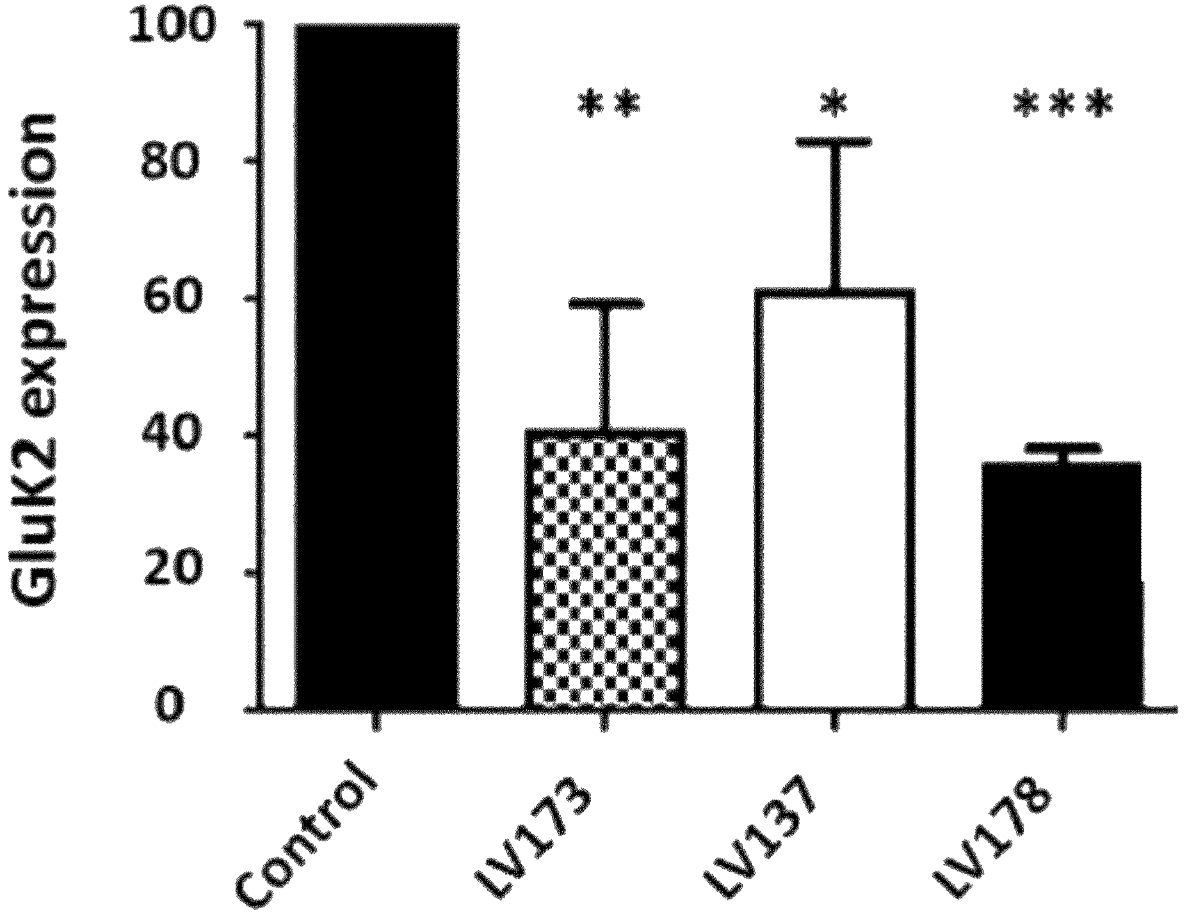

All the procedures were conducted in accordance with the guidelines of the University of Bordeaux/CNRS Animal Care or approved by the Institut National de la Santé et de la Recherche Médicale (INSERM) animal care and use agreement (B-13-055-19) and the European community council directive (2010/63/UE).

Primary Hippocampal Cultures

Primary hippocampal cultures were prepared from 18-day embryonic Sprague-Dawley rats. Briefly, hippocampi were dissected and collected in HBSS containing Penicillin-Streptomycin (PS) and HEPES. Tissues were dissociated with Trypsin-EDTA/PS/HEPES and neurons were plated in minimum essential medium supplemented with 10% horse serum on coverslips coated with 1 mg/mL poly-Llysine (PLL) in 6-well plates at a density of 550.000 cells, for transfection, per dish. Following neuronal attachment to the surface, Ara was added to prevent the growth of glial cells. Cells were maintained at 36.5 °C with 5% CO2.

In Vitro Models of Temporal Lobe Epilepsy

Swiss mice were used. They had access to food and water ad libitum and were housed under a 12 h light/dark cycle at 22-24 °C. Hippocampal organotypic slices (350 μm) were prepared from mice (P8-9) using a Mollwain tissue chopper. Slices were placed on mesh inserts (Millipore) inside culture dishes containing 1 ml of the following medium: MEM 50%, HS 25%, HBSS 25%, HEPES 15 mM, glucose 6.5 mg/ml and insulin 0.1 mg/ml. Culture medium was changed every 2-3 days and slices maintained in an incubator at 37 °C/5% CO2. Pilocarpine (0.5 UM) was added to the medium at 5 D.I.V and removed at 7 D.I.V; slices were recorded for experiments from 13 D.I.V. to 15 D.I.V. When slices were treated with lentivirus or adeno-associated virus (AAV), the infection were performed at 0 D.I.V.

Electrophysiological Recordings and Analysis

Organotypic slices were individually transferred to a recording chamber maintained at 30-32 °C and continuously perfused (2 ml/min) with oxygenated ACSF containing the following (in mM): 126 NaCl, 3.5 KCl, 1.2 NaH2PO4, 26

$NaHCO_3$, 1.3 MgCl2, 2.0 CaCI2, and 10 D-glucose, pH 7.4. Experiments were performed in the presence of 5 μM SR-95531 (gabazine, Sigma). Local field potentials were recorded in the granule cell layer of the dentate gyrus with an insulated tungsten electrode (diameter 50 μm) using a DAM-80 amplifier (low filter, 1 Hz; highpass filter, 3 KHz; World Precision Instruments, Sarasota, FL). Signals were analyzed off-line using Clampfit 10.7 (PClamp) and Mini-Analysis 6.0.1 (Synaptosoft, Decatur, GA).

RNAi And Viral Vectors

Figure 3A:
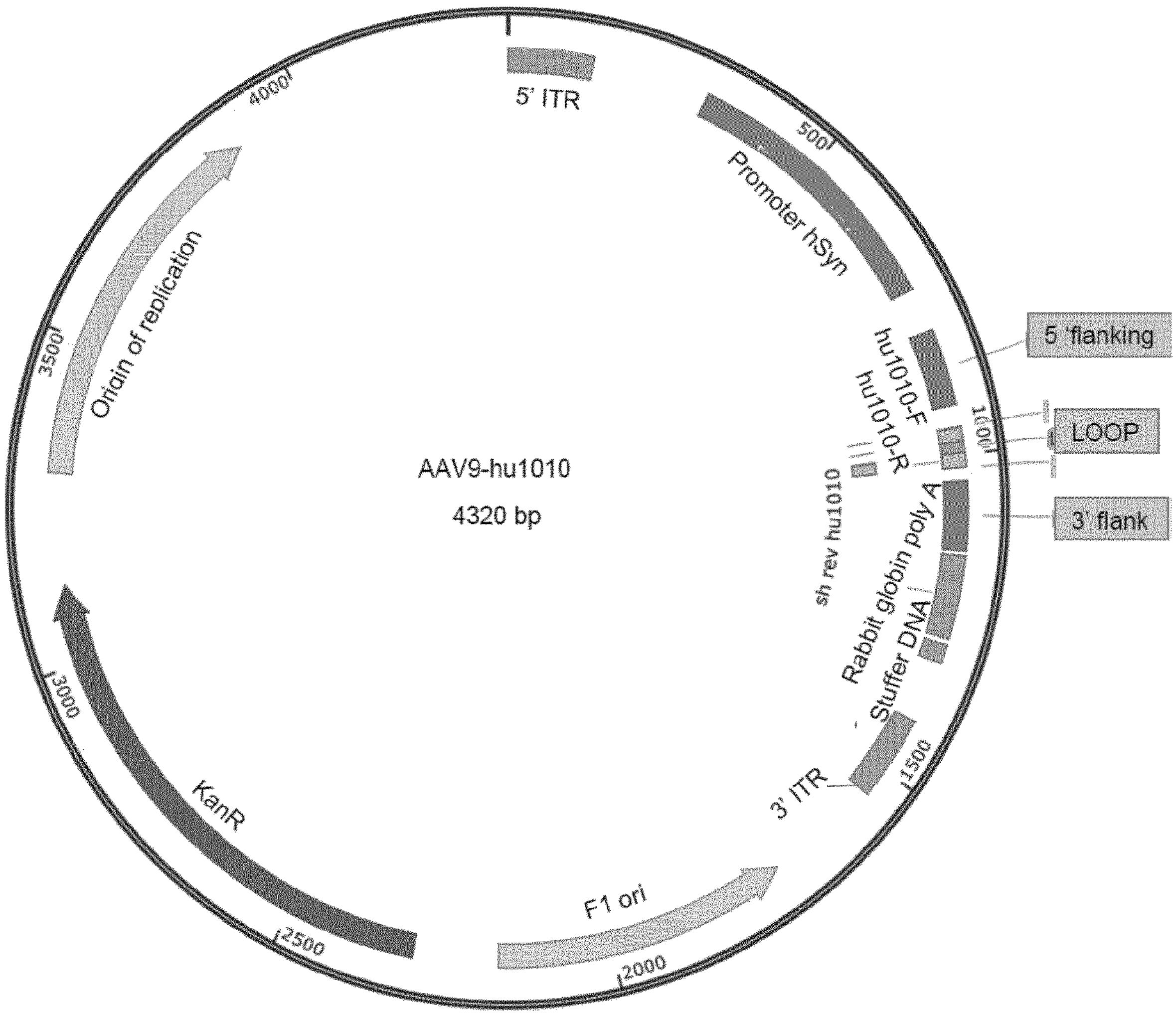
FIGS. 3A-3B illustrate the effect of AAV vectors on epileptiform discharges in rodent disinhibited cortical slices.

We designed RNAi sequences using Smart selection design (Birmingham et al., A protocol for designing siRNAs with high functionality and specificity, Nature Methods., August 2007; 9:2068-2078.) We compared the efficiency of RNAi sequences (RNAi #h, RNAi #r, RNAi #m) either as shRNAs, or folded as a short hairpin micro RNA adapted (shmiRNA), and finally as a microRNA using the miR30 structure. To express RNAi sequences (RNAi #h, RNAi #r, RNAi #m), we used viral vectors, in order to promote more efficient transfection than with plasmids for DNA expression. In a first series of experiments, RNAi were delivered by lentiviral vectors (Table 3). We selected RNAi #h sequence as an efficient sequence to downregulate the levels of GluK2 in infected primary cultures of rat neurons by Western blotting. We next changed to AAVs which are commonly used viral vectors for gene therapy (Table 3). These AAV were produced by REGENXBIO, Inc. (Rockville, MD; see exemplary AAV vector map of FIG. 3A).

The selected human RNAi (RNAi #h) sequence was compared with rat and mouse sequences (Table 1):

TABLE 1

Oligonucleotides encoding RNAi sequences targeting human, mouse, and rat Grik2 mRNA

| Name | Species | SEQ ID NO | cDNA encoding a passenger strand sequence | SEQ ID NO | cDNA encoding a guide strand sequence |
|---|---|---|---|---|---|
| RNAi#h | *H. sapiens* | 2 | taaaacaggcattagctatggg | 14 | cccatagctaatgcctgtttta |
| RNAi#r | *R. norvegicus* | 2 | taaaacaggcattagctatggg | 14 | cccatagctaatgcctgtttta |
| RNAi#m | *M. musculus* | 3 | taaagcaggcattagctatggg | 15 | cccatagctaatgcctgcttta |

Table 2 below describes RNA sequences encoded by vectors of the disclosure.

TABLE 2

RNA sequences encoded by vectors of the disclosure

| Name | Species | SEQ ID NO | RNA sequence corresponding to passenger strand | SEQ ID NO | RNA sequence corresponding to guide strand |
|---|---|---|---|---|---|
| RNAi#h | *H. sapiens* | 16 | uaaaacaggcauuagcuauggg | 18 | cccauagcuaaugccuguuuua |
| RNAi#r | *R. norvegicus* | 16 | uaaaacaggcauuagcuauggg | 18 | cccauagcuaaugccuguuuua |
| RNAi#m | *M. musculus* | 17 | uaaagcaggcauuagcuauggg | 19 | cccauagcuaaugccugcuuua |

Lentivirus or AAV9 coding for miRNAih were used; miRNAih was expressed under CAG or human synapsin (hSyn) promoters. The promoter sequence for the hSyn promoter used in conjunction with lentiviral vectors is provided in SEQ ID NO: 27, as is shown below.

```
(SEQ ID NO: 27)
CTGCAGAGGGCCCTGCGTATGAGTGCAAGTGGGTTTTAGGACCAGGATG
AGGGGGGTGGGGGTGCCTACCTGACGACCGACCCCGACCCACTGGACAA
GCACCCAACCCCCATTCCCCAAATTGCGCATCCCCTATCAGAGAGGGGG
AGGGGAAACAGGATGCGGCGAGGCGCGTGCGCACTGCCAGCTTCAGCAC
CGCGGACAGTGCCTTCGCCCCCGCCTGGCGGCGCGCGCCACCGCCGCCT
CAGCACTGAAGGCGCGCTGACGTCACTCGCCGGTCCCCCGCAAACTCCC
CTTCCCGGCCACCTTGGTCGCGTCCGCGCCGCCGCCGGCCCAGCCGGAC
CGCACCACGCGAGGCGCGAGATAGGGGGGCACGGGCGCGACCATCTGCG
CTGCGGCGCCGGCGACTCAGCGCTGCCTCAGTCTGC
```

The promoter sequence for the hSyn promoter used in conjunction with the AAV9 vectors is provided in SEQ ID NO: 28, as is shown below.

```
(SEQ ID NO: 28)
CTGCAGAGGGCCCTGCGTATGAGTGCAAGTGGGTTTTAGGACCAGGATG
AGGCGGGGTGGGGGTGCCTACCTGACGACCGACCCCGACCCACTGGACA
AGCACCCAACCCCCATTCCCCAAATTGCGCATCCCCTATCAGAGAGGGG
GAGGGGAAACAGGATGCGGCGAGGCGCGTGCGCACTGCCAGCTTCAGCA
CCGCGGACAGTGCCTTCGCCCCCGCCTGGCGGCGCGCGCCACCGCCGCC
TCAGCACTGAAGGCGCGCTGACGTCACTCGCCGGTCCCCCGCAAACTCC
CCTTCCCGGCCACCTTGGTCGCGTCCGCGCCGCCGCCGGCCCAGCCGGA
CCGCACCACGCGAGGCGCGAGATAGGGGGGCACGGGCGCGACCATCTGC
GCTGCGGCGCCGGCGACTCAGCGCTGCCTCAGTCTGCCAATTGCAGCGG
AGGAGTCGTGTCGTGCCTGAGAGCGCAG
```

Some constructs were hybrid constructs also expressing fluorescent reporter genes.

TABLE 3

List of viral constructs used to knockdown the expression of Grik2 by RNAi

| Construct | Sequence | Construct | Viral titer/mL |
|---|---|---|---|
| LV180 | Scramble | LV.hSyn.TdTomato.U6.shRNAscramble | 4.6E+08 Infectious particles |
| LV173 | Human | LV.hSyn.TdTomato.U6.shRNAi#h | 7.9E+08 Infectious particles |
| LV137 | Human | LV.CAG.tGFP.IRES.shmiRNAi#h | 2.7E+08 Infectious particles |
| LV104 | — | LV.hSyn.GFP | 8E+08 Infectious particles |
| LV178 | Human | LV.hSyn.TdTomato.miRNAi#h | 3.0E+09 Infectious particles |

TABLE 3-continued

List of viral constructs used to knockdown the expression of Grik2 by RNAi

| Construct | Sequence | Construct | Viral titer/mL |
|---|---|---|---|
| AAV9-control | — | AAV9.CAG.GFP | 2.0E+13 Gene copies |
| AAV9-scramble | Scramble | AAV9.hSyn.GFP.Scr2 | 9E+12 Gene copies |
| AAV9-hu1010 | Human | AAV9.hSyn.miR30.miRNAi#h (SEQ ID NO: 25) | 9E+12 Gene copies |

Statistics Analyses

All values are given as means+SEM. Statistical analyses were performed using Graphpad Prism Graphpad Prism 7 (GraphPad Software, La Jolla, CA). For between-group comparisons, raw data were analyzed by a Mann-Whitney test. The level of significance was set at $P<0.05$.

Results

Firstly, cell culture experiments were performed in primary embryonic rat neurons to evaluate the effect of RNA interference strategy on the levels of the endogenous GluK2 protein level. By Western blotting, we observed a significant reduction of the GluK2 level with the RNAi #1 h (SEQ ID NO: 14) (FIG. 1 and corresponding Table 4). The results showed also the importance of the RNAi processing: the stabilization of RNAi #1 h by mir30 structure (LV178) increased the efficacy in comparison to the shRNAi (LV173) despite the fact that these two constructs significantly reduce GluK2 level expression in rat neurons, respectively by 64.2±1.5% ($p<0.0001$) and by 59.5±10.9% ($p<0.005$) compared to the control without infection.

TABLE 4

GluK2 levels in cultured cortical neurons infected with LV constructs encoding RNAi sequences

| GluK2 levels | LV173 | LV137 | LV178 |
|---|---|---|---|
| Mean | 40.6 | 61.2 | 35.8 |
| S.E.M. | 10.9 | 12.8 | 1.5 |
| P-value* | 0.005 | 0.038 | <0.0001 |

*Statistically significant differences in GluK2 levels were measured between GluK2 levels in cells treated with RNAi sequences and a control condition in which cortical neurons were not infected.

Figure 2:
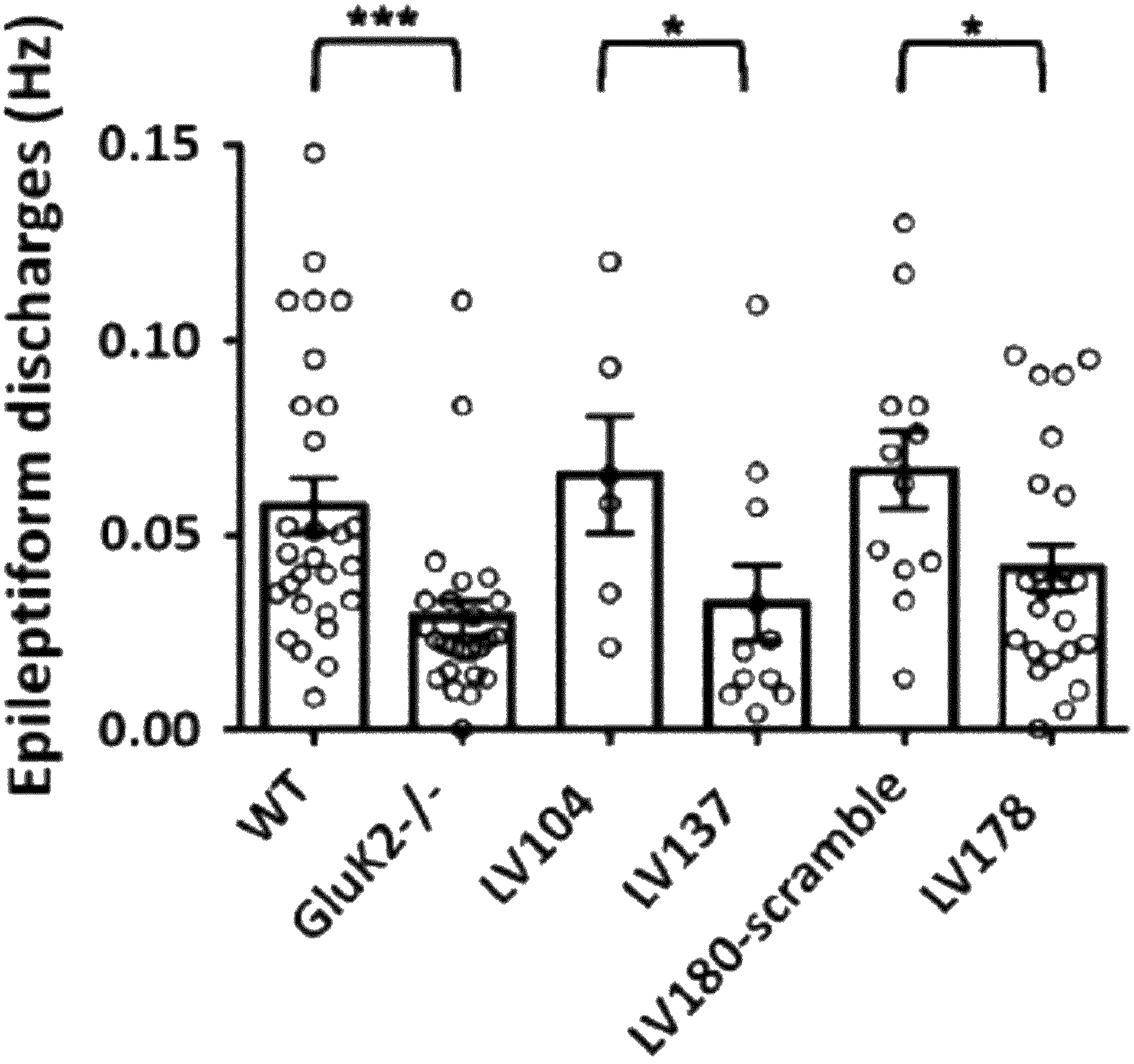
FIG. 2: Bar graphs illustrating the effect of LV137 and LV178 compared with control conditions (LV104, LV180-scramble, respectively) on the frequency of epileptiform discharges in mouse organotypic hippocampal slices. Note the similar effects observed in slices treated with LV137, LV178 compared with GluK2−/−slices. *,  and * denote significance of $P<0.05$, $P<0.01$ and $P<0.001$.
Figure 3B:
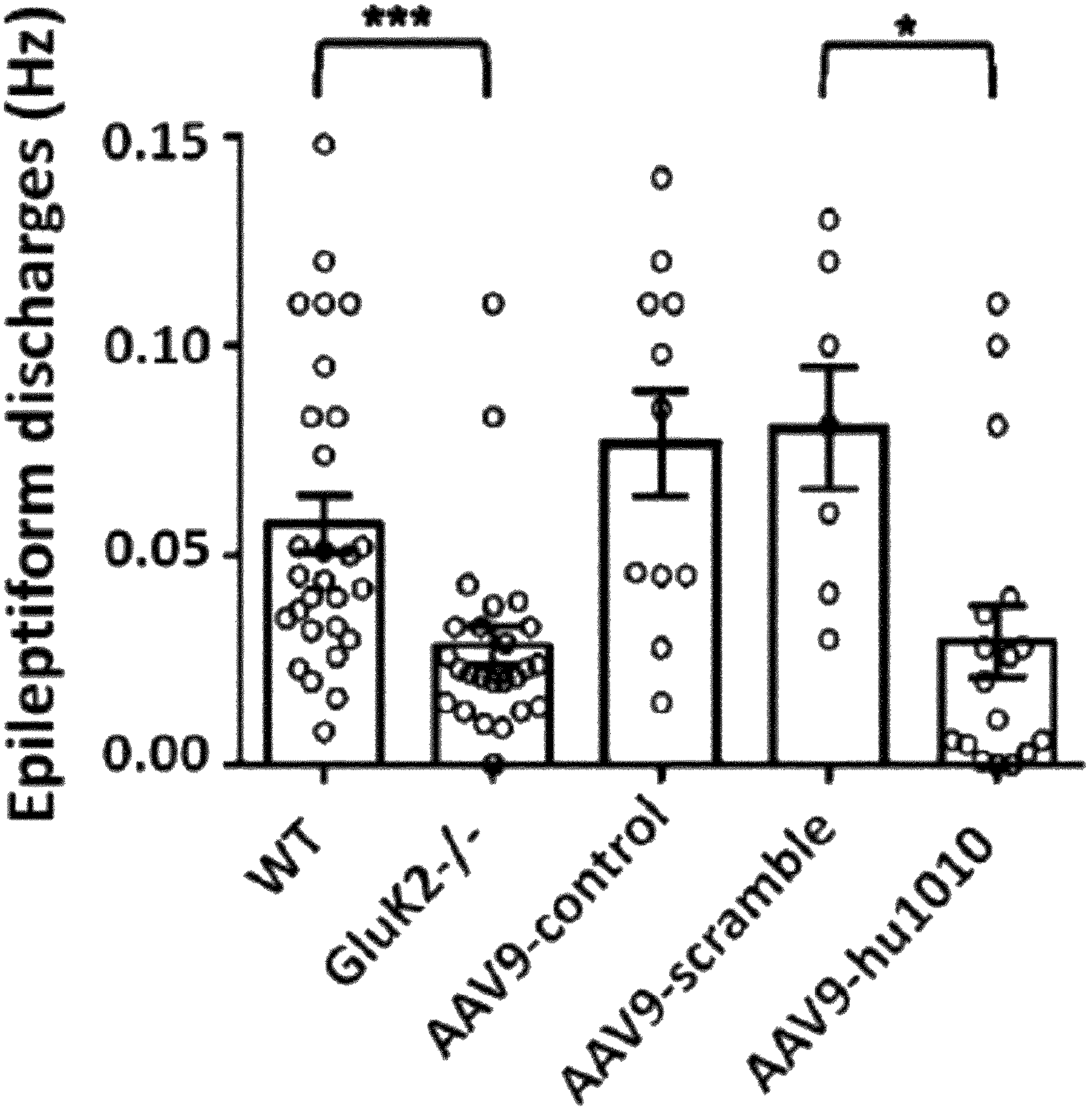

Secondly, reliable stereotyped spontaneous epileptiform discharges were recorded in organotypic slices in the presence of 5 μM gabazine as previously described (Peret et al., 2014). In this condition, we observed a striking reduction of the frequency of epileptiform discharges in treated slices with LV137 (LV.CAG.tGFP.IRES.shmiRNAi #h), LV178 (LV.hSyn.TdTomato.miRNAi #h) and AAV9-hu1010 (AAV9.hSyn.miR30.miRNAi #h), compared with control conditions (LV.hSyn.GFP, LV.hSyn.TdTomato.U6.shRNAscramble (TTTGTGAGGGTCTGGTC; SEQ ID NO: 36) and AAV9.CAG.GFP, respective; Tables 5 and 6 and FIGS. 2 and 3). Remarkably, the reduction of the frequency of epileptiform discharges observed in the presence of viral vectors was similar to the one observed in hippocampal organotypic slices from mice lacking the GluK2 (GluK2−/−) subunit (Peret et al., 2014) (Table 5 and 6 and FIGS. 2 and 3).

TABLE 5

Effect of LV137 and LV178 on the frequency of epileptiform discharges

| | WT[(a)] | GluK2−/−[(a)] | LV104 | LV137 | LV180 | LV178 |
|---|---|---|---|---|---|---|
| Mean | 0.057 | 0.029 | 0.065 | 0.032 | 0.067 | 0.043 |
| S.E.M. | 0.0068 | 0.0046 | 0.0149 | 0.0098 | 0.0099 | 0.0060 |
| n | 28 | 25 | 6 | 11 | 12 | 23 |
| P-value* | ***0.0001 | | *0.0449 | | *0.0348 | |

*Statistically significant differences in epileptiform discharges were measured between LV137 or LV178 and control treatments (LV104 and LV180-scramble, respectively).
[(a)]From Peret et al. Cell Rep. 8(2):347-54, 2014.

TABLE 6

Effect of AAV9-hu1010 compared with control conditions (AAV9-scramble) on the frequency of epileptiform discharges.

| | WT[(a)] | GluK2−/−[(a)] | AAV9-control | AAV9-scramble | AAV9-hu1010 |
|---|---|---|---|---|---|
| Mean | 0.057 | 0.029 | 0.077 | 0.080 | 0.029 |
| S.E.M. | 0.0068 | 0.0046 | 0.0127 | 0.0146 | 0.0085 |
| n | 28 | 25 | 11 | 7 | 17 |
| P-value* | ***0.0001 | | | **0.0031 | |

*Statistically significant differences in epileptiform discharges were measured between AAV9-hu1010 and control vector (AAV9-scramble; UAAUGUUAGUCAUGUCCACCG; SEQ ID NO: 37) treatment groups.
[(a)]From Peret et al. Cell Rep. 8(2):347-54, 2014.

CONCLUSION

In conclusion, our data demonstrated that GluK2 gene (Grik2) silencing, using lentivirus or AAV vectors carrying a RNAi sequence targeting Grik2 (e.g., miRNAi1 h), is an efficient strategy to prevent spontaneous epileptiform discharges in TLE.

REFERENCES

Throughout this application, various references describe the state of the art to which this disclosure pertains. The disclosures of these references are hereby incorporated by reference into the present disclosure.

Bahn S., Volk B., Wisden W. (1994). Kainate receptor gene expression in the developing rat brain. J. Neurosci. 14 5525-5547. 10.1523/JNEUROSCI.14-09-05525.1994.

Boudreau Ryan L., Rodríguez-Lebrón Edgardo, Davidson Beverly L., RNAi medicine for the brain: progresses and challenges, Human Molecular Genetics, Volume 20, Issue R1, 15 Apr. 2011, Pages R21-R27.

Bouvier G., Larsen R. S., Rodríguez-Moreno A., Paulsen O., Sjostrom P. J. (2018). Towards resolving the presynaptic NMDA receptor debate. Curr. Opin. Neurobiol. 51 1-7. 10.1016/j.conb.2017.12.020.

Crépel V, Mulle C (2015) Physiopathology of kainate receptors in epilepsy. Curr Opin Pharmacol 20:83-88; doi: 10.1016/j.coph.2014.11.012. Epub 2014 Dec. 13.

Englot, D J., et al (2013) Seizure outcomes after resective surgery for extra-temporal lobe epilepsy in pediatric patients: A systematic review. J. Neurosurgery. 12 (2): 97-201

Fritsch B., Reis J., Gasior M., Kaminski R. M., Michael A., Rogawski M. A. (2014). Role of GluK1 kainate receptors in seizures, epileptic discharges, and epileptogenesis. J. Neurosci. 34 5765-5775. 10.1523/JNEUROSCI.5307-13.2014.

Gabriel S, Njunting M, Pomper J K, Merschhemke M, Sanabria E R G, Eilers A, Kivi A, Zeller M, Meencke H-J, Cavalheiro E a, Heinemann U, Lehmann T-N(2004) Stimulus and potassium-induced epileptiform activity in the human dentate gyrus from patients with and without hippocampal sclerosis. J Neurosci 24:10416-10430.

Hardy J. (2010). Genetic analysis of pathways to Parkinson disease. Neuron, 68 (2), 201-206. doi: 10.1016/j.neuron.2010.10.014.

Melyan Z., Lancaster B., Wheal H. V. (2004). Metabotropic regulation of intrinsic excitability by synaptic activation of kainate receptors. J. Neurosci. 24 4530-4534. 10.1523/JNEUROSCI.5356-03.2004

Melyan Z., Wheal H. V., Lancaster B. (2002). Metabotropic-mediated kainate receptor regulation of isAHP and excitability in pyramidal cells. Neuron 34 107-114. 10.1016/S0896-6273 (02) 00624-4.

Mulle C., Sailer A., Pérez-Otaño I., Dickinson-Anson H., Castillo P. E., Bureau I., et al. (1998). Altered synaptic physiology and reduced susceptibility to kainate-induced seizures in GluR6-deficient mice. Nature 392 601-605.

Peret A, Christie L a., Ouedraogo D W, Gorlewicz A, Epsztein J, Mulle C, Crépel V (2014) Contribution of Aberrant GluK2-Containing Kainate Receptors to Chronic Seizures in Temporal Lobe Epilepsy. Cell Rep 8:347-354.

Reiner A, Arant R J, and Isacoff E Y (2012) Assembly Stoichiometry of the GluK2/GluK5 Kainate Receptor Complex. Cell Rep 1:234-240.

Represa A, Le Gall La Salle G, Ben-Ari Y (1989a) Hippocampal plasticity in the kindling model of epilepsy in rats. Neurosci Lett 99:345-350.

Represa A, Robain O, Tremblay E, Ben-Ari Y (1989b) Hippocampal plasticity in childhood epilepsy. Neurosci Lett 99:351-355.

Rodríguez-Moreno A., Herreras O., Lerma J. (1997). Kainate receptors presynaptically downregulate GABAergic inhibition in the rat hippocampus. Neuron 19 893-901. 10.1016/S0896-6273 (00) 80970-8.

Rodríguez-Moreno A., Sihra T. S. (2007a). Kainate receptors with a metabotropic modus operandi. Trends Neurosci. 30 630-637.

Rodríguez-Moreno A., Sihra T. S. (2007b). Metabotropic actions of kainate receptors in the CNS. J. Neurochem. 103 2121-2135.

Sapru Mohan K., Yates Jonathan W., Hogan Shea, Jiang Lixin, Halter Jeremy, Bohn Martha C. (2006). Silencing of human α-synuclein in vitro and in rat brain using lentiviral-mediated RNAi. Neurology. 198:382-390.

Smolders I., Bortolotto Z. A., Clarke V. R., Warre R., Khan G. M., O'Neill M. J., et al. (2002). Antagonists of GLU (K5)-containing kainate receptors prevent pilocarpine-induced limbic seizures. Nat. Neurosci. 5 796-804. 10.1038/nn88.

Sutula T, Cascino G, Cavazos J, Parada I, Ramirez L (1989) Mossy fiber synaptic reorganization in the epileptic human temporal lobe. Ann Neurol 26:321-330.

Tauck D L, Nadler J V (1985) Evidence of functional mossy fiber sprouting in hippocampal formation of kainic acid-treated rats. J Neurosci 5:1016-1022

Valbuena S., Lerma J. (2016). Non-canonical signaling, the hidden life of ligand-gated ion channels. Neuron 92 316-329. 10.1016/j.neuron.2016.10.016.

Zinn, E., Pacouret, S., Khaychuk, V., Turunen, H. T., Carvalho, L. S., Andres-Mateos, E., . . . . Vandenberghe, L. H. (2015). In Silico Reconstruction of the Viral Evolutionary Lineage Yields a Potent Gene Therapy Vector. Cell reports, 12 (6), 1056-1068. doi: 10.1016/j.celrep.2015.07.019.

The invention claimed is:

1. A method for treating or ameliorating temporal lobe epilepsy in a subject in need thereof comprising administering to the subject a recombinant antisense oligonucleotide comprising a guide sequence that targets a Grik2 mRNA, wherein the guide sequence comprises a polynucleotide with at least 85% sequence identity to the nucleic acid sequence of SEQ ID NO: 14, 15, 18, or 19, an expression cassette comprising the antisense oligonucleotide, or a vector comprising the expression cassette.

2. The method of claim 1, wherein the subject is a human.

3. The method of claim 1, wherein the expression cassette or the vector comprises a nucleic acid sequence with at least 85%, 90%, 91%, 92%, 93%, 94%, 95%, 96%, 97%, 98%, 99% identity to, or the sequence of, SEQ ID NO: 21 or 23.

4. The method of claim 1, wherein the polynucleotide has at least 90% or 95% sequence identity to, or the sequence of, the nucleic acid sequence of SEQ ID NO: 14, 15, 18, or 19.

5. The method of claim 1, wherein the polynucleotide further comprises a passenger sequence, wherein the passenger sequence has at least 85%, 90%, or 95% sequence identity to, or the sequence of, the nucleic acid sequence of SEQ ID NO: 2, 3, 16, or 17.

6. The method of claim 1, wherein the guide sequence is fully or partially complementary to the nucleic acid sequence of SEQ ID NO: 2, 3, 16, or 17.

7. The method of claim 1, wherein the vector comprises:

(a) a guide sequence comprising a polynucleotide with at least 85% sequence identity to the nucleic acid sequence of SEQ ID NO: 14, 15, 18, or 19; and (b) a passenger sequence comprising a polynucleotide with at least 85% sequence identity to the nucleic acid sequence of SEQ ID NO: 2, 3, 16, or 17.

8. The method of claim 7, wherein:

(a) the guide sequence has at least 90% or 95% sequence identity to, or the sequence of, SEQ ID NO: 14, 15, 18, or 19; and/or (b) the passenger sequence has at least 90% or 95% sequence identity to, or the sequence of, SEQ ID NO: 2, 3, 16 or 17.

9. The method of claim 7, wherein the vector is a mammalian, bacterial, or viral vector.

10. The method of claim 9, wherein the viral vector is an adeno-associated viral (AAV) vector, lentiviral vector, or retroviral vector.

11. The method of claim 10, wherein the AAV vector is an AAV9 or AAVrh 10 vector.

12. The method of claim 10, wherein the AAV vector comprises (i) an expression cassette comprising the guide sequence and the passenger sequence operably linked to one or more regulatory elements and flanked by ITRs, and (ii) an AAV capsid.

13. The method of claim 12, wherein the one or more regulatory elements comprise a promoter sequence, enhancer sequence, transcription termination sequence, and/or polyadenylation signal.

14. The method of claim 1, wherein the expression cassette comprises a polynucleotide comprising: I)

(a) a stem-loop sequence comprising, from 5' to 3':

(i) a 5' stem-loop arm comprising a guide sequence having a nucleic acid sequence of SEQ ID NO: 14, 15, 18, or 19 or a variant thereof having at least 85% sequence identity to the nucleic acid sequence of SEQ ID NO: 14, 15, 18, or 19;

(ii) a loop region, wherein the loop region comprises a miR-30 loop sequence; and (iii) a 3' stem-loop arm comprising a passenger sequence having a nucleic acid sequence of SEQ ID NO: 2, 3, 16, or 17;

(b) a first flanking region located 5' to the guide sequence; and (c) a second flanking region located 3' to the passenger sequence; or II)

(a) a stem-loop sequence comprising, from 5' to 3':

(i) a 5' stem-loop arm comprising a passenger sequence having a nucleic acid sequence of SEQ ID NO: 2, 3, 16, or 17 or a variant thereof having at least 85% sequence identity to the nucleic acid sequence of SEQ ID NO: 2, 3, 16, or 17;

(ii) a loop region, wherein the loop region comprises a miR-30 loop sequence; and (iii) a 3' stem-loop arm comprising guide sequence having a nucleic acid sequence of SEQ ID NO: 14, 15, 18, or 19 or a variant thereof having at least 85% sequence identity to the nucleic acid sequence of SEQ ID NO: 14, 15, 18, or 19;

(b) a first flanking region located 5' to the passenger sequence; and (c) a second flanking region located 3' to the guide sequence.

15. The method of claim 14, wherein the nucleic acid sequence of the stem-loop arm comprising the guide sequence of I) and/or II) has at least 90%, 91%, 92%, 93%, 94%, 95%, 96%, 97%, 98%, 99%, or more sequence identity to the nucleic acid sequence of SEQ ID NO: 14, 15, 18, or 19.

16. The method of claim 14, wherein:

(a) the stem-loop sequence of I) comprises a polynucleotide having at least 85% sequence identity to the nucleic acid sequence of SEQ ID NO: 20;

(b) the expression cassette comprises a polynucleotide having at least 85% sequence identity to the nucleic acid sequence of SEQ ID NO: 21;

(c) the stem-loop sequence of II) comprises a polynucleotide having at least 85% sequence identity to the nucleic acid sequence of SEQ ID NO: 22; or (d) the expression cassette comprises a polynucleotide having at least 85% sequence identity to the nucleic acid sequence of SEQ ID NO: 23.

17. The method of claim 14, wherein:

(a) the first flanking region and the second flanking regions are miR-30 flanking regions; or (b) the first flanking region comprises a polynucleotide having at least 85% sequence identity to the nucleic acid sequence of SEQ ID NO: 24; or (c) the second flanking region comprises a polynucleotide having at least 85% sequence identity to the nucleic acid sequence of SEQ ID NO: 26; or (d) the passenger sequence is fully or partially complementary to the guide sequence; or (e) the expression cassette further comprises a promoter selected from the group consisting of a Pol II promoter, a Pol III promoter, a neuron-specific promoter, an hSyn promoter, a CaMKII promoter, a U6 promoter, or a CAG promoter.

18. The method of claim 1, wherein the recombinant antisense oligonucleotide, the expression cassette, or the vector is administered to the subject in a pharmaceutical composition comprising a pharmaceutically acceptable carrier, excipient, or diluent.

* * * * *

SEQUENCE LISTING

```
<160> NUMBER OF SEQ ID NOS: 37

<210> SEQ ID NO 1
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: R is A or G

<400> SEQUENCE: 1

aaarcaggca ttagctatg                                                19


<210> SEQ ID NO 2
<211> LENGTH: 19
<212> TYPE: DNA
<213> ORGANISM: Homo sapiens

<400> SEQUENCE: 2

aaaacaggca ttagctatg                                                19


<210> SEQ ID NO 3
<211> LENGTH: 19
<212> TYPE: DNA
<213> ORGANISM: Mus musculus

<400> SEQUENCE: 3

aaagcaggca ttagctatg                                                19


<210> SEQ ID NO 4
<211> LENGTH: 908
<212> TYPE: PRT
<213> ORGANISM: Homo sapiens

<400> SEQUENCE: 4

Met Lys Ile Ile Phe Pro Ile Leu Ser Asn Pro Val Phe Arg Arg Thr
1               5                   10                  15

Val Lys Leu Leu Leu Cys Leu Leu Trp Ile Gly Tyr Ser Gln Gly Thr
            20                  25                  30

Thr His Val Leu Arg Phe Gly Gly Ile Phe Glu Tyr Val Glu Ser Gly
        35                  40                  45

Pro Met Gly Ala Glu Glu Leu Ala Phe Arg Phe Ala Val Asn Thr Ile
    50                  55                  60

Asn Arg Asn Arg Thr Leu Leu Pro Asn Thr Thr Leu Thr Tyr Asp Thr
65                  70                  75                  80

Gln Lys Ile Asn Leu Tyr Asp Ser Phe Glu Ala Ser Lys Lys Ala Cys
                85                  90                  95

Asp Gln Leu Ser Leu Gly Val Ala Ala Ile Phe Gly Pro Ser His Ser
            100                 105                 110
```

-continued

```
Ser Ser Ala Asn Ala Val Gln Ser Ile Cys Asn Ala Leu Gly Val Pro
        115                 120                 125

His Ile Gln Thr Arg Trp Lys His Gln Val Ser Asp Asn Lys Asp Ser
    130                 135                 140

Phe Tyr Val Ser Leu Tyr Pro Asp Phe Ser Ser Leu Ser Arg Ala Ile
145                 150                 155                 160

Leu Asp Leu Val Gln Phe Phe Lys Trp Lys Thr Val Thr Val Val Tyr
                165                 170                 175

Asp Asp Ser Thr Gly Leu Ile Arg Leu Gln Glu Leu Ile Lys Ala Pro
            180                 185                 190

Ser Arg Tyr Asn Leu Arg Leu Lys Ile Arg Gln Leu Pro Ala Asp Thr
        195                 200                 205

Lys Asp Ala Lys Pro Leu Leu Lys Glu Met Lys Arg Gly Lys Glu Phe
    210                 215                 220

His Val Ile Phe Asp Cys Ser His Glu Met Ala Ala Gly Ile Leu Lys
225                 230                 235                 240

Gln Ala Leu Ala Met Gly Met Met Thr Glu Tyr Tyr His Tyr Ile Phe
                245                 250                 255

Thr Thr Leu Asp Leu Phe Ala Leu Asp Val Glu Pro Tyr Arg Tyr Ser
            260                 265                 270

Gly Val Asn Met Thr Gly Phe Arg Ile Leu Asn Thr Glu Asn Thr Gln
        275                 280                 285

Val Ser Ser Ile Ile Glu Lys Trp Ser Met Glu Arg Leu Gln Ala Pro
    290                 295                 300

Pro Lys Pro Asp Ser Gly Leu Leu Asp Gly Phe Met Thr Thr Asp Ala
305                 310                 315                 320

Ala Leu Met Tyr Asp Ala Val His Val Val Ser Val Ala Val Gln Gln
                325                 330                 335

Phe Pro Gln Met Thr Val Ser Ser Leu Gln Cys Asn Arg His Lys Pro
            340                 345                 350

Trp Arg Phe Gly Thr Arg Phe Met Ser Leu Ile Lys Glu Ala His Trp
        355                 360                 365

Glu Gly Leu Thr Gly Arg Ile Thr Phe Asn Lys Thr Asn Gly Leu Arg
    370                 375                 380

Thr Asp Phe Asp Leu Asp Val Ile Ser Leu Lys Glu Glu Gly Leu Glu
385                 390                 395                 400

Lys Ile Gly Thr Trp Asp Pro Ala Ser Gly Leu Asn Met Thr Glu Ser
                405                 410                 415

Gln Lys Gly Lys Pro Ala Asn Ile Thr Asp Ser Leu Ser Asn Arg Ser
            420                 425                 430

Leu Ile Val Thr Thr Ile Leu Glu Glu Pro Tyr Val Leu Phe Lys Lys
        435                 440                 445

Ser Asp Lys Pro Leu Tyr Gly Asn Asp Arg Phe Glu Gly Tyr Cys Ile
    450                 455                 460

Asp Leu Leu Arg Glu Leu Ser Thr Ile Leu Gly Phe Thr Tyr Glu Ile
465                 470                 475                 480

Arg Leu Val Glu Asp Gly Lys Tyr Gly Ala Gln Asp Asp Ala Asn Gly
                485                 490                 495

Gln Trp Asn Gly Met Val Arg Glu Leu Ile Asp His Lys Ala Asp Leu
            500                 505                 510

Ala Val Ala Pro Leu Ala Ile Thr Tyr Val Arg Glu Lys Val Ile Asp
        515                 520                 525

Phe Ser Lys Pro Phe Met Thr Leu Gly Ile Ser Ile Leu Tyr Arg Lys
```

```
            530                 535                 540

Pro Asn Gly Thr Asn Pro Gly Val Phe Ser Phe Leu Asn Pro Leu Ser
545                 550                 555                 560

Pro Asp Ile Trp Met Tyr Ile Leu Leu Ala Tyr Leu Gly Val Ser Cys
                565                 570                 575

Val Leu Phe Val Ile Ala Arg Phe Ser Pro Tyr Glu Trp Tyr Asn Pro
            580                 585                 590

His Pro Cys Asn Pro Asp Ser Asp Val Val Glu Asn Asn Phe Thr Leu
        595                 600                 605

Leu Asn Ser Phe Trp Phe Gly Val Gly Ala Leu Met Gln Gln Gly Ser
    610                 615                 620

Glu Leu Met Pro Lys Ala Leu Ser Thr Arg Ile Val Gly Gly Ile Trp
625                 630                 635                 640

Trp Phe Phe Thr Leu Ile Ile Ile Ser Ser Tyr Thr Ala Asn Leu Ala
                645                 650                 655

Ala Phe Leu Thr Val Glu Arg Met Glu Ser Pro Ile Asp Ser Ala Asp
            660                 665                 670

Asp Leu Ala Lys Gln Thr Lys Ile Glu Tyr Gly Ala Val Glu Asp Gly
        675                 680                 685

Ala Thr Met Thr Phe Phe Lys Lys Ser Lys Ile Ser Thr Tyr Asp Lys
    690                 695                 700

Met Trp Ala Phe Met Ser Ser Arg Arg Gln Ser Val Leu Val Lys Ser
705                 710                 715                 720

Asn Glu Glu Gly Ile Gln Arg Val Leu Thr Ser Asp Tyr Ala Phe Leu
                725                 730                 735

Met Glu Ser Thr Thr Ile Glu Phe Val Thr Gln Arg Asn Cys Asn Leu
            740                 745                 750

Thr Gln Ile Gly Gly Leu Ile Asp Ser Lys Gly Tyr Gly Val Gly Thr
        755                 760                 765

Pro Met Gly Ser Pro Tyr Arg Asp Lys Ile Thr Ile Ala Ile Leu Gln
    770                 775                 780

Leu Gln Glu Glu Gly Lys Leu His Met Met Lys Glu Lys Trp Trp Arg
785                 790                 795                 800

Gly Asn Gly Cys Pro Glu Glu Glu Ser Lys Glu Ala Ser Ala Leu Gly
                805                 810                 815

Val Gln Asn Ile Gly Gly Ile Phe Ile Val Leu Ala Ala Gly Leu Val
            820                 825                 830

Leu Ser Val Phe Val Ala Val Gly Glu Phe Leu Tyr Lys Ser Lys Lys
        835                 840                 845

Asn Ala Gln Leu Glu Lys Arg Ser Phe Cys Ser Ala Met Val Glu Glu
    850                 855                 860

Leu Arg Met Ser Leu Lys Cys Gln Arg Arg Leu Lys His Lys Pro Gln
865                 870                 875                 880

Ala Pro Val Ile Val Lys Thr Glu Glu Val Ile Asn Met His Thr Phe
                885                 890                 895

Asn Asp Arg Arg Leu Pro Gly Lys Glu Thr Met Ala
            900                 905
```

<210> SEQ ID NO 5
<211> LENGTH: 869
<212> TYPE: PRT
<213> ORGANISM: Homo sapiens

<400> SEQUENCE: 5

-continued

```
Met Lys Ile Ile Phe Pro Ile Leu Ser Asn Pro Val Phe Arg Arg Thr
1               5                   10                  15

Val Lys Leu Leu Leu Cys Leu Leu Trp Ile Gly Tyr Ser Gln Gly Thr
            20                  25                  30

Thr His Val Leu Arg Phe Gly Gly Ile Phe Glu Tyr Val Glu Ser Gly
        35                  40                  45

Pro Met Gly Ala Glu Glu Leu Ala Phe Arg Phe Ala Val Asn Thr Ile
    50                  55                  60

Asn Arg Asn Arg Thr Leu Leu Pro Asn Thr Thr Leu Thr Tyr Asp Thr
65                  70                  75                  80

Gln Lys Ile Asn Leu Tyr Asp Ser Phe Glu Ala Ser Lys Lys Ala Cys
                85                  90                  95

Asp Gln Leu Ser Leu Gly Val Ala Ala Ile Phe Gly Pro Ser His Ser
            100                 105                 110

Ser Ser Ala Asn Ala Val Gln Ser Ile Cys Asn Ala Leu Gly Val Pro
        115                 120                 125

His Ile Gln Thr Arg Trp Lys His Gln Val Ser Asp Asn Lys Asp Ser
    130                 135                 140

Phe Tyr Val Ser Leu Tyr Pro Asp Phe Ser Ser Leu Ser Arg Ala Ile
145                 150                 155                 160

Leu Asp Leu Val Gln Phe Phe Lys Trp Lys Thr Val Thr Val Val Tyr
                165                 170                 175

Asp Asp Ser Thr Gly Leu Ile Arg Leu Gln Glu Leu Ile Lys Ala Pro
            180                 185                 190

Ser Arg Tyr Asn Leu Arg Leu Lys Ile Arg Gln Leu Pro Ala Asp Thr
        195                 200                 205

Lys Asp Ala Lys Pro Leu Leu Lys Glu Met Lys Arg Gly Lys Glu Phe
    210                 215                 220

His Val Ile Phe Asp Cys Ser His Glu Met Ala Ala Gly Ile Leu Lys
225                 230                 235                 240

Gln Ala Leu Ala Met Gly Met Met Thr Glu Tyr Tyr His Tyr Ile Phe
                245                 250                 255

Thr Thr Leu Asp Leu Phe Ala Leu Asp Val Glu Pro Tyr Arg Tyr Ser
            260                 265                 270

Gly Val Asn Met Thr Gly Phe Arg Ile Leu Asn Thr Glu Asn Thr Gln
        275                 280                 285

Val Ser Ser Ile Ile Glu Lys Trp Ser Met Glu Arg Leu Gln Ala Pro
    290                 295                 300

Pro Lys Pro Asp Ser Gly Leu Leu Asp Gly Phe Met Thr Thr Asp Ala
305                 310                 315                 320

Ala Leu Met Tyr Asp Ala Val His Val Val Ser Val Ala Val Gln Gln
                325                 330                 335

Phe Pro Gln Met Thr Val Ser Ser Leu Gln Cys Asn Arg His Lys Pro
            340                 345                 350

Trp Arg Phe Gly Thr Arg Phe Met Ser Leu Ile Lys Glu Ala His Trp
        355                 360                 365

Glu Gly Leu Thr Gly Arg Ile Thr Phe Asn Lys Thr Asn Gly Leu Arg
    370                 375                 380

Thr Asp Phe Asp Leu Asp Val Ile Ser Leu Lys Glu Glu Gly Leu Glu
385                 390                 395                 400

Lys Ile Gly Thr Trp Asp Pro Ala Ser Gly Leu Asn Met Thr Glu Ser
                405                 410                 415

Gln Lys Gly Lys Pro Ala Asn Ile Thr Asp Ser Leu Ser Asn Arg Ser
```

-continued

```
            420                 425                 430

Leu Ile Val Thr Thr Ile Leu Glu Glu Pro Tyr Val Leu Phe Lys Lys
        435                 440                 445

Ser Asp Lys Pro Leu Tyr Gly Asn Asp Arg Phe Glu Gly Tyr Cys Ile
    450                 455                 460

Asp Leu Leu Arg Glu Leu Ser Thr Ile Leu Gly Phe Thr Tyr Glu Ile
465                 470                 475                 480

Arg Leu Val Glu Asp Gly Lys Tyr Gly Ala Gln Asp Asp Ala Asn Gly
                485                 490                 495

Gln Trp Asn Gly Met Val Arg Glu Leu Ile Asp His Lys Ala Asp Leu
            500                 505                 510

Ala Val Ala Pro Leu Ala Ile Thr Tyr Val Arg Glu Lys Val Ile Asp
        515                 520                 525

Phe Ser Lys Pro Phe Met Thr Leu Gly Ile Ser Ile Leu Tyr Arg Lys
    530                 535                 540

Pro Asn Gly Thr Asn Pro Gly Val Phe Ser Phe Leu Asn Pro Leu Ser
545                 550                 555                 560

Pro Asp Ile Trp Met Tyr Ile Leu Leu Ala Tyr Leu Gly Val Ser Cys
                565                 570                 575

Val Leu Phe Val Ile Ala Arg Phe Ser Pro Tyr Glu Trp Tyr Asn Pro
            580                 585                 590

His Pro Cys Asn Pro Asp Ser Asp Val Val Glu Asn Asn Phe Thr Leu
        595                 600                 605

Leu Asn Ser Phe Trp Phe Gly Val Gly Ala Leu Met Gln Gln Gly Ser
    610                 615                 620

Glu Leu Met Pro Lys Ala Leu Ser Thr Arg Ile Val Gly Gly Ile Trp
625                 630                 635                 640

Trp Phe Phe Thr Leu Ile Ile Ile Ser Ser Tyr Thr Ala Asn Leu Ala
                645                 650                 655

Ala Phe Leu Thr Val Glu Arg Met Glu Ser Pro Ile Asp Ser Ala Asp
            660                 665                 670

Asp Leu Ala Lys Gln Thr Lys Ile Glu Tyr Gly Ala Val Glu Asp Gly
        675                 680                 685

Ala Thr Met Thr Phe Phe Lys Lys Ser Lys Ile Ser Thr Tyr Asp Lys
    690                 695                 700

Met Trp Ala Phe Met Ser Ser Arg Arg Gln Ser Val Leu Val Lys Ser
705                 710                 715                 720

Asn Glu Glu Gly Ile Gln Arg Val Leu Thr Ser Asp Tyr Ala Phe Leu
                725                 730                 735

Met Glu Ser Thr Thr Ile Glu Phe Val Thr Gln Arg Asn Cys Asn Leu
            740                 745                 750

Thr Gln Ile Gly Gly Leu Ile Asp Ser Lys Gly Tyr Gly Val Gly Thr
        755                 760                 765

Pro Met Gly Ser Pro Tyr Arg Asp Lys Ile Thr Ile Ala Ile Leu Gln
    770                 775                 780

Leu Gln Glu Glu Gly Lys Leu His Met Met Lys Glu Lys Trp Trp Arg
785                 790                 795                 800

Gly Asn Gly Cys Pro Glu Glu Glu Ser Lys Glu Ala Ser Ala Leu Gly
                805                 810                 815

Val Gln Asn Ile Gly Gly Ile Phe Ile Val Leu Ala Ala Gly Leu Val
            820                 825                 830

Leu Ser Val Phe Val Ala Val Gly Glu Phe Leu Tyr Lys Ser Lys Lys
        835                 840                 845
```

Asn Ala Gln Leu Glu Lys Glu Ser Ser Ile Trp Leu Val Pro Pro Tyr
    850                 855                 860

His Pro Asp Thr Val
865

<210> SEQ ID NO 6
<211> LENGTH: 584
<212> TYPE: PRT
<213> ORGANISM: Homo sapiens

<400> SEQUENCE: 6

Met Lys Ile Ile Phe Pro Ile Leu Ser Asn Pro Val Phe Arg Arg Thr
1               5                   10                  15

Val Lys Leu Leu Leu Cys Leu Leu Trp Ile Gly Tyr Ser Gln Gly Thr
            20                  25                  30

Thr His Val Leu Arg Phe Gly Gly Ile Phe Glu Tyr Val Glu Ser Gly
        35                  40                  45

Pro Met Gly Ala Glu Glu Leu Ala Phe Arg Phe Ala Val Asn Thr Ile
    50                  55                  60

Asn Arg Asn Arg Thr Leu Leu Pro Asn Thr Thr Leu Thr Tyr Asp Thr
65                  70                  75                  80

Gln Lys Ile Asn Leu Tyr Asp Ser Phe Glu Ala Ser Lys Lys Ala Cys
                85                  90                  95

Asp Gln Leu Ser Leu Gly Val Ala Ala Ile Phe Gly Pro Ser His Ser
            100                 105                 110

Ser Ser Ala Asn Ala Val Gln Ser Ile Cys Asn Ala Leu Gly Val Pro
        115                 120                 125

His Ile Gln Thr Arg Trp Lys His Gln Val Ser Asp Asn Lys Asp Ser
    130                 135                 140

Phe Tyr Val Ser Leu Tyr Pro Asp Phe Ser Ser Leu Ser Arg Ala Ile
145                 150                 155                 160

Leu Asp Leu Val Gln Phe Phe Lys Trp Lys Thr Val Thr Val Val Tyr
                165                 170                 175

Asp Asp Ser Thr Gly Leu Ile Arg Leu Gln Glu Leu Ile Lys Ala Pro
            180                 185                 190

Ser Arg Tyr Asn Leu Arg Leu Lys Ile Arg Gln Leu Pro Ala Asp Thr
        195                 200                 205

Lys Asp Ala Lys Pro Leu Leu Lys Glu Met Lys Arg Gly Lys Glu Phe
    210                 215                 220

His Val Ile Phe Asp Cys Ser His Glu Met Ala Ala Gly Ile Leu Lys
225                 230                 235                 240

Gln Ala Leu Ala Met Gly Met Met Thr Glu Tyr Tyr His Tyr Ile Phe
                245                 250                 255

Thr Thr Leu Asp Leu Phe Ala Leu Asp Val Glu Pro Tyr Arg Tyr Ser
            260                 265                 270

Gly Val Asn Met Thr Gly Phe Arg Ile Leu Asn Thr Glu Asn Thr Gln
        275                 280                 285

Val Ser Ser Ile Ile Glu Lys Trp Ser Met Glu Arg Leu Gln Ala Pro
    290                 295                 300

Pro Lys Pro Asp Ser Gly Leu Leu Asp Gly Phe Met Thr Thr Asp Ala
305                 310                 315                 320

Ala Leu Met Tyr Asp Ala Val His Val Val Ser Val Ala Val Gln Gln
                325                 330                 335

Phe Pro Gln Met Thr Val Ser Ser Leu Gln Cys Asn Arg His Lys Pro

```
            340                 345                 350

Trp Arg Phe Gly Thr Arg Phe Met Ser Leu Ile Lys Glu Ala His Trp
        355                 360                 365

Glu Gly Leu Thr Gly Arg Ile Thr Phe Asn Lys Thr Asn Gly Leu Arg
    370                 375                 380

Thr Asp Phe Asp Leu Asp Val Ile Ser Leu Lys Glu Glu Gly Leu Glu
385                 390                 395                 400

Lys Ile Gly Thr Trp Asp Pro Ala Ser Gly Leu Asn Met Thr Glu Ser
                405                 410                 415

Gln Lys Gly Lys Pro Ala Asn Ile Thr Asp Ser Leu Ser Asn Arg Ser
            420                 425                 430

Leu Ile Val Thr Thr Ile Leu Glu Glu Pro Tyr Val Leu Phe Lys Lys
        435                 440                 445

Ser Asp Lys Pro Leu Tyr Gly Asn Asp Arg Phe Glu Gly Tyr Cys Ile
    450                 455                 460

Asp Leu Leu Arg Glu Leu Ser Thr Ile Leu Gly Phe Thr Tyr Glu Ile
465                 470                 475                 480

Arg Leu Val Glu Asp Gly Lys Tyr Gly Ala Gln Asp Asp Ala Asn Gly
                485                 490                 495

Gln Trp Asn Gly Met Val Arg Glu Leu Ile Asp His Lys Ala Asp Leu
            500                 505                 510

Ala Val Ala Pro Leu Ala Ile Thr Tyr Val Arg Glu Lys Val Ile Asp
        515                 520                 525

Phe Ser Lys Pro Phe Met Thr Leu Gly Ile Ser Ile Leu Tyr Arg Lys
    530                 535                 540

Pro Asn Gly Thr Asn Pro Gly Val Phe Ser Phe Leu Asn Pro Leu Ser
545                 550                 555                 560

Pro Asp Ile Trp Met Tyr Ile Leu Leu Ala Tyr Leu Gly Val Ser Cys
                565                 570                 575

Val Leu Phe Val Ile Ala Arg Phe
            580


<210> SEQ ID NO 7
<211> LENGTH: 832
<212> TYPE: PRT
<213> ORGANISM: Homo sapiens

<400> SEQUENCE: 7

Met Lys Ile Ile Phe Pro Ile Leu Ser Asn Pro Val Phe Arg Arg Thr
1               5                   10                  15

Val Lys Leu Leu Leu Cys Leu Leu Trp Ile Gly Tyr Ser Gln Gly Thr
            20                  25                  30

Thr His Val Leu Arg Phe Gly Gly Ile Phe Glu Tyr Val Glu Ser Gly
        35                  40                  45

Pro Met Gly Ala Glu Glu Leu Ala Phe Arg Phe Ala Val Asn Thr Ile
    50                  55                  60

Asn Arg Asn Arg Thr Leu Leu Pro Asn Thr Thr Leu Thr Tyr Asp Thr
65                  70                  75                  80

Gln Lys Ile Asn Leu Tyr Asp Ser Phe Glu Ala Ser Lys Lys Ala Cys
                85                  90                  95

Asp Gln Leu Ser Leu Gly Val Ala Ala Ile Phe Gly Pro Ser His Ser
            100                 105                 110

Ser Ser Ala Asn Ala Val Gln Ser Ile Cys Asn Ala Leu Gly Val Pro
        115                 120                 125
```

```
His Ile Gln Thr Arg Trp Lys His Gln Val Ser Asp Asn Lys Asp Ser
    130                 135                 140

Phe Tyr Val Ser Leu Tyr Pro Asp Phe Ser Ser Leu Ser Arg Ala Ile
145                 150                 155                 160

Leu Asp Leu Val Gln Phe Phe Lys Trp Lys Thr Val Thr Val Val Tyr
                165                 170                 175

Asp Asp Ser Thr Gly Leu Ile Arg Leu Gln Glu Leu Ile Lys Ala Pro
            180                 185                 190

Ser Arg Tyr Asn Leu Arg Leu Lys Ile Arg Gln Leu Pro Ala Asp Thr
        195                 200                 205

Lys Asp Ala Lys Pro Leu Leu Lys Glu Met Lys Arg Gly Lys Glu Phe
    210                 215                 220

His Val Ile Phe Asp Cys Ser His Glu Met Ala Ala Gly Ile Leu Lys
225                 230                 235                 240

Gln Ala Leu Ala Met Gly Met Met Thr Glu Tyr Tyr His Tyr Ile Phe
                245                 250                 255

Thr Thr Leu Asp Leu Phe Ala Leu Asp Val Glu Pro Tyr Arg Tyr Ser
            260                 265                 270

Gly Val Asn Met Thr Gly Phe Arg Ile Leu Asn Thr Glu Asn Thr Gln
        275                 280                 285

Val Ser Ser Ile Ile Glu Lys Trp Ser Met Glu Arg Leu Gln Ala Pro
    290                 295                 300

Pro Lys Pro Asp Ser Gly Leu Leu Asp Gly Phe Met Thr Thr Asp Ala
305                 310                 315                 320

Ala Leu Met Tyr Asp Ala Val His Val Val Ser Val Ala Val Gln Gln
                325                 330                 335

Phe Pro Gln Met Thr Val Ser Ser Leu Gln Cys Asn Arg His Lys Pro
            340                 345                 350

Trp Arg Phe Gly Thr Arg Phe Met Ser Leu Ile Lys Glu Ala His Trp
        355                 360                 365

Glu Gly Leu Thr Gly Arg Ile Thr Phe Asn Lys Thr Asn Gly Leu Arg
    370                 375                 380

Thr Asp Phe Asp Leu Asp Val Ile Ser Leu Lys Glu Glu Gly Leu Glu
385                 390                 395                 400

Lys Ile Gly Thr Trp Asp Pro Ala Ser Gly Leu Asn Met Thr Glu Ser
                405                 410                 415

Gln Lys Gly Lys Pro Ala Asn Ile Thr Asp Ser Leu Ser Asn Arg Ser
            420                 425                 430

Leu Ile Val Thr Thr Ile Leu Glu Glu Pro Tyr Val Leu Phe Lys Lys
        435                 440                 445

Ser Asp Lys Pro Leu Tyr Gly Asn Asp Arg Phe Glu Gly Tyr Cys Ile
    450                 455                 460

Asp Leu Leu Arg Glu Leu Ser Thr Ile Leu Gly Phe Thr Tyr Glu Ile
465                 470                 475                 480

Arg Leu Val Glu Asp Gly Lys Tyr Gly Ala Gln Asp Asp Ala Asn Gly
                485                 490                 495

Gln Trp Asn Gly Met Val Arg Glu Leu Ile Asp His Lys Ala Asp Leu
            500                 505                 510

Ala Val Ala Pro Leu Ala Ile Thr Tyr Val Arg Glu Lys Val Ile Asp
        515                 520                 525

Phe Ser Lys Pro Phe Met Thr Leu Gly Ile Ser Ile Leu Tyr Arg Lys
    530                 535                 540

Pro Asn Gly Ser Glu Leu Met Pro Lys Ala Leu Ser Thr Arg Ile Val
```

```
545                 550                 555                 560

Gly Gly Ile Trp Trp Phe Phe Thr Leu Ile Ile Ile Ser Ser Tyr Thr
                565                 570                 575

Ala Asn Leu Ala Ala Phe Leu Thr Val Glu Arg Met Glu Ser Pro Ile
            580                 585                 590

Asp Ser Ala Asp Asp Leu Ala Lys Gln Thr Lys Ile Glu Tyr Gly Ala
        595                 600                 605

Val Glu Asp Gly Ala Thr Met Thr Phe Phe Lys Lys Ser Lys Ile Ser
    610                 615                 620

Thr Tyr Asp Lys Met Trp Ala Phe Met Ser Ser Arg Arg Gln Ser Val
625                 630                 635                 640

Leu Val Lys Ser Asn Glu Glu Gly Ile Gln Arg Val Leu Thr Ser Asp
                645                 650                 655

Tyr Ala Phe Leu Met Glu Ser Thr Thr Ile Glu Phe Val Thr Gln Arg
            660                 665                 670

Asn Cys Asn Leu Thr Gln Ile Gly Gly Leu Ile Asp Ser Lys Gly Tyr
        675                 680                 685

Gly Val Gly Thr Pro Met Gly Ser Pro Tyr Arg Asp Lys Ile Thr Ile
    690                 695                 700

Ala Ile Leu Gln Leu Gln Glu Glu Gly Lys Leu His Met Met Lys Glu
705                 710                 715                 720

Lys Trp Trp Arg Gly Asn Gly Cys Pro Glu Glu Glu Ser Lys Glu Ala
                725                 730                 735

Ser Ala Leu Gly Val Gln Asn Ile Gly Gly Ile Phe Ile Val Leu Ala
            740                 745                 750

Ala Gly Leu Val Leu Ser Val Phe Val Ala Val Gly Glu Phe Leu Tyr
        755                 760                 765

Lys Ser Lys Lys Asn Ala Gln Leu Glu Lys Arg Ser Phe Cys Ser Ala
    770                 775                 780

Met Val Glu Glu Leu Arg Met Ser Leu Lys Cys Gln Arg Arg Leu Lys
785                 790                 795                 800

His Lys Pro Gln Ala Pro Val Ile Val Lys Thr Glu Glu Val Ile Asn
                805                 810                 815

Met His Thr Phe Asn Asp Arg Arg Leu Pro Gly Lys Glu Thr Met Ala
            820                 825                 830


<210> SEQ ID NO 8
<211> LENGTH: 892
<212> TYPE: PRT
<213> ORGANISM: Homo sapiens

<400> SEQUENCE: 8

Met Lys Ile Ile Phe Pro Ile Leu Ser Asn Pro Val Phe Arg Arg Thr
1               5                   10                  15

Val Lys Leu Leu Leu Cys Leu Leu Trp Ile Gly Tyr Ser Gln Gly Thr
            20                  25                  30

Thr His Val Leu Arg Phe Gly Gly Ile Phe Glu Tyr Val Glu Ser Gly
        35                  40                  45

Pro Met Gly Ala Glu Glu Leu Ala Phe Arg Phe Ala Val Asn Thr Ile
    50                  55                  60

Asn Arg Asn Arg Thr Leu Leu Pro Asn Thr Thr Leu Thr Tyr Asp Thr
65                  70                  75                  80

Gln Lys Ile Asn Leu Tyr Asp Ser Phe Glu Ala Ser Lys Lys Ala Cys
                85                  90                  95
```

```
Asp Gln Leu Ser Leu Gly Val Ala Ala Ile Phe Gly Pro Ser His Ser
            100                 105                 110

Ser Ser Ala Asn Ala Val Gln Ser Ile Cys Asn Ala Leu Gly Val Pro
        115                 120                 125

His Ile Gln Thr Arg Trp Lys His Gln Val Ser Asp Asn Lys Asp Ser
    130                 135                 140

Phe Tyr Val Ser Leu Tyr Pro Asp Phe Ser Ser Leu Ser Arg Ala Ile
145                 150                 155                 160

Leu Asp Leu Val Gln Phe Phe Lys Trp Lys Thr Val Thr Val Val Tyr
                165                 170                 175

Asp Asp Ser Thr Gly Leu Ile Arg Leu Gln Glu Leu Ile Lys Ala Pro
            180                 185                 190

Ser Arg Tyr Asn Leu Arg Leu Lys Ile Arg Gln Leu Pro Ala Asp Thr
        195                 200                 205

Lys Asp Ala Lys Pro Leu Leu Lys Glu Met Lys Arg Gly Lys Glu Phe
    210                 215                 220

His Val Ile Phe Asp Cys Ser His Glu Met Ala Ala Gly Ile Leu Lys
225                 230                 235                 240

Gln Ala Leu Ala Met Gly Met Met Thr Glu Tyr Tyr His Tyr Ile Phe
                245                 250                 255

Thr Thr Leu Asp Leu Phe Ala Leu Asp Val Glu Pro Tyr Arg Tyr Ser
            260                 265                 270

Gly Val Asn Met Thr Gly Phe Arg Ile Leu Asn Thr Glu Asn Thr Gln
        275                 280                 285

Val Ser Ser Ile Ile Glu Lys Trp Ser Met Glu Arg Leu Gln Ala Pro
    290                 295                 300

Pro Lys Pro Asp Ser Gly Leu Leu Asp Gly Phe Met Thr Thr Asp Ala
305                 310                 315                 320

Ala Leu Met Tyr Asp Ala Val His Val Val Ser Val Ala Val Gln Gln
                325                 330                 335

Phe Pro Gln Met Thr Val Ser Ser Leu Gln Cys Asn Arg His Lys Pro
            340                 345                 350

Trp Arg Phe Gly Thr Arg Phe Met Ser Leu Ile Lys Glu Ala His Trp
        355                 360                 365

Glu Gly Leu Thr Gly Arg Ile Thr Phe Asn Lys Thr Asn Gly Leu Arg
    370                 375                 380

Thr Asp Phe Asp Leu Asp Val Ile Ser Leu Lys Glu Glu Gly Leu Glu
385                 390                 395                 400

Lys Ile Gly Thr Trp Asp Pro Ala Ser Gly Leu Asn Met Thr Glu Ser
                405                 410                 415

Gln Lys Gly Lys Pro Ala Asn Ile Thr Asp Ser Leu Ser Asn Arg Ser
            420                 425                 430

Leu Ile Val Thr Thr Ile Leu Glu Glu Pro Tyr Val Leu Phe Lys Lys
        435                 440                 445

Ser Asp Lys Pro Leu Tyr Gly Asn Asp Arg Phe Glu Gly Tyr Cys Ile
    450                 455                 460

Asp Leu Leu Arg Glu Leu Ser Thr Ile Leu Gly Phe Thr Tyr Glu Ile
465                 470                 475                 480

Arg Leu Val Glu Asp Gly Lys Tyr Gly Ala Gln Asp Asp Ala Asn Gly
                485                 490                 495

Gln Trp Asn Gly Met Val Arg Glu Leu Ile Asp His Lys Ala Asp Leu
            500                 505                 510

Ala Val Ala Pro Leu Ala Ile Thr Tyr Val Arg Glu Lys Val Ile Asp
```

```
        515                 520                 525

Phe Ser Lys Pro Phe Met Thr Leu Gly Ile Ser Ile Leu Tyr Arg Lys
    530                 535                 540

Pro Asn Gly Thr Asn Pro Gly Val Phe Ser Phe Leu Asn Pro Leu Ser
545                 550                 555                 560

Pro Asp Ile Trp Met Tyr Ile Leu Leu Ala Tyr Leu Gly Val Ser Cys
                565                 570                 575

Val Leu Phe Val Ile Ala Arg Phe Ser Pro Tyr Glu Trp Tyr Asn Pro
            580                 585                 590

His Pro Cys Asn Pro Asp Ser Asp Val Val Glu Asn Asn Phe Thr Leu
        595                 600                 605

Leu Asn Ser Phe Trp Phe Gly Val Gly Ala Leu Met Gln Gln Gly Ser
    610                 615                 620

Glu Leu Met Pro Lys Ala Leu Ser Thr Arg Ile Val Gly Gly Ile Trp
625                 630                 635                 640

Trp Phe Phe Thr Leu Ile Ile Ile Ser Ser Tyr Thr Ala Asn Leu Ala
                645                 650                 655

Ala Phe Leu Thr Val Glu Arg Met Glu Ser Pro Ile Asp Ser Ala Asp
            660                 665                 670

Asp Leu Ala Lys Gln Thr Lys Ile Glu Tyr Gly Ala Val Glu Asp Gly
        675                 680                 685

Ala Thr Met Thr Phe Phe Lys Lys Ser Lys Ile Ser Thr Tyr Asp Lys
    690                 695                 700

Met Trp Ala Phe Met Ser Ser Arg Arg Gln Ser Val Leu Val Lys Ser
705                 710                 715                 720

Asn Glu Glu Gly Ile Gln Arg Val Leu Thr Ser Asp Tyr Ala Phe Leu
                725                 730                 735

Met Glu Ser Thr Thr Ile Glu Phe Val Thr Gln Arg Asn Cys Asn Leu
            740                 745                 750

Thr Gln Ile Gly Gly Leu Ile Asp Ser Lys Gly Tyr Gly Val Gly Thr
        755                 760                 765

Pro Met Gly Ser Pro Tyr Arg Asp Lys Ile Thr Ile Ala Ile Leu Gln
    770                 775                 780

Leu Gln Glu Glu Gly Lys Leu His Met Met Lys Glu Lys Trp Trp Arg
785                 790                 795                 800

Gly Asn Gly Cys Pro Glu Glu Glu Ser Lys Glu Ala Ser Ala Leu Gly
                805                 810                 815

Val Gln Asn Ile Gly Gly Ile Phe Ile Val Leu Ala Ala Gly Leu Val
            820                 825                 830

Leu Ser Val Phe Val Ala Val Gly Glu Phe Leu Tyr Lys Ser Lys Lys
        835                 840                 845

Asn Ala Gln Leu Glu Lys Arg Ala Lys Thr Lys Leu Pro Gln Asp Tyr
    850                 855                 860

Val Phe Leu Pro Ile Leu Glu Ser Val Ser Ile Ser Thr Val Leu Ser
865                 870                 875                 880

Ser Ser Pro Ser Ser Ser Ser Leu Ser Ser Cys Ser
                885                 890
```

<210> SEQ ID NO 9
<211> LENGTH: 682
<212> TYPE: PRT
<213> ORGANISM: Homo sapiens

<400> SEQUENCE: 9

```
Met Lys Ile Ile Phe Pro Ile Leu Ser Asn Pro Val Phe Arg Arg Thr
1               5                   10                  15

Val Lys Leu Leu Leu Cys Leu Leu Trp Ile Gly Tyr Ser Gln Gly Thr
            20                  25                  30

Thr His Val Leu Arg Phe Gly Gly Ile Phe Glu Tyr Val Glu Ser Gly
        35                  40                  45

Pro Met Gly Ala Glu Glu Leu Ala Phe Arg Phe Ala Val Asn Thr Ile
    50                  55                  60

Asn Arg Asn Arg Thr Leu Leu Pro Asn Thr Thr Leu Thr Tyr Asp Thr
65                  70                  75                  80

Gln Lys Ile Asn Leu Tyr Asp Ser Phe Glu Ala Ser Lys Lys Ala Cys
                85                  90                  95

Asp Gln Leu Ser Leu Gly Val Ala Ala Ile Phe Gly Pro Ser His Ser
            100                 105                 110

Ser Ser Ala Asn Ala Val Gln Ser Ile Cys Asn Ala Leu Gly Val Pro
        115                 120                 125

His Ile Gln Thr Arg Trp Lys His Gln Val Ser Asp Asn Lys Asp Ser
    130                 135                 140

Phe Tyr Val Ser Leu Tyr Pro Asp Phe Ser Ser Leu Ser Arg Ala Ile
145                 150                 155                 160

Leu Asp Leu Val Gln Phe Phe Lys Trp Lys Thr Val Thr Val Val Tyr
                165                 170                 175

Asp Asp Ser Thr Gly Leu Ile Arg Leu Gln Glu Leu Ile Lys Ala Pro
            180                 185                 190

Ser Arg Tyr Asn Leu Arg Leu Lys Ile Arg Gln Leu Pro Ala Asp Thr
        195                 200                 205

Lys Asp Ala Lys Pro Leu Leu Lys Glu Met Lys Arg Gly Lys Glu Phe
    210                 215                 220

His Val Ile Phe Asp Cys Ser His Glu Met Ala Ala Gly Ile Leu Lys
225                 230                 235                 240

Gln Ala Leu Ala Met Gly Met Met Thr Glu Tyr Tyr His Tyr Ile Phe
                245                 250                 255

Thr Thr Leu Asp Leu Phe Ala Leu Asp Val Glu Pro Tyr Arg Tyr Ser
            260                 265                 270

Gly Val Asn Met Thr Gly Phe Arg Ile Leu Asn Thr Glu Asn Thr Gln
        275                 280                 285

Val Ser Ser Ile Ile Glu Lys Trp Ser Met Glu Arg Leu Gln Ala Pro
    290                 295                 300

Pro Lys Pro Asp Ser Gly Leu Leu Asp Gly Phe Met Thr Thr Asp Ala
305                 310                 315                 320

Ala Leu Met Tyr Asp Ala Val His Val Val Ser Val Ala Val Gln Gln
                325                 330                 335

Phe Pro Gln Met Thr Val Ser Ser Leu Gln Cys Asn Arg His Lys Pro
            340                 345                 350

Trp Arg Phe Gly Thr Arg Phe Met Ser Leu Ile Lys Glu Ala His Trp
        355                 360                 365

Glu Gly Leu Thr Gly Arg Ile Thr Phe Asn Lys Thr Asn Gly Leu Arg
    370                 375                 380

Thr Asp Phe Asp Leu Asp Val Ile Ser Leu Lys Glu Glu Gly Leu Glu
385                 390                 395                 400

Lys Ile Gly Thr Trp Asp Pro Ala Ser Gly Leu Asn Met Thr Glu Ser
                405                 410                 415

Gln Lys Gly Lys Pro Ala Asn Ile Thr Asp Ser Leu Ser Asn Arg Ser
```

```
            420                 425                 430

Leu Ile Val Thr Thr Ile Leu Glu Glu Pro Tyr Val Leu Phe Lys Lys
        435                 440                 445

Ser Asp Lys Pro Leu Tyr Gly Asn Asp Arg Phe Glu Gly Tyr Cys Ile
    450                 455                 460

Asp Leu Leu Arg Glu Leu Ser Thr Ile Leu Gly Phe Thr Tyr Glu Ile
465                 470                 475                 480

Arg Leu Val Glu Asp Gly Lys Tyr Gly Ala Gln Asp Asp Ala Asn Gly
                485                 490                 495

Gln Trp Asn Gly Met Val Arg Glu Leu Ile Asp His Lys Ser Lys Ile
            500                 505                 510

Ser Thr Tyr Asp Lys Met Trp Ala Phe Met Ser Ser Arg Arg Gln Ser
        515                 520                 525

Val Leu Val Lys Ser Asn Glu Glu Gly Ile Gln Arg Val Leu Thr Ser
    530                 535                 540

Asp Tyr Ala Phe Leu Met Glu Ser Thr Thr Ile Glu Phe Val Thr Gln
545                 550                 555                 560

Arg Asn Cys Asn Leu Thr Gln Ile Gly Gly Leu Ile Asp Ser Lys Gly
                565                 570                 575

Tyr Gly Val Gly Thr Pro Met Gly Ser Pro Tyr Arg Asp Lys Ile Thr
            580                 585                 590

Ile Ala Ile Leu Gln Leu Gln Glu Glu Gly Lys Leu His Met Met Lys
        595                 600                 605

Glu Lys Trp Trp Arg Gly Asn Gly Cys Pro Glu Glu Glu Ser Lys Glu
    610                 615                 620

Ala Ser Ala Leu Gly Val Gln Asn Ile Gly Gly Ile Phe Ile Val Leu
625                 630                 635                 640

Ala Ala Gly Leu Val Leu Ser Val Phe Val Ala Val Gly Glu Phe Leu
                645                 650                 655

Tyr Lys Ser Lys Lys Asn Ala Gln Leu Glu Lys Glu Ser Ser Ile Trp
            660                 665                 670

Leu Val Pro Pro Tyr His Pro Asp Thr Val
        675                 680


<210> SEQ ID NO 10
<211> LENGTH: 687
<212> TYPE: PRT
<213> ORGANISM: Homo sapiens

<400> SEQUENCE: 10

Met Lys Ile Ile Phe Pro Ile Leu Ser Asn Pro Val Phe Arg Arg Thr
1               5                   10                  15

Val Lys Leu Leu Leu Cys Leu Leu Trp Ile Gly Tyr Ser Gln Gly Thr
            20                  25                  30

Thr His Val Leu Arg Phe Gly Gly Ile Phe Glu Tyr Val Glu Ser Gly
        35                  40                  45

Pro Met Gly Ala Glu Glu Leu Ala Phe Arg Phe Ala Val Asn Thr Ile
    50                  55                  60

Asn Arg Asn Arg Thr Leu Leu Pro Asn Thr Thr Leu Thr Tyr Asp Thr
65                  70                  75                  80

Gln Lys Ile Asn Leu Tyr Asp Ser Phe Glu Ala Ser Lys Lys Ala Cys
                85                  90                  95

Asp Gln Leu Ser Leu Gly Val Ala Ala Ile Phe Gly Pro Ser His Ser
            100                 105                 110
```

-continued

```
Ser Ser Ala Asn Ala Val Gln Ser Ile Cys Asn Ala Leu Gly Val Pro
        115                 120                 125

His Ile Gln Thr Arg Trp Lys His Gln Val Ser Asp Asn Lys Asp Ser
    130                 135                 140

Phe Tyr Val Ser Leu Tyr Pro Asp Phe Ser Ser Leu Ser Arg Ala Ile
145                 150                 155                 160

Leu Asp Leu Val Gln Phe Phe Lys Trp Lys Thr Val Thr Val Val Tyr
                165                 170                 175

Asp Asp Ser Thr Gly Leu Ile Arg Leu Gln Glu Leu Ile Lys Ala Pro
            180                 185                 190

Ser Arg Tyr Asn Leu Arg Leu Lys Ile Arg Gln Leu Pro Ala Asp Thr
        195                 200                 205

Lys Asp Ala Lys Pro Leu Leu Lys Glu Met Lys Arg Gly Lys Glu Phe
    210                 215                 220

His Val Ile Phe Asp Cys Ser His Glu Met Ala Ala Gly Ile Leu Lys
225                 230                 235                 240

Gln Ala Leu Ala Met Gly Met Met Thr Glu Tyr Tyr His Tyr Ile Phe
                245                 250                 255

Thr Thr Leu Asp Leu Phe Ala Leu Asp Val Glu Pro Tyr Arg Tyr Ser
            260                 265                 270

Gly Val Asn Met Thr Gly Phe Arg Ile Leu Asn Thr Glu Asn Thr Gln
        275                 280                 285

Val Ser Ser Ile Ile Glu Lys Trp Ser Met Glu Arg Leu Gln Ala Pro
    290                 295                 300

Pro Lys Pro Asp Ser Gly Leu Leu Asp Gly Phe Met Thr Thr Asp Ala
305                 310                 315                 320

Ala Leu Met Tyr Asp Ala Val His Val Val Ser Val Ala Val Gln Gln
                325                 330                 335

Phe Pro Gln Met Thr Val Ser Ser Leu Gln Cys Asn Arg His Lys Pro
            340                 345                 350

Trp Arg Phe Gly Thr Arg Phe Met Ser Leu Ile Lys Glu Ala His Trp
        355                 360                 365

Glu Gly Leu Thr Gly Arg Ile Thr Phe Asn Lys Thr Asn Gly Leu Arg
    370                 375                 380

Thr Asp Phe Asp Leu Asp Val Ile Ser Leu Lys Glu Glu Gly Leu Glu
385                 390                 395                 400

Lys Ile Gly Thr Trp Asp Pro Ala Ser Gly Leu Asn Met Thr Glu Ser
                405                 410                 415

Gln Lys Gly Lys Pro Ala Asn Ile Thr Asp Ser Leu Ser Asn Arg Ser
            420                 425                 430

Leu Ile Val Thr Thr Ile Leu Glu Glu Pro Tyr Val Leu Phe Lys Lys
        435                 440                 445

Ser Asp Lys Pro Leu Tyr Gly Asn Asp Arg Phe Glu Gly Tyr Cys Ile
    450                 455                 460

Asp Leu Leu Arg Glu Leu Ser Thr Ile Leu Gly Phe Thr Tyr Glu Ile
465                 470                 475                 480

Arg Leu Val Glu Asp Gly Lys Tyr Gly Ala Gln Asp Asp Ala Asn Gly
                485                 490                 495

Gln Trp Asn Gly Met Val Arg Glu Leu Ile Asp His Lys Ser Val Leu
            500                 505                 510

Val Lys Ser Asn Glu Glu Gly Ile Gln Arg Val Leu Thr Ser Asp Tyr
        515                 520                 525

Ala Phe Leu Met Glu Ser Thr Thr Ile Glu Phe Val Thr Gln Arg Asn
```

-continued

```
    530                 535                 540

Cys Asn Leu Thr Gln Ile Gly Gly Leu Ile Asp Ser Lys Gly Tyr Gly
545                 550                 555                 560

Val Gly Thr Pro Met Gly Ser Pro Tyr Arg Asp Lys Ile Thr Ile Ala
                565                 570                 575

Ile Leu Gln Leu Gln Glu Glu Gly Lys Leu His Met Met Lys Glu Lys
            580                 585                 590

Trp Trp Arg Gly Asn Gly Cys Pro Glu Glu Glu Ser Lys Glu Ala Ser
        595                 600                 605

Ala Leu Gly Val Gln Asn Ile Gly Gly Ile Phe Ile Val Leu Ala Ala
    610                 615                 620

Gly Leu Val Leu Ser Val Phe Val Ala Val Gly Glu Phe Leu Tyr Lys
625                 630                 635                 640

Ser Lys Lys Asn Ala Gln Leu Glu Lys Arg Ala Lys Thr Lys Leu Pro
                645                 650                 655

Gln Asp Tyr Val Phe Leu Pro Ile Leu Glu Ser Val Ser Ile Ser Thr
            660                 665                 670

Val Leu Ser Ser Ser Pro Ser Ser Ser Ser Leu Ser Ser Cys Ser
        675                 680                 685


<210> SEQ ID NO 11
<211> LENGTH: 2727
<212> TYPE: DNA
<213> ORGANISM: Homo sapiens

<400> SEQUENCE: 11

atgaagatta ttttcccgat tctaagtaat ccagtcttca ggcgcaccgt taaactcctg     60

ctctgtttac tgtggattgg atattctcaa ggaaccacac atgtattaag atttggtggt    120

atttttgaat atgtggaatc tggcccaatg ggagctgagg aacttgcatt cagatttgct    180

gtgaacacaa ttaacagaaa cagaacattg ctacccaata ctacccttac ctatgatacc    240

cagaagataa acctttatga tagttttgaa gcatccaaga aagcctgtga tcagctgtct    300

cttggggtgg ctgccatctt cgggccttca cacagctcat cagcaaacgc agtgcagtcc    360

atctgcaatg ctctgggagt tccccacata cagacccgct ggaagcacca ggtgtcagac    420

aacaaagatt ccttctatgt cagtctctac ccagacttct cttcactcag ccgtgccatt    480

ttagacctgg tgcagttttt caagtggaaa accgtcacgg ttgtgtatga tgacagcact    540

ggtctcattc gtttgcaaga gctcatcaaa gctccatcaa ggtataatct tcgactcaaa    600

attcgtcagt tacctgctga tacaaaggat gcaaaaccct tactaaaaga aatgaaaaga    660

ggcaaggagt ttcatgtaat ctttgattgt agccatgaaa tggcagcagg cattttaaaa    720

caggcattag ctatgggaat gatgacagaa tactatcatt atatctttac cactctggac    780

ctctttgctc ttgatgttga gccctaccga tacagtggtg ttaacatgac agggttcaga    840

atattaaata cagaaaatac ccaagtctcc tccatcattg aaaagtggtc gatggaacga    900

ttgcaggcac ctccgaaacc cgattcaggt ttgctggatg gatttatgac gactgatgct    960

gctctaatgt atgatgctgt gcatgtggtg tctgtggccg ttcaacagtt tccccagatg   1020

acagtcagtt ccttgcagtg taatcgacat aaaccctggc gcttcgggac ccgctttatg   1080

agtctaatta aagaggcaca ttgggaaggc ctcacaggca gaataacttt caacaaaacc   1140

aatggcttga gaacagattt tgatttggat gtgatcagtc tgaaggaaga aggtctagaa   1200

aagattggaa cgtgggatcc agccagtggc ctgaatatga cagaaagtca aaagggaaag   1260
```

```
ccagcgaaca tcacagattc cttatccaat cgttctttga ttgttaccac cattttggaa   1320
gagccttatg tcctttttaa gaagtctgac aaacctctct atggtaatga tcgatttgaa   1380
ggctattgca ttgatctcct cagagagtta tctacaatcc ttggctttac atatgaaatt   1440
agacttgtgg aagatgggaa atatggagcc caggatgatg ccaatggaca atggaatgga   1500
atggttcgtg aactaattga tcataaagct gaccttgcag ttgctccact ggctattacc   1560
tatgttcgag agaaggtcat cgacttttcc aagcccttta tgacacttgg aataagtatt   1620
ttgtaccgca agcccaatgg tacaaaccca ggcgtcttct ccttcctgaa tcctctctcc   1680
cctgatatct ggatgtatat tctgctggct tacttgggtg tcagttgtgt gctctttgtc   1740
atagccaggt ttagtcctta tgagtggtat aatccacacc cttgcaaccc tgactcagac   1800
gtggtggaaa acaattttac cttgctaaat agtttctggt ttggagttgg agctctcatg   1860
cagcaaggtt ctgagctcat gcccaaagca ctgtccacca ggatagtggg aggcatttgg   1920
tggtttttca cacttatcat catttcttcg tatactgcta acttagccgc ctttctgaca   1980
gtggaacgca tggaatcccc tattgactct gctgatgatt tagctaaaca aaccaagata   2040
gaatatggag cagtagagga tggtgcaacc atgacttttt tcaagaaatc aaaaatctcc   2100
acgtatgaca aaatgtgggc ctttatgagt agcagaaggc agtcagtgct ggtcaaaagt   2160
aatgaagaag gaatccagcg agtcctcacc tctgattatg ctttcctaat ggagtcaaca   2220
accatcgagt ttgttaccca gcggaactgt aacctgacac agattggcgg ccttatagac   2280
tctaaaggtt atggcgttgg cactcccatg ggttctccat atcgagacaa aattaccata   2340
gcaattcttc agctgcaaga ggaaggcaaa ctgcatatga tgaaggagaa atggtggagg   2400
ggcaatggtt gcccagaaga ggagagcaaa gaggccagtg ccctgggggt tcagaatatt   2460
ggtggcatct tcattgttct ggcagccggc ttggtgcttt cagtttttgt ggcagtggga   2520
gaatttttat acaaatccaa aaaaaacgct caattggaaa agaggtcctt ctgtagtgcc   2580
atggtagaag aattgaggat gtccctgaag tgccagcgtc ggttaaaaca taagccacag   2640
gccccagtta ttgtgaaaac agaagaagtt atcaacatgc acacatttaa cgacagaagg   2700
ttgccaggta aagaaaccat ggcataa                                      2727
```

<210> SEQ ID NO 12
<211> LENGTH: 2610
<212> TYPE: DNA
<213> ORGANISM: Homo sapiens

<400> SEQUENCE: 12

```
atgaagatta ttttcccgat tctaagtaat ccagtcttca ggcgcaccgt taaactcctg     60
ctctgtttac tgtggattgg atattctcaa ggaaccacac atgtattaag atttggtggt    120
atttttgaat atgtggaatc tggcccaatg ggagctgagg aacttgcatt cagatttgct    180
gtgaacacaa ttaacagaaa cagaacattg ctacccaata ctacccttac ctatgatacc    240
cagaagataa acctttatga tagttttgaa gcatccaaga aagcctgtga tcagctgtct    300
cttggggtgg ctgccatctt cgggccttca cacagctcat cagcaaacgc agtgcagtcc    360
atctgcaatg ctctgggagt tccccacata cagacccgct ggaagcacca ggtgtcagac    420
aacaaagatt ccttctatgt cagtctctac ccagacttct cttcactcag ccgtgccatt    480
ttagacctgg tgcagttttt caagtggaaa accgtcacgg ttgtgtatga tgacagcact    540
ggtctcattc gtttgcaaga gctcatcaaa gctccatcaa ggtataatct tcgactcaaa    600
attcgtcagt tacctgctga tacaaaggat gcaaaaccct tactaaaaga aatgaaaaga    660
```

ggcaaggagt ttcatgtaat ctttgattgt agccatgaaa tggcagcagg cattttaaaa 720
caggcattag ctatgggaat gatgacagaa tactatcatt atatctttac cactctggac 780
ctctttgctc ttgatgttga gccctaccga tacagtggtg ttaacatgac agggttcaga 840
atattaaata cagaaaatac ccaagtctcc tccatcattg aaaagtggtc gatggaacga 900
ttgcaggcac ctccgaaacc cgattcaggt ttgctggatg gatttatgac gactgatgct 960
gctctaatgt atgatgctgt gcatgtggtg tctgtggccg ttcaacagtt tccccagatg 1020
acagtcagtt ccttgcagtg taatcgacat aaaccctggc gcttcgggac ccgctttatg 1080
agtctaatta aagaggcaca ttgggaaggc ctcacaggca gaataacttt caacaaaacc 1140
aatggcttga gaacagattt tgatttggat gtgatcagtc tgaaggaaga aggtctagaa 1200
aagattggaa cgtgggatcc agccagtggc ctgaatatga cagaaagtca aaagggaaag 1260
ccagcgaaca tcacagattc cttatccaat cgttctttga ttgttaccac cattttggaa 1320
gagccttatg tcctttttaa gaagtctgac aaacctctct atggtaatga tcgatttgaa 1380
ggctattgca ttgatctcct cagagagtta tctacaatcc ttggctttac atatgaaatt 1440
agacttgtgg aagatgggaa atatggagcc caggatgatg ccaatggaca atggaatgga 1500
atggttcgtg aactaattga tcataaagct gaccttgcag ttgctccact ggctattacc 1560
tatgttcgag agaaggtcat cgacttttcc aagcccttta tgacacttgg aataagtatt 1620
ttgtaccgca agcccaatgg tacaaaccca ggcgtcttct ccttcctgaa tcctctctcc 1680
cctgatatct ggatgtatat tctgctggct tacttgggtg tcagttgtgt gctctttgtc 1740
atagccaggt ttagtcctta tgagtggtat aatccacacc cttgcaaccc tgactcagac 1800
gtggtggaaa acaattttac cttgctaaat agtttctggt ttggagttgg agctctcatg 1860
cagcaaggtt ctgagctcat gcccaaagca ctgtccacca ggatagtggg aggcatttgg 1920
tggtttttca cacttatcat catttcttcg tatactgcta acttagccgc ctttctgaca 1980
gtggaacgca tggaatcccc tattgactct gctgatgatt tagctaaaca aaccaagata 2040
gaatatggag cagtagagga tggtgcaacc atgacttttt tcaagaaatc aaaaatctcc 2100
acgtatgaca aaatgtgggc ctttatgagt agcagaaggc agtcagtgct ggtcaaaagt 2160
aatgaagaag gaatccagcg agtcctcacc tctgattatg ctttcctaat ggagtcaaca 2220
accatcgagt ttgttaccca gcggaactgt aacctgacac agattggcgg ccttatagac 2280
tctaaaggtt atggcgttgg cactcccatg ggttctccat atcgagacaa aattaccata 2340
gcaattcttc agctgcaaga ggaaggcaaa ctgcatatga tgaaggagaa atggtggagg 2400
ggcaatggtt gcccagaaga ggagagcaaa gaggccagtg ccctgggggt tcagaatatt 2460
ggtggcatct tcattgttct ggcagccggc ttggtgcttt cagtttttgt ggcagtggga 2520
gaatttttat acaaatccaa aaaaaacgct caattggaaa aggaatcttc tatttggtta 2580
gtgccaccat accatccaga cactgtttag 2610

<210> SEQ ID NO 13
<211> LENGTH: 2679
<212> TYPE: DNA
<213> ORGANISM: Homo sapiens

<400> SEQUENCE: 13
atgaagatta ttttcccgat tctaagtaat ccagtcttca ggcgcaccgt taaactcctg 60
ctctgtttac tgtggattgg atattctcaa ggaaccacac atgtattaag atttggtggt 120

-continued

```
atttttgaat atgtggaatc tggcccaatg ggagctgagg aacttgcatt cagatttgct    180
gtgaacacaa ttaacagaaa cagaacattg ctacccaata ctacccttac ctatgatacc    240
cagaagataa acctttatga tagttttgaa gcatccaaga aagcctgtga tcagctgtct    300
cttggggtgg ctgccatctt cgggccttca cacagctcat cagcaaacgc agtgcagtcc    360
atctgcaatg ctctgggagt tccccacata cagacccgct ggaagcacca ggtgtcagac    420
aacaaagatt ccttctatgt cagtctctac ccagacttct cttcactcag ccgtgccatt    480
ttagacctgg tgcagttttt caagtggaaa accgtcacgg ttgtgtatga tgacagcact    540
ggtctcattc gtttgcaaga gctcatcaaa gctccatcaa ggtataatct tcgactcaaa    600
attcgtcagt tacctgctga tacaaaggat gcaaaaccct tactaaaaga aatgaaaaga    660
ggcaaggagt ttcatgtaat ctttgattgt agccatgaaa tggcagcagg cattttaaaa    720
caggcattag ctatgggaat gatgacagaa tactatcatt atatctttac cactctggac    780
ctctttgctc ttgatgttga gccctaccga tacagtggtg ttaacatgac agggttcaga    840
atattaaata cagaaaatac ccaagtctcc tccatcattg aaaagtggtc gatggaacga    900
ttgcaggcac ctccgaaacc cgattcaggt ttgctggatg gatttatgac gactgatgct    960
gctctaatgt atgatgctgt gcatgtggtg tctgtggccg ttcaacagtt tccccagatg   1020
acagtcagtt ccttgcagtg taatcgacat aaaccctggc gcttcgggac ccgctttatg   1080
agtctaatta aagaggcaca ttgggaaggc ctcacaggca gaataacttt caacaaaacc   1140
aatggcttga gaacagattt tgatttggat gtgatcagtc tgaaggaaga aggtctagaa   1200
aagattggaa cgtgggatcc agccagtggc ctgaatatga cagaaagtca aaagggaaag   1260
ccagcgaaca tcacagattc cttatccaat cgttctttga ttgttaccac catttttggaa  1320
gagccttatg tcctttttaa gaagtctgac aaacctctct atggtaatga tcgatttgaa   1380
ggctattgca ttgatctcct cagagagtta tctacaatcc ttggctttac atatgaaatt   1440
agacttgtgg aagatgggaa atatggagcc caggatgatg ccaatggaca atggaatgga   1500
atggttcgtg aactaattga tcataaagct gaccttgcag ttgctccact ggctattacc   1560
tatgttcgag agaaggtcat cgacttttcc aagcccttta tgacacttgg aataagtatt   1620
ttgtaccgca agcccaatgg tacaaaccca ggcgtcttct ccttcctgaa tcctctctcc   1680
cctgatatct ggatgtatat tctgctggct tacttgggtg tcagttgtgt gctctttgtc   1740
atagccaggt ttagtcctta tgagtggtat aatccacacc cttgcaaccc tgactcagac   1800
gtggtggaaa acaattttac cttgctaaat agtttctggt ttggagttgg agctctcatg   1860
cagcaaggtt ctgagctcat gcccaaagca ctgtccacca ggatagtggg aggcatttgg   1920
tggtttttca cacttatcat catttcttcg tatactgcta acttagccgc ctttctgaca   1980
gtggaacgca tggaatcccc tattgactct gctgatgatt tagctaaaca aaccaagata   2040
gaatatggag cagtagagga tggtgcaacc atgacttttt tcaagaaatc aaaaatctcc   2100
acgtatgaca aaatgtgggc ctttatgagt agcagaaggc agtcagtgct ggtcaaaagt   2160
aatgaagaag gaatccagcg agtcctcacc tctgattatg ctttcctaat ggagtcaaca   2220
accatcgagt ttgttaccca gcggaactgt aacctgacac agattggcgg ccttatagac   2280
tctaaaggtt atggcgttgg cactcccatg ggttctccat atcgagacaa aattaccata   2340
gcaattcttc agctgcaaga ggaaggcaaa ctgcatatga tgaaggagaa atggtggagg   2400
ggcaatggtt gcccagaaga ggagagcaaa gaggccagtg ccctgggggt tcagaatatt   2460
ggtggcatct tcattgttct ggcagccggc ttggtgcttt cagtttttgt ggcagtggga   2520
```

gaatttttat acaaatccaa aaaaaacgct caattggaaa agagagccaa gactaagtta 2580
cctcaagact atgtattcct ccctattttg gagtcagttt ccatttctac agtgttgtca 2640
tcatcaccat cttcatcatc attatcatca tgttcttaa 2679

<210> SEQ ID NO 14
<211> LENGTH: 22
<212> TYPE: DNA
<213> ORGANISM: Homo sapiens

<400> SEQUENCE: 14
cccatagcta atgcctgttt ta 22

<210> SEQ ID NO 15
<211> LENGTH: 22
<212> TYPE: DNA
<213> ORGANISM: Mus musculus

<400> SEQUENCE: 15
cccatagcta atgcctgctt ta 22

<210> SEQ ID NO 16
<211> LENGTH: 22
<212> TYPE: RNA
<213> ORGANISM: Homo sapiens

<400> SEQUENCE: 16
uaaaacaggc auuagcuaug gg 22

<210> SEQ ID NO 17
<211> LENGTH: 22
<212> TYPE: RNA
<213> ORGANISM: Mus musculus

<400> SEQUENCE: 17
uaaagcaggc auuagcuaug gg 22

<210> SEQ ID NO 18
<211> LENGTH: 22
<212> TYPE: RNA
<213> ORGANISM: Homo sapiens

<400> SEQUENCE: 18
cccauagcua augccuguuu ua 22

<210> SEQ ID NO 19
<211> LENGTH: 22
<212> TYPE: RNA
<213> ORGANISM: Mus musculus

<400> SEQUENCE: 19
cccauagcua augccugcuu ua 22

<210> SEQ ID NO 20
<211> LENGTH: 61
<212> TYPE: DNA
<213> ORGANISM: Homo sapiens

<400> SEQUENCE: 20
taaaacaggc attagctatg ggtagtgaag ccacagatgc ccatagctaa tgcctgtttt 60
a 61

<210> SEQ ID NO 21
<211> LENGTH: 339
<212> TYPE: DNA
<213> ORGANISM: Homo sapiens

<400> SEQUENCE: 21
tcgactaggg ataacagggt aattgtttga atgaggcttc agtactttac agaatcgttg 60
cctgcacatc ttggaaacac ttgctgggat tacttcttca ggttaaccca acagaaggct 120
cgagaaggta tattgctgtt gacagtgagc gctaaaacag gcattagcta tgggtagtga 180
agccacagat gcccatagct aatgcctgtt ttattgccta ctgcctcgga attcaagggg 240
ctactttagg agcaattatc ttgtttacta aaactgaata ccttgctatc tctttgatac 300
atttttacaa agctgaatta aaatggtata aattatcac 339

<210> SEQ ID NO 22
<211> LENGTH: 61
<212> TYPE: DNA
<213> ORGANISM: Homo sapiens

<400> SEQUENCE: 22
cccatagcta atgcctgttt tatagtgaag ccacagatgt aaaacaggca ttagctatgg 60
g 61

<210> SEQ ID NO 23
<211> LENGTH: 339
<212> TYPE: DNA
<213> ORGANISM: Homo sapiens

<400> SEQUENCE: 23
tcgactaggg ataacagggt aattgtttga atgaggcttc agtactttac agaatcgttg 60
cctgcacatc ttggaaacac ttgctgggat tacttcttca ggttaaccca acagaaggct 120
cgagaaggta tattgctgtt gacagtgagc gccccatagc taatgcctgt tttatagtga 180
agccacagat gtaaaacagg cattagctat gggttgccta ctgcctcgga attcaagggg 240
ctactttagg agcaattatc ttgtttacta aaactgaata ccttgctatc tctttgatac 300
atttttacaa agctgaatta aaatggtata aattatcac 339

<210> SEQ ID NO 24
<211> LENGTH: 121
<212> TYPE: DNA
<213> ORGANISM: Homo sapiens

<400> SEQUENCE: 24
tcgactaggg ataacagggt aattgtttga atgaggcttc agtactttac agaatcgttg 60
cctgcacatc ttggaaacac ttgctgggat tacttcttca ggttaaccca acagaaggct 120
c 121

<210> SEQ ID NO 25
<211> LENGTH: 17
<212> TYPE: DNA
<213> ORGANISM: Homo sapiens

<400> SEQUENCE: 25
tagtgaagcc acagatg 17

<210> SEQ ID NO 26
<211> LENGTH: 105

<212> TYPE: DNA
<213> ORGANISM: Homo sapiens

<400> SEQUENCE: 26
aaggggctac tttaggagca attatcttgt ttactaaaac tgaatacctt gctatctctt 60
tgatacattt ttacaaagct gaattaaaat ggtataaatt atcac 105

<210> SEQ ID NO 27
<211> LENGTH: 429
<212> TYPE: DNA
<213> ORGANISM: Homo sapiens

<400> SEQUENCE: 27
ctgcagaggg ccctgcgtat gagtgcaagt gggttttagg accaggatga ggcggggtgg 60
gggtgcctac ctgacgaccg accccgaccc actggacaag cacccaaccc ccattcccca 120
aattgcgcat cccctatcag agagggggag gggaaacagg atgcggcgag gcgcgtgcgc 180
actgccagct tcagcaccgc ggacagtgcc ttcgcccccg cctggcggcg cgcgccaccg 240
ccgcctcagc actgaaggcg cgctgacgtc actcgccggt cccccgcaaa ctccccttcc 300
cggccacctt ggtcgcgtcc gcgccgccgc cggcccagcc ggaccgcacc acgcgaggcg 360
cgagataggg gggcacgggc gcgaccatct gcgctgcggc gccggcgact cagcgctgcc 420
tcagtctgc 429

<210> SEQ ID NO 28
<211> LENGTH: 469
<212> TYPE: DNA
<213> ORGANISM: Homo sapiens

<400> SEQUENCE: 28
ctgcagaggg ccctgcgtat gagtgcaagt gggttttagg accaggatga ggcggggtgg 60
gggtgcctac ctgacgaccg accccgaccc actggacaag cacccaaccc ccattcccca 120
aattgcgcat cccctatcag agagggggag gggaaacagg atgcggcgag gcgcgtgcgc 180
actgccagct tcagcaccgc ggacagtgcc ttcgcccccg cctggcggcg cgcgccaccg 240
ccgcctcagc actgaaggcg cgctgacgtc actcgccggt cccccgcaaa ctccccttcc 300
cggccacctt ggtcgcgtcc gcgccgccgc cggcccagcc ggaccgcacc acgcgaggcg 360
cgagataggg gggcacgggc gcgaccatct gcgctgcggc gccggcgact cagcgctgcc 420
tcagtctgcc aattgcagcg gaggagtcgt gtcgtgcctg agagcgcag 469

<210> SEQ ID NO 29
<211> LENGTH: 313
<212> TYPE: DNA
<213> ORGANISM: Mus musculus

<400> SEQUENCE: 29
atccgacgcc gccatctcta ggcccgcgcc ggccccctcg cacagacttg tgggagaagc 60
tcggctactc ccctgccccg gttaatttgc atataatatt tcctagtaac tatagaggct 120
taatgtgcga taaaagacag ataatctgtt ctttttaata ctagctacat tttacatgat 180
aggcttggat ttctataaga gatacaaata ctaaattatt attttaaaaa acagcacaaa 240
aggaaactca ccctaactgt aaagtaattg tgtgttttga gactataaat atcccttgga 300
gaaaagcctt gtt 313

<210> SEQ ID NO 30

<211> LENGTH: 60
<212> TYPE: DNA
<213> ORGANISM: Homo sapiens

<400> SEQUENCE: 30
gatgctgacg aaggctcgcg aggctgtgag cagccacagt gccctgctca gaagccccgg     60

<210> SEQ ID NO 31
<211> LENGTH: 60
<212> TYPE: DNA
<213> ORGANISM: Homo sapiens

<400> SEQUENCE: 31
gtctcccgcg cccgcgcccg tgtcgccgcc gtgcccgcga gcgggagccg gagtcgccgc     60

<210> SEQ ID NO 32
<211> LENGTH: 60
<212> TYPE: DNA
<213> ORGANISM: Homo sapiens

<400> SEQUENCE: 32
cgtgtgcaga tgcagggcgc cggtgccctg cgggtgcggg tgcaggagca gcgtgtgcag     60

<210> SEQ ID NO 33
<211> LENGTH: 60
<212> TYPE: DNA
<213> ORGANISM: Homo sapiens

<400> SEQUENCE: 33
ccccacgcca ccctttctgg tcatctcccc tcccgccccg cccctgcgca cactccctcg     60

<210> SEQ ID NO 34
<211> LENGTH: 60
<212> TYPE: DNA
<213> ORGANISM: Homo sapiens

<400> SEQUENCE: 34
tctccccggt aaagtctcgc ggtgctgccg ggctcagccc cgtctcctcc tcttgctccc     60

<210> SEQ ID NO 35
<211> LENGTH: 1725
<212> TYPE: DNA
<213> ORGANISM: Homo sapiens

<400> SEQUENCE: 35
gacattgatt attgactagt tattaatagt aatcaattac ggggtcatta gttcatagcc     60
catatatgga gttccgcgtt acataactta cggtaaatgg cccgcctggc tgaccgccca    120
acgacccccg cccattgacg tcaataatga cgtatgttcc catagtaacg ccaataggga    180
ctttccattg acgtcaatgg gtggagtatt tacggtaaac tgcccacttg gcagtacatc    240
aagtgtatca tatgccaagt acgcccccta ttgacgtcaa tgacggtaaa tggcccgcct    300
ggcattatgc ccagtacatg accttatggg actttcctac ttggcagtac atctacgtat    360
tagtcatcgc tattaccatg gtcgaggtga gccccacgtt ctgcttcact ctccccatct    420
cccccccctc cccaccccca attttgtatt tatttatttt ttaattattt tgtgcagcga    480
tgggggcggg gggggggggg gggcgcgcgc caggcggggc ggggcggggc gaggggcggg    540
gcggggcgag gcggagaggt gcggcggcag ccaatcagag cggcgcgctc cgaaagtttc    600
cttttatggc gaggcggcgg cggcggcggc cctataaaaa gcgaagcgcg cggcgggcgg    660
gagtcgctgc gcgctgcctt cgccccgtgc cccgctccgc cgccgcctcg cgccgcccgc    720

-continued

```
cccggctctg actgaccgcg ttactcccac aggtgagcgg gcgggacggc ccttctcctc    780

cgggctgtaa ttagcgcttg gtttaatgac ggcttgtttc ttttctgtgg ctgcgtgaaa    840

gccttgaggg gctccgggag ggccctttgt gcggggggag cggctcgggg ggtgcgtgcg    900

tgtgtgtgtg cgtggggagc gccgcgtgcg gctccgcgct gcccggcggc tgtgagcgct    960

gcgggcgcgg cgcggggctt tgtgcgctcc gcagtgtgcg cgaggggagc gcggccgggg   1020

gcggtgcccc gcggtgcggg gggggctgcg aggggaacaa aggctgcgtg cggggtgtgt   1080

gcgtgggggg gtgagcaggg ggtgtgggcg cgtcggtcgg gctgcaaccc cccctgcacc   1140

cccctccccg agttgctgag cacggcccgg cttcgggtgc ggggctccgt acggggcgtg   1200

gcgcggggct cgccgtgccg ggcggggggt ggcggcaggt gggggtgccg ggcggggcgg   1260

ggccgcctcg ggccggggag ggctcggggg aggggcgcgg cggcccccgg agcgccggcg   1320

gctgtcgagg cgcggcgagc cgcagccatt gccttttatg gtaatcgtgc gagagggcgc   1380

agggacttcc tttgtcccaa atctgtgcgg agccgaaatc tgggaggcgc cgccgcaccc   1440

cctctagcgg gcgcggggcg aagcggtgcg gcgccggcag gaaggaaatg ggcggggagg   1500

gccttcgtgc gtcgccgcgc cgccgtcccc ttctccctct ccagcctcgg ggctgtccgc   1560

ggggggacgg ctgccttcgg gggggacggg gcagggcggg gttcggcttc tggcgtgtga   1620

ccggcggctc tagagcctct gctaaccatg ttcatgcctt cttctttttc ctacagctcc   1680

tgggcaacgt gctggttatt gtgctgtctc atcattttgg caaag                   1725


<210> SEQ ID NO 36
<211> LENGTH: 17
<212> TYPE: DNA
<213> ORGANISM: Artificial Sequence
<220> FEATURE:
<223> OTHER INFORMATION: Synthetic Construct

<400> SEQUENCE: 36

tttgtgaggg tctggtc                                                    17


<210> SEQ ID NO 37
<211> LENGTH: 21
<212> TYPE: RNA
<213> ORGANISM: Artificial Sequence
<220> FEATURE:
<223> OTHER INFORMATION: Synthetic Construct

<400> SEQUENCE: 37

uaauguuagu cauguccacc g                                               21
```